(12) United States Patent
Bremer et al.

(10) Patent No.: US 10,982,149 B2
(45) Date of Patent: Apr. 20, 2021

(54) CHIRAL COMPOUNDS

(71) Applicant: Merck Patent GmbH, Darmstadt (DE)

(72) Inventors: Matthias Bremer, Darmstadt (DE);
Edward Plummer, Darmstadt (DE);
Thomas Eichhorn, Darmstadt (DE);
Peter Schreiner, Wettenberg (DE);
Christian Kuehn, Hattersheim (DE)

(73) Assignee: Merck Patent GmbH, Darmstadt (DE)

( * ) Notice: Subject to any disclaimer, the term of this patent is extended or adjusted under 35 U.S.C. 154(b) by 281 days.

(21) Appl. No.: 15/766,175

(22) PCT Filed: Sep. 7, 2016

(86) PCT No.: PCT/EP2016/001510
§ 371 (c)(1),
(2) Date: Apr. 5, 2018

(87) PCT Pub. No.: WO2017/059942
PCT Pub. Date: Apr. 13, 2017

(65) Prior Publication Data
US 2018/0291271 A1  Oct. 11, 2018

(30) Foreign Application Priority Data
Oct. 6, 2015  (EP) .................................. 15188556

(51) Int. Cl.
| C07D 321/10 | (2006.01) |
| C09K 19/58 | (2006.01) |
| C09K 19/32 | (2006.01) |
| C09K 19/34 | (2006.01) |

(52) U.S. Cl.
CPC .......... C09K 19/588 (2013.01); C07D 321/10 (2013.01); C09K 2019/323 (2013.01); C09K 2019/3433 (2013.01)

(58) Field of Classification Search
CPC ............................ C07D 319/22; C07D 321/10
See application file for complete search history.

(56) References Cited

U.S. PATENT DOCUMENTS

| 7,223,450 B2 * | 5/2007 | Taugerbeck | ......... | C07D 321/00 252/299.01 |
| 7,425,356 B2 | 9/2008 | Taugerbeck | | |

FOREIGN PATENT DOCUMENTS

| WO | 2002034739 A1 | 5/2002 |
| WO | 2004046805 A1 | 11/2002 |
| WO | 2007039105 A1 | 4/2007 |

OTHER PUBLICATIONS

International Search Report PCT/EP2016/001510 dated Dec. 2, 2016.
Marco Bandin et al: "Synthesis and Characterization of New Enantiopure 7,7'-Disubstituted 2,2'-Dihydroxy-1,1'-binaphthyls: Useful Ligands for the Asymmetric Allylation Reaction of Aldehydes", European Journal of Organic Chemistry, Jul. 1, 1999 (Jul. 1, 1999), XP055322244.

* cited by examiner

Primary Examiner — Chanceity N Robinson
Assistant Examiner — Anna Malloy
(74) Attorney, Agent, or Firm — Millen, White, Zelano and Branigan, P.C.

(57) ABSTRACT

Chiral compounds of formula I

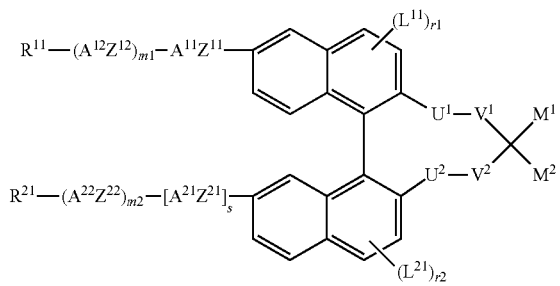

wherein the paramters have the meaning given in claim 1, liquid crystal mixtures comprising at least one chiral compound of formula I, to chiral linear or crosslinked liquid crystal polymers obtainable by polymerizing a polymerizable mixture comprising at least one chiral compound of formula I, to the use of chiral compound of formula I and mixtures and polymers obtained thereof in liquid crystal displays, active and passive optical elements, adhesives, synthetic resins with anisotropic mechanical properties, cosmetic and pharmaceutical compositions, diagnostics, liquid crystal pigments, for decorative and security applications, nonlinear optics, optical information storage or as chiral dopants, and a liquid crystal display comprising a mixture comprising at least one chiral compound of formula I.

1 Claim, No Drawings

CHIRAL COMPOUNDS

The invention relates to chiral compounds, to liquid crystal mixtures containing the chiral compounds, to polymers obtained from the chiral compounds and liquid crystal mixtures, and to the use of the chiral compounds, liquid crystal mixtures and polymers obtained thereof in liquid crystal displays, active and passive optical elements like polarizers, compensators, alignment layers, color filters or holographic elements, in adhesives, synthetic resins with anisotropic mechanical properties, cosmetic and pharmaceutical compositions, diagnostics, liquid crystal pigments, for decorative and security applications, in nonlinear optics, optical information storage or as chiral dopants.

Chiral compounds can be used as dopants to induce or enhance a helical twist in a liquid crystal mixture that is used for example in liquid crystal displays. The pitch p of the molecular helix in the first approximation, which is sufficient for most practical applications, is inversely proportional to the concentration c of the chiral dopant in the liquid crystal host mixture according to equation (1):

$$p = \frac{1}{HTP} \cdot \frac{1}{c} \quad (1)$$

The proportionality factor is the helical twisting power (HTP) of the chiral dopant.

For many applications it is desirable to have LC mixtures with a twisted phase. Among these are e.g. Blue Phase displays, phase-change displays, guest-host displays, passive and active matrix TN and STN displays like AMD-TN, ferroelectric displays and cholesteric displays like SSCT (surface stabilized cholesteric texture) or PSCT (polymer stabilized cholesteric texture) displays, including displays with temperature compensated characteristics, e.g. by appropriate selection of the cholesteric compounds according to the invention either alone or in combination with further chiral dopants. For these applications it is advantageous to have available a chiral dopant with a high HTP in order to reduce the amount of dopant needed to induce the desired pitch.

For some applications it is desired to have LC mixtures that exhibit a strong helical twist and thereby a short pitch length. For example in liquid crystal mixtures that are used in selectively reflecting cholesteric displays like SSCT or PSCT, the pitch has to be selected such that the maximum of the wavelength reflected by the cholesteric helix is in the range of visible light.

Another example are electro-optical displays and mesogenic light modulation media which are in the optically isotropic Blue Phase when being operated are described in WO 2004/046805. Liquid crystal Blue Phases are three-dimensional cubic defect structures, the characteristic period of which is of the order of the wavelength of visible light giving rise to reflections that are controllable with external fields. Obviously, a high amount of dielectrically neutral chiral dopant would lower the polarity of the mixture, thus leading to increased operating voltages. Especially Blue Phase LC displays where the reflection wavelength is in the UV range require chiral dopants with very high HTP.

Another possible application are polymer films with a chiral liquid crystal phase for optical elements, such as cholesteric broadband polarizers or retardation films.

As can be seen from equation (1), a short pitch can be achieved by using high amounts of dopant or by using a dopant with a high HTP.

Chiral compounds are disclosed for example in WO 95/16007, WO 98/00428 and GB 2 328 207 A.

However, the chiral dopants of prior art often exhibit low values of the HTP, so that high amounts of dopant are needed. This is a disadvantage because chiral dopants can be used only as pure enantiomers and are therefore expensive and difficult to synthesize.

Furthermore, when using chiral dopants of prior art in high amounts, they often negatively affect the properties of the liquid crystal host mixture, such as e.g. the clearing point, the dielectric anisotropy $\Delta\varepsilon$, the viscosity, the driving voltage or the switching times.

Another disadvantage of prior art chiral compounds is that they often show low solubility in the liquid crystal host mixture, which leads to undesired crystallization at low temperatures. To overcome this disadvantage, typically two or more different chiral dopants have to be added to the host mixture. This implies higher costs and also requires additional effort for temperature compensation of the mixture, as the different dopants have to be selected such that their temperature coefficients of the twist compensate each other.

A class of chiral dopants used in for example in LC mixtures for SSCT or Blue Phase applications is derived from optically active BINOL, as for example the following compound (R-5011, Merck KGaA Darmstadt),

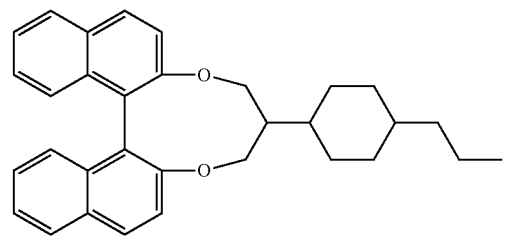 [SMILES: CCCC1CCC(C2COc3ccc4ccccc4c3-c3c(ccc4ccccc34)OC2)CC1]

disclosed in WO 02/094895. Similar compounds are disclosed in EP 1 326 854 B1. This compound has been used inter alia for polymer stabilised Blue Phase liquid crystal mixtures, as disclosed in e.g. WO 2014/053204 A1, EP 2 708 587 A1, WO2013156113A1, EP 2568032 B1 and WO 2012 163470 A1, where very high concentrations of typically around 4% of chiral dopant were necessary to achieve blue phase LC mixtures suitable for displays.

Consequently, there is a considerable demand for chiral compounds with a high HTP which are easy to synthesize, can be used in low amounts, show improved temperature stability of the cholesteric pitch e.g. for providing a substantially temperature-independent reflection wavelength, do not affect the properties of the liquid crystal host mixture and show good solubility in the host mixture.

The invention has the aim of providing chiral compounds having these properties, but which do not have the disadvantages of the chiral dopants of the state of the art as discussed above.

Another aim of the invention is to extend the pool of chiral compounds that can be used as dopants available to the expert.

Surprisingly it has been found that binaphthyl derivatives of formula I bearing one or two mesogenic units in the 7 and 7' positions of the binaphthyl moiety do not show the disadvantages of the compounds of the state of the art or at least do so to a much lesser extent.

Thus, one object of the present invention are chiral compounds of formula I

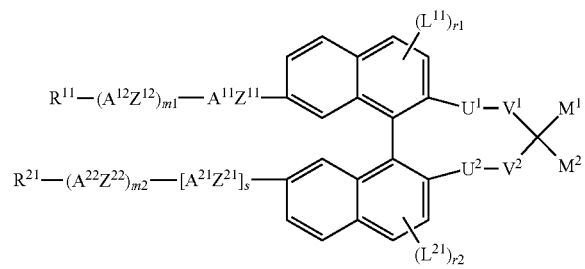

wherein $L^{11}$, $L^{21}$ each, identically or differently, denote F, Cl, Br, I, CN, SCN, SF$_5$, straight chain or branched alkyl with up to 25 C atoms which may be unsubstituted, mono- or poly-substituted by F, Cl, Br, I or CN, it being also possible for one or more non-adjacent CH$_2$ groups to be replaced, in each case independently from one another, by —O—, —S—, —NH—, —NR$^0$—, —CO—, —C(O)O—, —OC(O)—, —OC(O)O—, —S—C(O)—, —C(O)—S—, —CH=CH— or —C≡C— in such a manner that O and/or S atoms are not linked directly to one another, a polymerizable group, or cycloalkyl or aryl with up to 20 C atoms that is optionally mono- or polysubstituted by $L^{31}$ or by a polymerizable group, $R^0$ is H or alkyl with 1 to 4 C atoms, one of $M^1$ and $M^2$ is —Z$^{31}$-A$^{31}$-(Z$^{32}$-A$^{32}$)$_m$-R$^{31}$ and the other is R$^{41}$ or A$^{41}$, or both of M$^1$ and M$^2$ are, identically or differently, —Z$^{31}$-A$^{31}$-(Z$^{32}$-A$^{32}$)$_m$-R$^{31}$, or

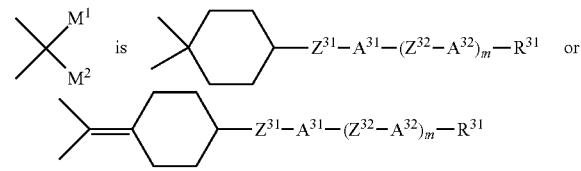

$U^1$ and $U^2$ each, identically or differently, denote —CH$_2$—, —CF$_2$—, —O—, —S—, —CO— or —CS—, $V^1$ and $V^2$ each, identically or differently, denote a single bond, or —(CH$_2$)$_n$—, wherein up to three non-adjacent CH$_2$-groups may be replaced by —O— and/or —S—, $Z^{11}$, $Z^{12}$, $Z^{21}$, $Z^{22}$, $Z^{31}$ and $Z^{32}$ each, identically or differently, denote —O—, —S—, —CO—, —C(O)O—, —OC(O)—, —O—C(O)O—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CH—, —CF=CH—, —CH=CF—, —CF=CF—, —C≡C—, —CH=CH—C(O)O—, —OC(O)—CH=CH— or a single bond, $A^{11}$, $A^{12}$, $A^{21}$, $A^{22}$, $A^{31}$, $A^{32}$, and $A^{41}$ each, identically or differently, denote 1,4-phenylene in which, in addition, one or more CH groups may be replaced by N, 1,4-cyclohexylene in which, in addition, one or two non-adjacent CH$_2$ groups may be replaced by O and/or S, 1,3-dioxolane-4,5-diyl, 1,4-cyclohexenylene, 1,4-bicyclo[2,2,2]octylene, piperidine-1,4-diyl, naphthalene-2,6-diyl, decahydronaphthalene-2,6-diyl, or 1,2,3,4-tetrahydronaphthalene-2,6-diyl, it being possible for all these groups to be unsubstituted, mono- or polysubstituted with $L^{31}$ $L^{31}$ each, identically or differently, denote halogen or a cyano, nitro, alkyl, alkoxy, alkylcarbonyl or alkoxycarbonyl group with 1 to 7 C atoms, wherein one or more H atoms may be substituted by F or Cl, $R^{11}$, $R^{21}R^{31}$ and $R^{41}$ each, identically or differently, denote H, F, Cl, Br, I, CN, SCN, OH, SF$_5$, straight chain or branched alkyl with up to 25 C atoms which may be unsubstituted, mono- or polysubstituted by F, Cl, Br, I or CN, it being also possible for one or more non-adjacent CH$_2$ groups to be replaced, in each case independently from one another, by —O—, —S—, —NH—, —NR$^0$—, —C(O)—, —C(O)O—, —OC(O)—, —OC(O)O—, —S—C(O)—, —CO—S—, —CH=CH— or —C≡C— in such a manner that O and/or S atoms are not linked directly to one another, or a polymerizable group.

m is 0, 1 or 2, m1, m2 each, identically or differently, is 0, 1, 2 or 3, and n is an integer from 1 to 7, r1, r2 each, identically or differently, denote 0, 1, 2, 3, 4 or 5, and s denotes 0 or 1.

Another object of the invention is a liquid crystal mixture containing at least one compound of formula I.

Another object of the present invention is a polymerizable liquid crystal mixture comprising at least one compound of formula I.

Another object of the invention is a linear or crosslinked anisotropic polymer with twisted structure obtainable from a polymerizable liquid crystal mixture comprising one or more compounds of formula I.

A further object of the invention is the use of compounds of formula I or a liquid crystal mixture or anisotropic polymer film comprising them in liquid crystal displays, such as Blue Phase, STN, TN, AMD-TN, temperature compensation, ferroelectric, guest-host, phase change or surface stabilized or polymer stabilized cholesteric texture (SSCT, PSCT) displays, in active and passive optical elements like polarizers, compensators, alignment layers, colour filters or holographic elements, in adhesives, synthetic resins with anisotropic mechanical properties, cosmetic and pharmaceutical compositions, diagnostics, liquid crystal pigments, for decorative and security applications, in nonlinear optics, optical information storage or as chiral dopants.

Yet another object of the invention is a liquid crystal display comprising a liquid crystal mixture comprising at least one chiral compound of formula I.

The inventive chiral compounds bear several advantages
 they exhibit a high HTP,
 they exhibit a good solubility in liquid crystal mixtures,
 they exhibit broad liquid crystalline phases or excellent mesogenic properties,
 when inventive compounds are used as chiral dopant in a liquid crystal mixture, due to their high solubility higher amounts of dopant can be used to produce a high twist (=a short pitch),
 in case high amounts of dopants are needed, due to the mesogenic character of the inventive dopants the liquid crystal phase of the host mixture is less negatively influenced, due to their high HTP, lower amounts of inventive dopants are needed to achieve a high pitch, and thereby the liquid crystalline properties of the mixture are less negatively affected, enantiomerically pure inventive chiral compounds are easy to prepare, both enantiomers are easily available.

The inventive chiral compounds are mesogenic or even liquid crystalline, i.e. they can induce or enhance mesophase behaviour for example in admixture with other compounds, or even exhibit one or more mesophases themselves. It is also possible that the inventive compounds show mesophase behaviour only in mixtures with other compounds, or, in case of polymerizable compounds, when being (co)polymerized.

Mesogenic inventive chiral compounds are especially preferred.

Especially preferred are compounds of formula I, wherein:

at least one of $U^1$ and $U^2$, very preferably both $U^1$ and $U^2$ are O.

$V^1$ and $V^2$ are $(CH_2)_n$, wherein n is 1, 2, 3 or 4, very preferably one of $V^1$ and $V^2$ is $CH_2$ and the other is $CH_2$ or $(CH_2)_2$.

one of $V^1$ and $V^2$ is $CH_2$ and the other is a single bond.

both of $V^1$ and $V^2$ are a single bond.

$Z^{21}$, $Z^{22}$, $Z^{31}$ and $Z^{32}$ are preferably, identically or differently, —C(O)O—, —OC(O)—, —OCH$_2$—, —CH$_2$O—, —CF$_2$O—, —OCF$_2$—, —CH$_2$CH$_2$—, —CF$_2$CF$_2$—, —CH=CH—, —CF=CF—, —C≡C—, or a single bond.

at least one of $Z^{31}$ and $Z^{32}$ is —CF$_2$O—, —OCF$_2$—, —CH$_2$CH$_2$— or —CF$_2$CF$_2$—. These compounds have a particularly high solubility in liquid crystal mixtures.

$Z^{31}$ is a single bond.

$Z^{31}$ denotes —CH$_2$—CH$_2$—.

$Z^{11}$ and $Z^{21}$ denote —C≡C—, —CH$_2$=CH$_2$—, CF$_2$=CF$_2$, or a single bond.

at least one of $Z^{11}$ and $Z^{21}$ is —C≡C—. These compounds are especially suitable for uses where highly birefringent materials are needed.

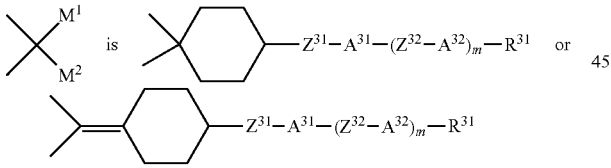

and m is 0 or 1, in particular 0, very preferably m is 0 and $A^{31}$ is a single bond.

M is $R^{41}$ or $A^{41}$, in particular H or F, and $M^2$ is —$Z^{31}$-$A^{31}$-$(Z^{32}$-$A^{32})_m$-$R^{31}$ with m being 0 or 1.

$r^1$ and $r^2$ are the same.

$r^1$ and $r^2$ are 1.

$r^1$ and $r^2$ are 0.

s denotes 0.

s denotes 1.

at least one, preferably one or two of $R^{11}$, $R^{21}$ $L^{11}$ and $L^{21}$ denote or comprise a polymerizable group.

$R^{31}$ is a polymerizable group.

$R^{11}$, $R^{21}$ and $R^{31}$ each, identically or differently, denote straight chain alkyl with 1 to 12 C atoms wherein one or more H atoms may be replaced with F or CN, it being also possible for one or more non-adjacent CH$_2$ groups to be replaced, in each case independently from one another, by —O—, —S—, —NH—, —N(CH$_3$)—, —CO—, —COO—, —OCO—, —OCO—O—, —S—CO—, —CO—S—, —CH=CH— or —C≡C— in such a manner that oxygen atoms are not linked directly to one another, very preferably alkyl or alkoxy with 1 to 12 C atoms.

$R^{11}$ and $R^{21}$ denote H.

$R^{31}$ is $(CH_2)_f$—OH, with f being 0 or an integer from 1 to 12.

$L^{11}$, $L^{21}$ and $R^{41}$ are selected from H, F and straight chain alkyl with 1 to 12 C atoms wherein one or more H atoms may be replaced with F or CN, it being also possible for one or more non-adjacent CH$_2$ groups to be replaced, in each case independently from one another, by —O—, —S—, —NH—, —N(CH$_3$)—, —CO—, —COO—, —OCO—, —OCO—O—, —S—CO—, —CO—S—, —CH=CH— or —C≡C— in such a manner that oxygen atoms are not linked directly to one another, and are very preferably H, F and alkyl or alkoxy with 1 to 12 C atoms.

$L^{11}$, $L^{12}$ are aryl, preferably phenyl, that is unsubstituted or mono- or polysubstituted, preferably monosubstituted in 4-position, with L.

$L^{31}$ is F, Cl, CN or optionally fluorinated alkyl, alkoxy, alkylcarbonyl or alkoxycarbonyl with 1 to 7 C-atoms.

$L^{31}$ is F, Cl, CN, NO$_2$, CH$_3$, C$_2$H$_5$, OCH$_3$, OC$_2$H$_5$, COCH$_3$, COC$_2$H$_5$, CF$_3$, CHF$_2$, CH$_2$F, OCF$_3$OCHF$_2$, OCH$_2$F or OC$_2$F$_5$.

$A^{41}$ is 1,4-phenylene or 1,4-cyclohexylene that is optionally substituted with up to 5, very preferably 1, 2 or 3 F or Cl atoms or CN, NO$_2$, alkyl, alkoxy, alkylcarbonyl or alkoxycarbonyl groups with 1 to 4 C atoms wherein one or more H atoms may be substituted by F or Cl.

$A^{31}$ and $A^{32}$ are selected from 1,4-phenylene and trans-1,4-cyclohexylene that are unsubstituted or substituted with up to 4 groups $L^{31}$.

the mesogenic group —$Z^{31}$-$A^{31}$-$(Z^{32}$-$A^{32})_m$ incorporates one, two or three five- or six-membered rings.

the mesogenic group —$Z^{31}$-$A^{31}$-$(Z^{32}$-$A^{32})_m$ is bicyclohexyl, biphenyl, phenylcyclohexyl, cyclohexylphenyl or biphenylcyclohexyl, wherein the phenyl rings are optionally substituted with one or two F atoms.

$A^{11}$ and $A^{21}$ both denote a single bond.

$A^{11}$ and $A^{21}$ both denote 2,6-naphthalenediyl and $R^1$ and $R^{12}$ denote H.

$A^{11}$, $A^{12}$, $A^{21}$ and $A^{22}$ are selected from 1,4-phenylene and trans-1,4-cyclohexylene that are unsubstituted or substituted with up to 4 groups $L^{11}$.

$A^{11}$ and $A^{12}$ are preferably an aromatic ring, preferably 1,4-phenylene that is unsubstituted or substituted with up to 4 groups $L^1$.

m is 0.

m is 1.

Further preferred are compounds wherein the mesogenic group comprises at least one group derived from 1,4-phenylen that is substituted with one or two groups $L^{31}$, preferably in 3- and/or 5-position, further preferably in 2- and/or 3-position, and L is F, Cl, CH$_3$, OCH$_3$, CF$_3$, CHF$_2$, CH$_2$F, OCF$_3$OCHF$_2$, OCH$_2$F or CN.

$L^{31}$ is preferably F, Cl, CN, NO$_2$, CH$_3$, C$_2$H$_5$, OCH$_3$, OC$_2$H$_5$, COCH$_3$, COC$_2$H$_5$, CF$_3$, CHF$_2$, CH$_2$F, OCF$_3$OCHF$_2$, OCH$_2$F, OC$_2$F$_5$, in particular F, Cl, CN, CH$_3$, CHF$_2$, C$_2$H$_5$, OCH$_3$, OCHF$_2$, CF$_3$ and OCF$_3$, most preferably F, CH$_3$, CF$_3$, OCH$_3$, OCHF$_2$ and OCF$_3$.

If $L^{11}$, $L^{21}$, $L^{31}$, $R^{11}$, $R^{21}$, $R^{31}$ or $R^{41}$ in formula I is an alkyl or alkoxy radical, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2- (=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

Halogen is preferably F or Cl.

$L^{11}$, $L^{21}$, $L^{31}$, $R^{11}$, $R^{21}$, $R^{31}$ or $R^{41}$ in formula I can be a polar or an unpolar group. In case of a polar group, it is selected from CN, OH, $SF_5$, halogen, $OCH_3$, SCN, $COR^5$, $COOR^5$ or a mono-oligo- or polyfluorinated alkyl or alkoxy group with 1 to 4 C atoms. $R^5$ is optionally fluorinated alkyl with 1 to 4, preferably 1 to 3 C atoms. Especially preferred polar groups are selected of F, Cl, CN, $OCH_3$, $COCH_3$, $COC_2H_5$, $COOCH_3$, $COOC_2H_5$, $CF_3$, $CHF_2$, $CH_2F$, $OCF_3$, $OCHF_2$, $OCH_2F$, $C_2F_5$ and $OC_2F_5$, in particular F, Cl, CN, $CF_3$, $OCHF_2$ and $OCF_3$. In case of an unpolar group, it is preferably alkyl with up to 15 C atoms or alkoxy with 2 to 15 C atoms.

$L^{11}$, $L^{21}$, $L^{31}$, $R^{11}$, $R^{21}$, $R^{31}$ or $R^{41}$ in formula I can be an achiral or a chiral group. In case of a chiral group it is preferably selected of formula II:

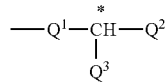

wherein $Q^1$ is an alkylene or alkylene-oxy group with 1 to 9 C atoms or a single bond, $Q^2$ is an alkyl or alkoxy group with 1 to 10 C atoms which may be unsubstituted, mono- or polysubstituted by F, Cl, Br or CN, it being also possible for one or more non-adjacent $CH_2$ groups to be replaced, in each case independently from one another, by —C≡C—, —O—, —S—, —NH—, —N($CH_3$)—, —CO—, —COO—, —OCO—, —OCO—O—, —S—CO— or —CO—S— in such a manner that oxygen atoms are not linked directly to one another, $Q^3$ is F, Cl, Br, CN or an alkyl or alkoxy group as defined for $Q^2$ but being different from $Q^2$.

In case $Q^1$ in formula II is an alkylene-oxy group, the O atom is preferably adjacent to the chiral C atom.

Preferred chiral groups of formula II are 2-alkyl, 2-alkoxy, 2-methylalkyl, 2-methylalkoxy, 2-fluoroalkyl, 2-fluoroalkoxy, 2-(2-ethin)-alkyl, 2-(2-ethin)-alkoxy, 1,1,1-trifluoro-2-alkyl and 1,1,1-trifluoro-2-alkoxy.

Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chlorpropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

In addition, compounds of formula I containing an achiral branched group $L^{11}$, $L^{21}$, $L^{31}$, $R^{11}$, $R^{21}$, $R^{31}$ or $R^{41}$ may occasionally be of importance, for example, due to a reduction in the tendency towards crystallization. Branched groups of this type generally do not contain more than one chain branch. Preferred achiral branched groups are isopropyl, isobutyl (=methylpropyl), isopentyl (=3-methylbutyl), isopropoxy, 2-methyl-propoxy and 3-methylbutoxy.

In case of compounds comprising a polymerizable group, this is preferably selected of the formula P-Sp-X, wherein P is $CH_2$=$CW^1$—COO—,

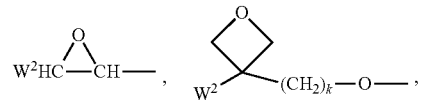

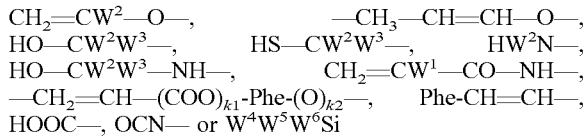

$CH_2$=$CW^2$—O—, —$CH_3$—CH=CH—O—, HO—$CW^2W^3$—, HS—$CW^2W^3$—, $HW^2N$—, HO—$CW^2W^3$—NH—, $CH_2$=$CW^1$—CO—NH—, —$CH_2$=CH—$(COO)_{k1}$-Phe-$(O)_{k2}$—, Phe-CH=CH—, HOOC—, OCN— or $W^4W^5W^6Si$

Sp is a spacer group having 1 to 25 C atoms or a single bond,

X is —O—, —S—, —$OCH_2$—, —$CH_2O$—, —CO—, —COO—, —OCO—, —OCO—O—, —CO—$NR^0$—, —$NR^0$—CO—, —$OCH_2$—, —$CH_2O$—, —$SCH_2$—, —$CH_2S$—, —CH=CH—COO—, —OOC—CH=CH— or a single bond, $W^1$ is H, Cl, CN, phenyl or alkyl with 1 to 5 C-atoms, in particular H, Cl or $CH_3$, $W^2$ and $W^3$ are independently of each other H or alkyl with 1 to 5 C-atoms, in particular methyl, ethyl or n-propyl, $W^4$, $W^5$ and $W^6$ are independently of each other Cl, oxaalkyl or oxacarbonylalkyl with 1 to 5 C-atoms, Phe is 1,4-phenylene, k1 and k2 are independently of each other 0 or 1, and $R^0$ is H or alkyl with 1 to 4 C atoms.

P is preferably a vinyl group, an acrylate group, a methacrylate group, a propenyl ether group or an epoxy group, especially preferably an acrylate or a methacrylate group.

In another preferred embodiment P is a branched group comprising two or more reactive moieties, like for example a group selected from —OC(O—$CR^0$($CH_2$—OCO—CW=$CH_2$)_2 and —OCO—C($CH_2$—OCO—CW=$CH_2$)_3, with W being H, Cl or $CH_3$ and R being H or alkyl with 1 to 4 C atoms, preferably H or methyl.

As for the spacer group Sp all groups can be used that are known for this purpose to the skilled in the art. The spacer group Sp is preferably a linear or branched alkylene group having 1 to 20 C atoms, in particular 1 to 12 C atoms, in which, in addition, one or more non-adjacent $CH_2$ groups may be replaced by —O—, —S—, —NH—, —N($CH_3$)—, —CO—, —O—CO—, —S—CO—, —O—COO—, —CO—S—, —CO—O—, —CH(halogen)-, —CH(CN)—, —CH=CH— or —C≡C—.

Typical spacer groups are for example —$(CH_2)_p$—, —$(CH_2CH_2O)_r$—$CH_2CH_2$—, —$CH_2CH_2$—S—$CH_2CH_2$— or —CH$_2$CH$_2$—NH—CH$_2$CH$_2$—, with p being an integer from 2 to 12 and r being an integer from 1 to 3.

Preferred spacer groups are ethylene, propylene, butylene, pentylene, hexylene, heptylene, octylene, nonylene, decylene, undecylene, dodecylene, octadecylene, ethylene-oxyethylene, methyleneoxybutylene, ethylene-thioethylene, ethylene-N-methyl-iminoethylene, 1-methylalkylene, ethenylene, propenylene and butenylene for example.

Especially preferred are inventive chiral compounds of formula I wherein Sp-X denotes alkylene or alkylene-oxy with 2 to 6 C atoms. Straight-chain groups are especially preferred.

In another preferred embodiment of the invention the chiral compounds comprise at least one spacer group Sp that is a chiral group of formula IV:

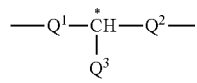

III wherein
Q$^1$ is an alkylene or alkylene-oxy group with 1 to 10 C atoms or a single bond,
Q$^2$ is an alkylene or alkylene-oxy group with 1 to 10 C atoms or a single bond, being different from Q$^1$, and
Q$^3$ is halogen, a cyano group or an alkyl or alkoxy group with 1 to 4 C atoms different from Q$^2$.

In case Q$^1$ in formula IV is an alkylene-oxy group, the O atom is preferably adjacent to the chiral C atom.

Particularly preferred compounds of formula I are those of the following formulae:

I-2
I-3
I-4
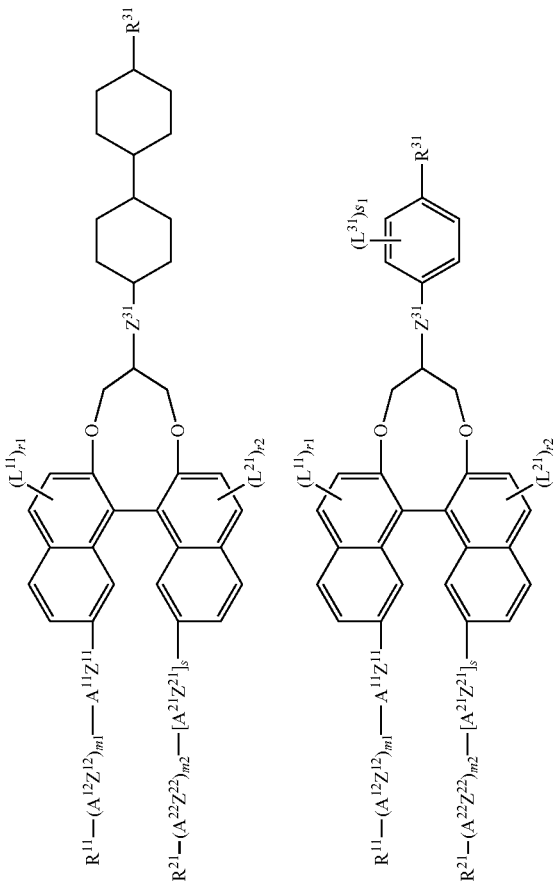

-continued
I-5
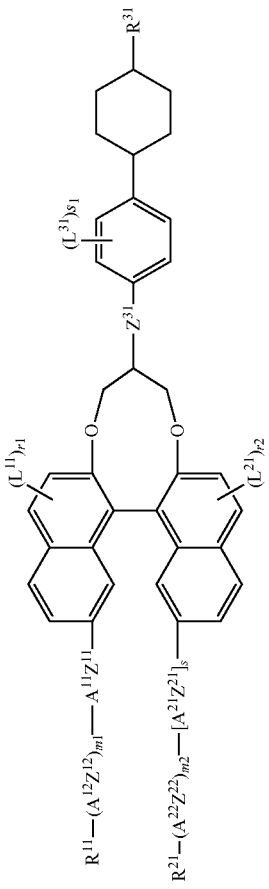
I-6
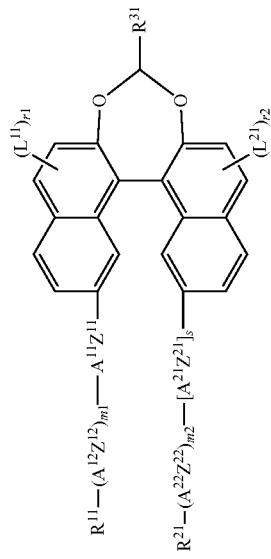

wherein the parameters have the meaning indicated above and preferably $A^{11}$, $A^{12}$, $A^{21}$, $A^{22}$ each, identically or differently, denote 1,4-phenylene, 1,4-cyclohexylene, naphthalene-2,6-diyl, it being possible for all these groups to be unsubstituted, mono- or polysubstituted with $L^{31}$ $R^{11}$, $R^{21}$ $R^{31}$ and $R^{41}$ each, identically or differently, denote H, F, Cl, CN, straight chain or branched alkyl with up to 7 C atoms which may be unsubstituted, mono- or polysubstituted by F, Cl, or CN, it being also possible for one or more non-adjacent CH$_2$ groups to be replaced, in each case independently from one another, by —O—, —CO—, —C(O)O—, —OC(O)—, —OCO—O—, —SC(O)—, —C(O)S—, —CH=CH— or —C≡C— in such a manner that —O— and/or —S— atoms are not linked directly to one another, or a polymerizable group.

$Z^{11}$, $Z^{12}$, $Z^{21}$, $Z^{22}$, each, identically or differently, denote —O—, —CO—, —C(O)O—, —OC(O)—, —O—C(O) O—, —OCH$_2$—, —CH$_2$O—, —CF$_2$O—, —OCF$_2$—, —CH$_2$CH$_2$—, —CF$_2$CH$_2$—, —CH$_2$CF$_2$—, —CF$_2$CF$_2$—, —CH=CH—, —CF=CH—, —CH=CF—, —CF=CF—, —C≡C—, —or a single bond, $Z^{31}$ each, identically or differently, denote —O—, —OC(O)—, —OCH$_2$—, —CH$_2$CH$_2$—, —CF$_2$CH$_2$—, —CH$_2$CF$_2$—, —CF$_2$CF$_2$— or a single bond, m1, m2 each, identically or differently, is 0, 1, 2 or 3, and r1, r2, s1 each, identically or differently, denote 0, 1 or 2, s denotes 0 or 1, $L^{11}$, $L^{21}$, $L^{31}$ each, identically or differently, denote F, Cl, or alkyl or alkoxy with 1 to 7 C atoms, wherein one or more H atoms may be substituted by F or Cl.

Particularly preferred compounds of formula I-1 to 1-6 are the following sub-formulae:

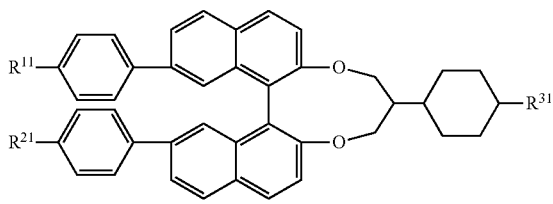

I-2a

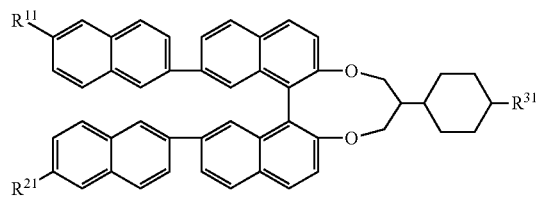

I-2b

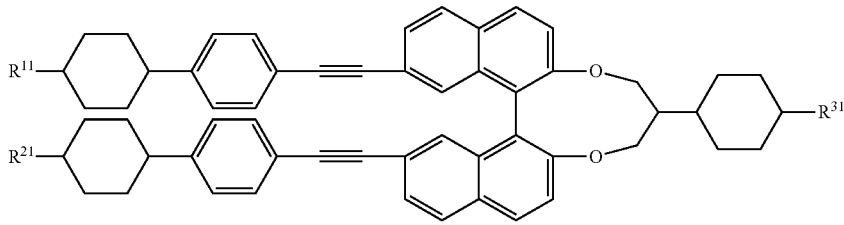

I-2c

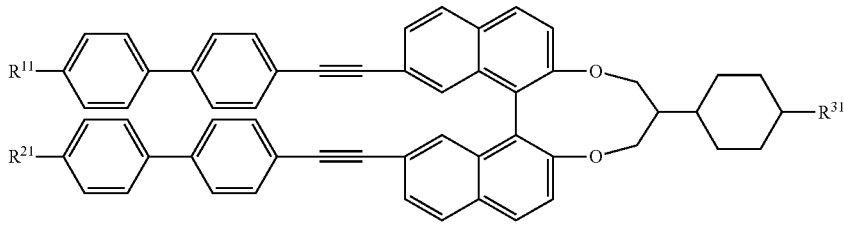

I-2d

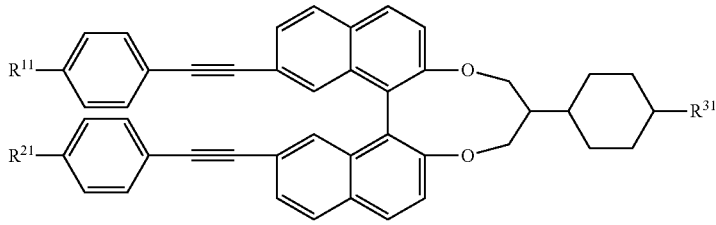

I-2e

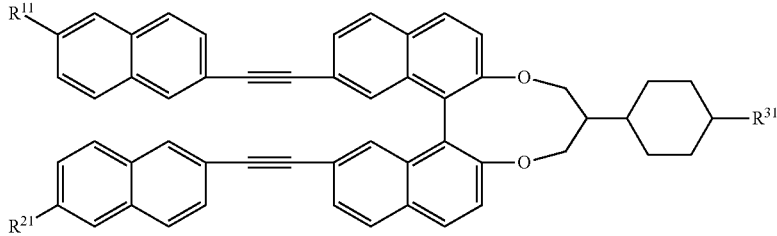

I-2f

-continued
I-2g
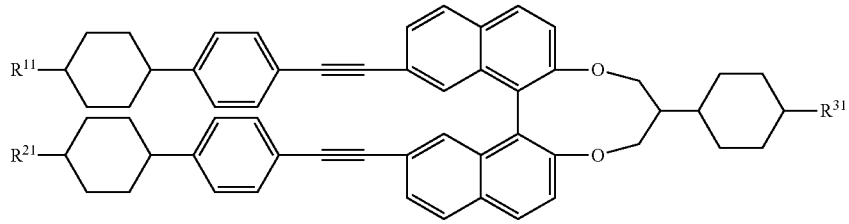
I-2h
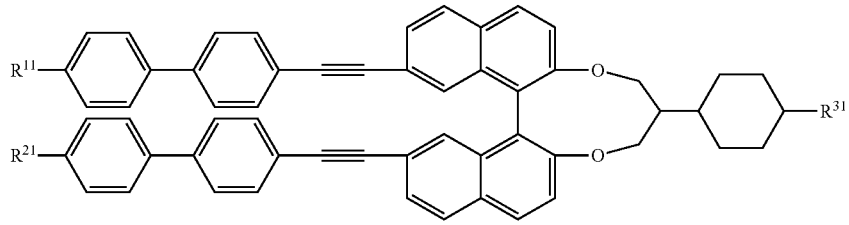
I-2i                    I-2j
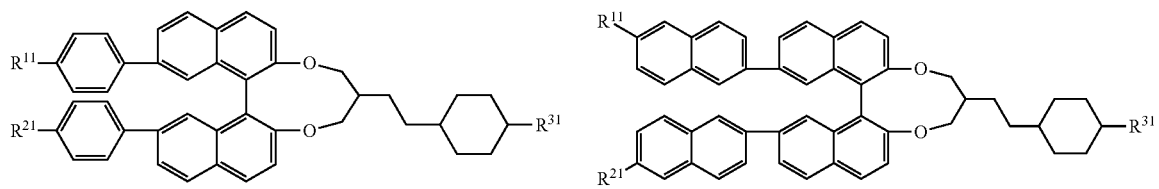
I-2k
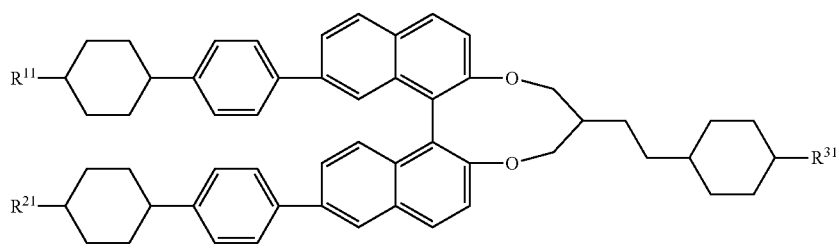
I-2l
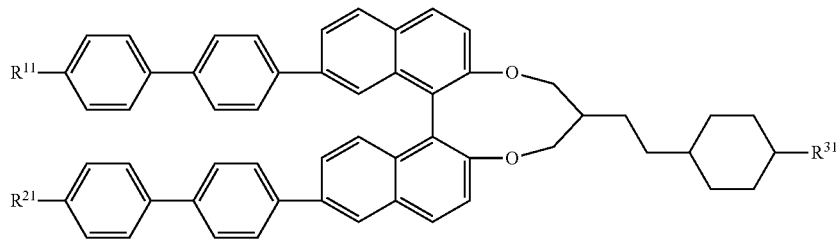
I-2m
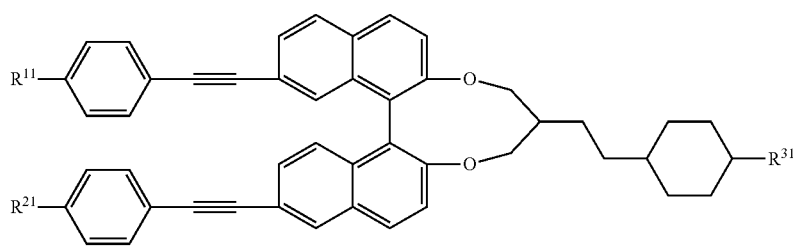

-continued
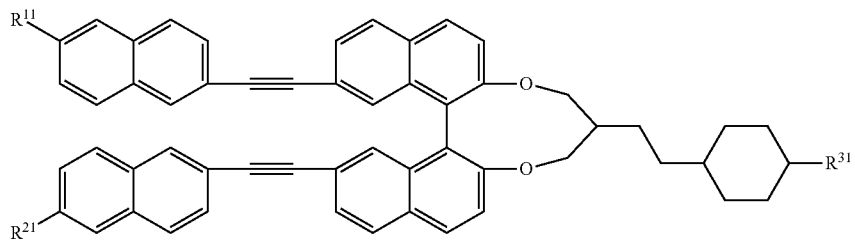
I-2n
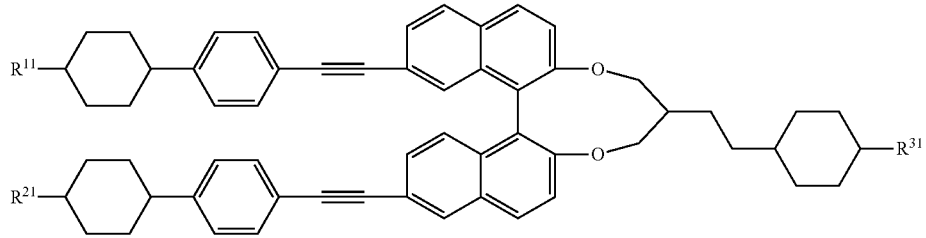
I-2o
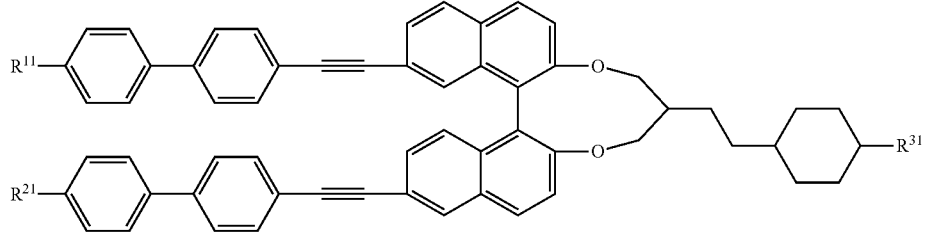
I-2p
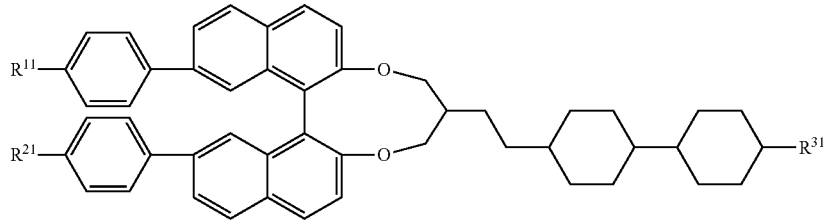
I-3a
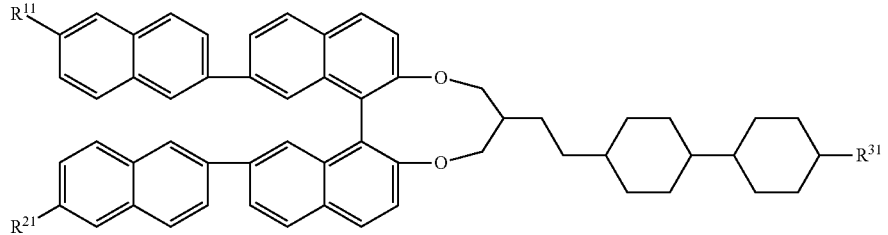
I-3b
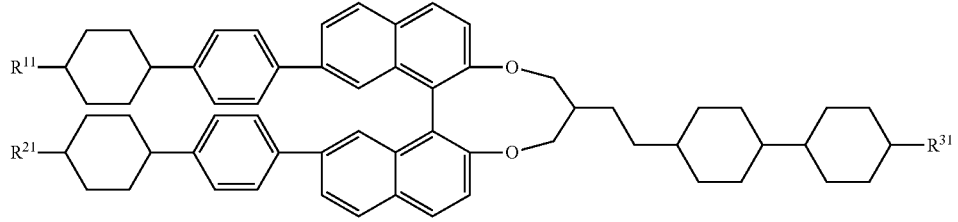
I-3c -continued
I-3d
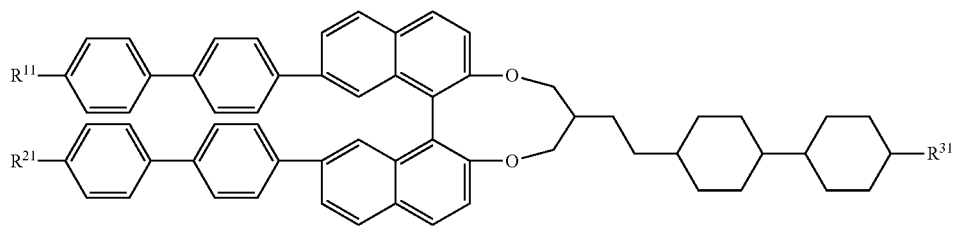
I-3e
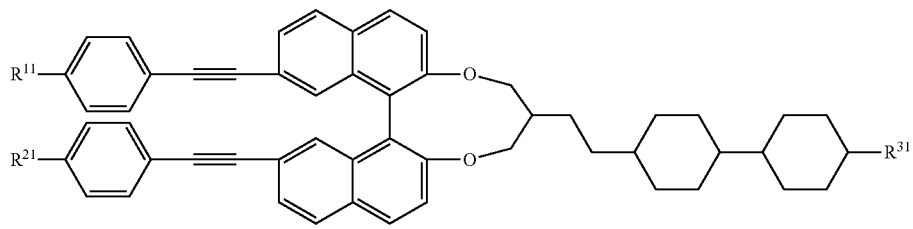
I-3f
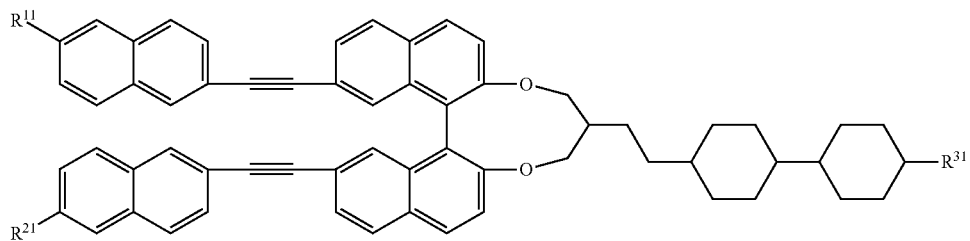
I-3g
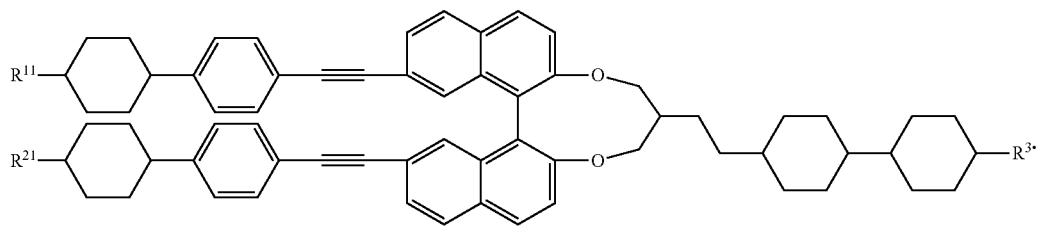
I-3h
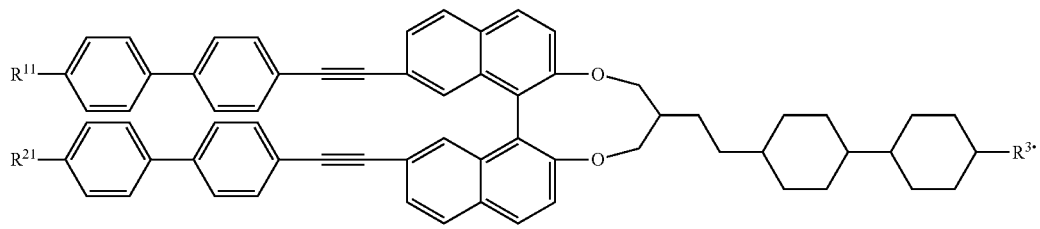
I-4a
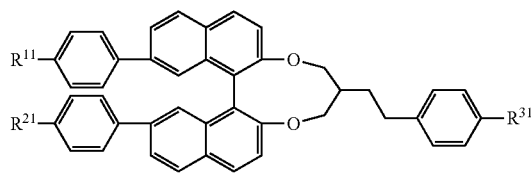
I-4b
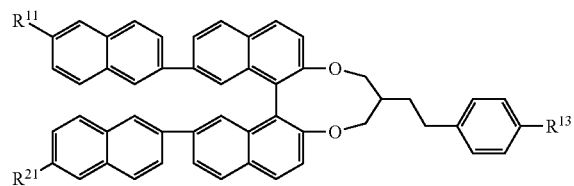
I-4c
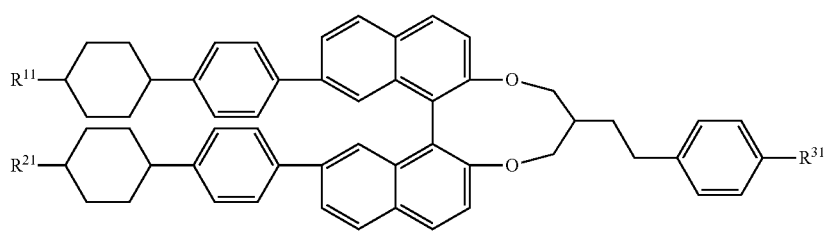

-continued
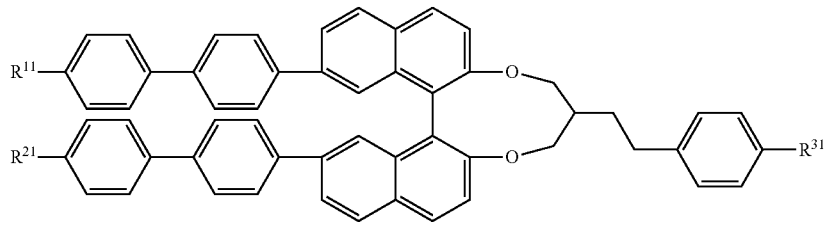
I-4d
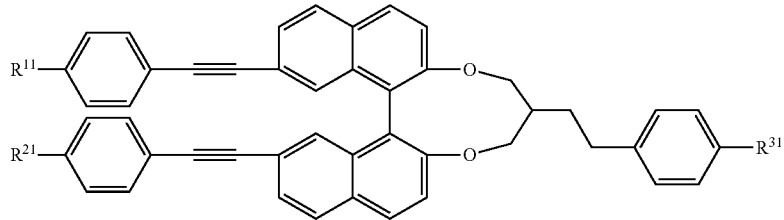
I-4e
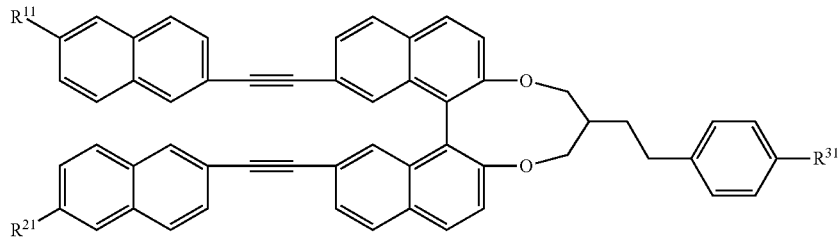
I-4f
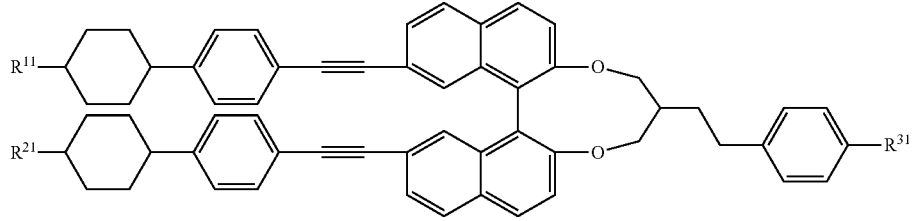
I-4g
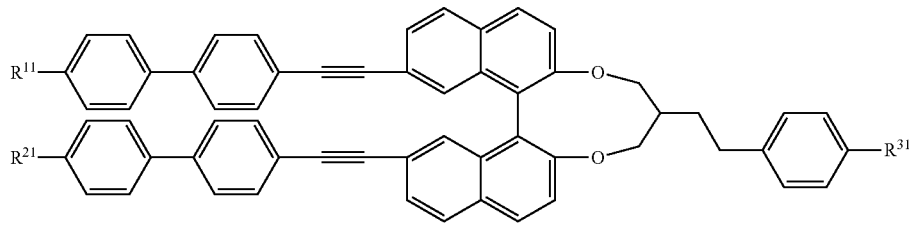
I-4h
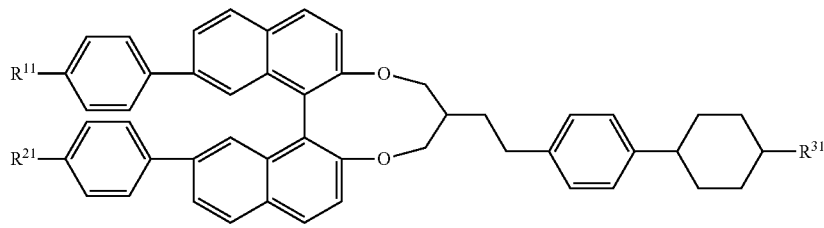
I-5a -continued
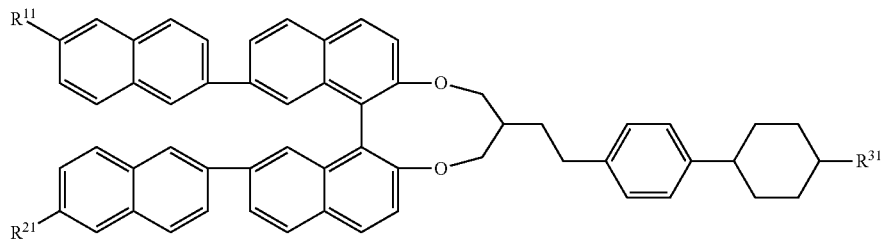
I-5b
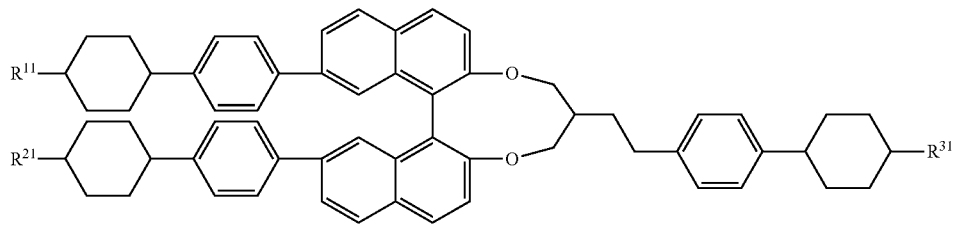
I-5c
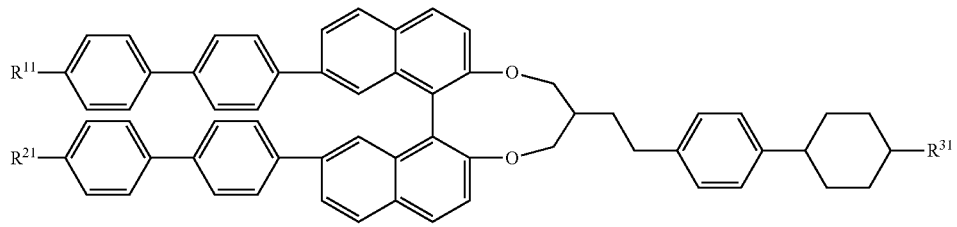
I-5d
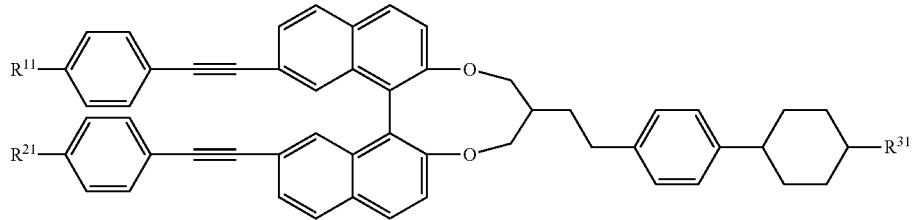
I-5e
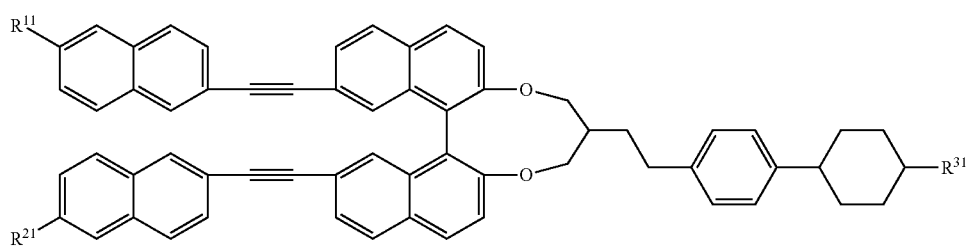
I-5f
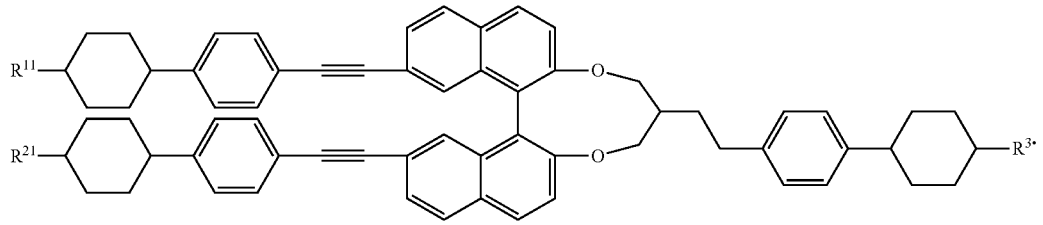
I-5g

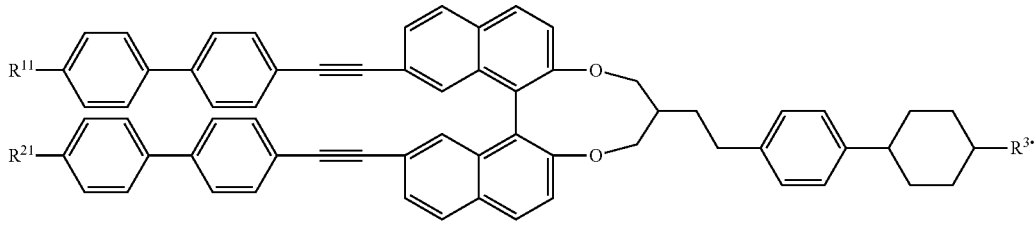

I-5h wherein $R^{11}$, $R^{21}$ and $R^{31}$ preferably denote H or Alkyl having 1 to 7 C atoms.

The chiral compounds according to the present invention can be synthesized by or in analogy to known methods. In particular, they can be prepared as described in or in analogy to the following reaction schemes.

Further methods for preparing the inventive compounds can be taken from the examples.

A preferred key intermediate is optically active 7,7'-dibromo-2,2'-dihydroxy-1,1'-binaphthyl (1), which can be synthesised in optically active form according to a method described in M. Bandin et al., *Eur. J. Org. Chem.* 2000, 491-497. Compound 1 is preferably transformed into cyclic ethers (3) by alkylation with suitable alkyl dihalogenides or sulfonates following standard procedures (scheme 1)

Scheme 1

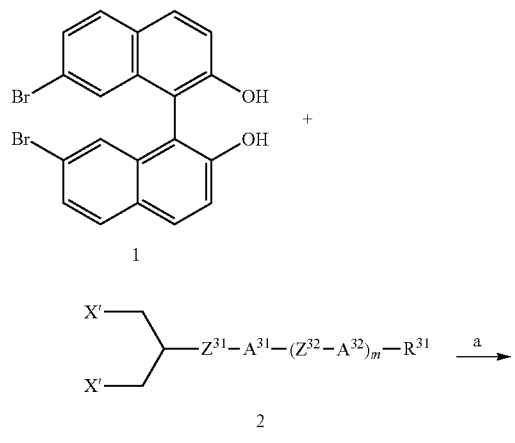

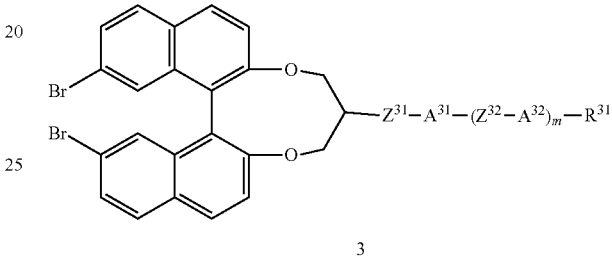

a) DMF, $K_2CO_3$, Δ; X'=Br, OTs, OMs

The dibromide 3 can then be converted into a large variety of derivatives using standard reactions described in literature. Preferred methods are transition metal catalysed transformations known as for example Suzuki, Negishi, Kumada or Sonogashira couplings for the introduction of substituents or mesogenic groups, as exemplified by the Suzuki and Sonogashira couplings in scheme 2.

Depending on the nature of the substituents or reagents it can be advantageous to first react the bromide of the binaphthyl (e.g. compound 3, scheme 2) and then perform the ring closure as shown in scheme 1.

The syntheses shown in schemes 1 and 2 exclusively give products wherein the mesogenic moieties $R^{11}$-($A^{12}Z^{12}$)$_{m1}A^{11}$- are the same, i.e. $R^{21}$-($A^{22}Z^{22}$)$_{m2}A^{21}$- in formula I is the same as $R^{11}$-($A^{12}Z^{12}$)$_{m1}A^{11}$-.

Scheme 2

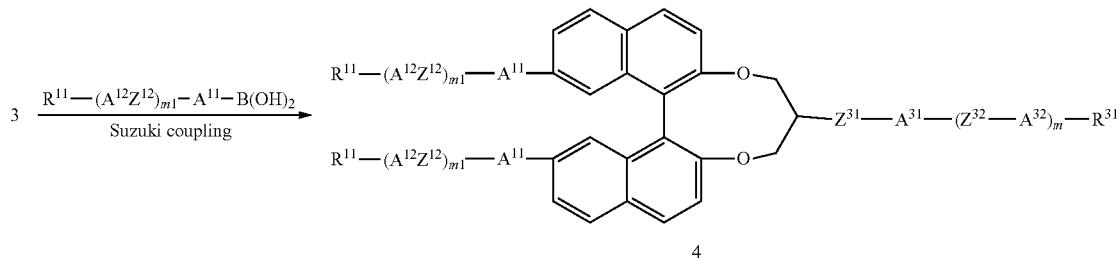

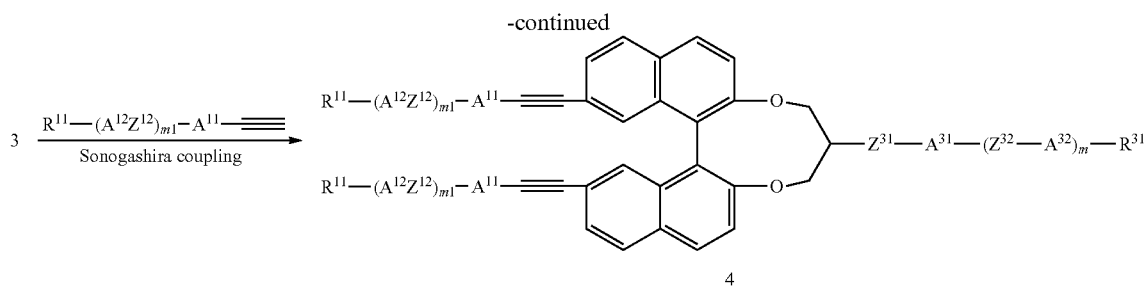

A synthesis of compounds where $R^{11}-(A^{12}Z^{12})_{m1}A^{11}-$ of formula I is different from $R^{21}-(A^{22}Z^{22})_{m2}A^{21}-$ is shown in scheme 3. Here, the above shown coupling reactions are performed starting from 7-bromo-2-naphthol to give naphthols 6a and 6b which are then oxidatively coupled, in analogy to the published procedure cited above for the preparation of 3, to give binaphthols 7. Resolution of the racemate of 7 is also possible according to procedures in the literature. Alternatively, a direct enantioselective oxidative coupling of naphthols 6a and 6b is possible using chiral catalysts as published in Q.-X. Guo et al., *J. Am. Chem. Soc.* 2007, 129, 13927-13938. Finally, compounds 7 are then reacted to give compounds of formula (I) following the procedure shown in scheme 1.

As the precursor of compounds 1, 7-bromo-2-naphthol, is comparatively expensive, the synthesis of the compounds according to the present invention preferably starts from 7-methoxy-2-naphthol which can also be coupled oxidatively to give binaphthols (scheme 4).

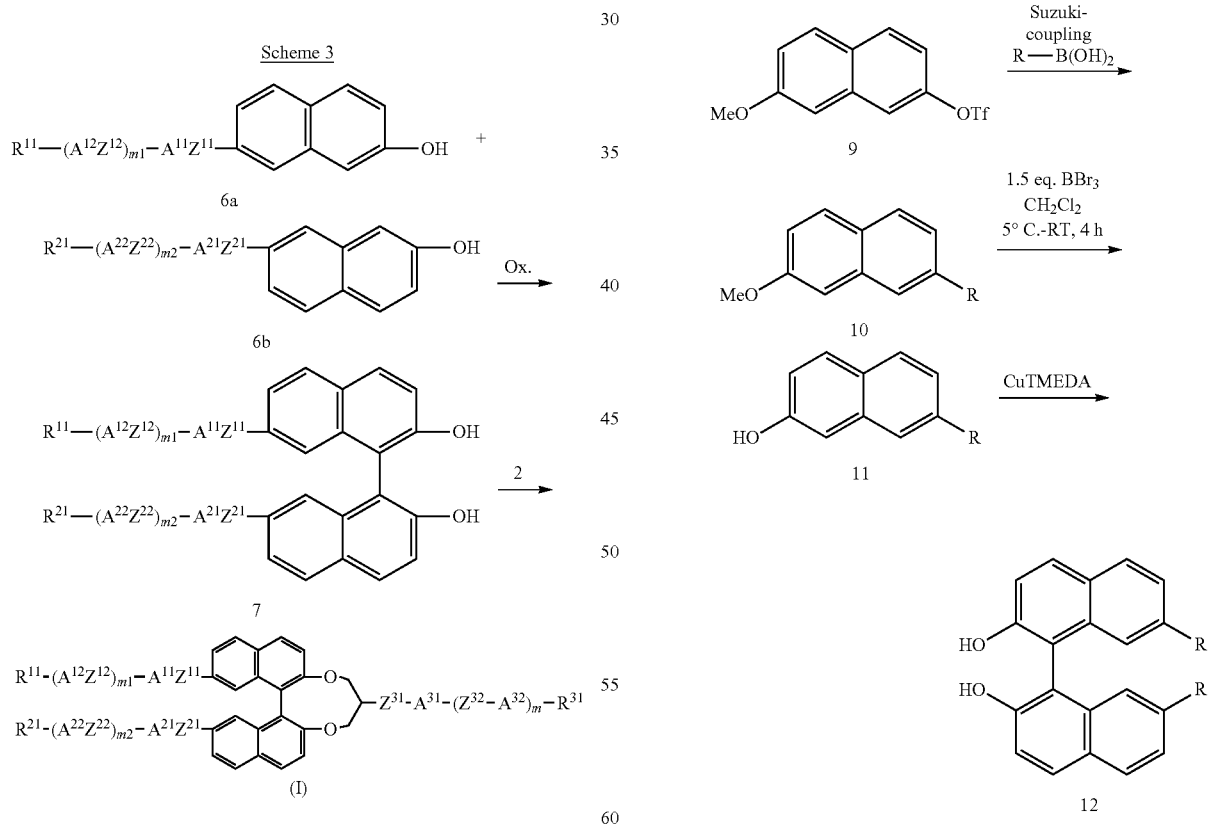

The synthesis shown in scheme 3 is also preferred for compounds where $R^{21}-(A^{22}Z^{22})_{m2}A^{21}-$ in formula I is the same as $R^{11}-(A^{12}Z^{12})_{m1}A^{11}-$. A preferred method for the oxidative coupling (e.g. 6a/6b to give 7) using Cu-TMEDA is published in M. Noji et al., *Tetrahedron Lett.* 1994, 35, 7983-7984.

The racemic BINOL 12 can be resolved by chiral HPLC or by crystallisation of diastereomeric salts or esters using chiral amines or acids known to the skilled person.

An alternative, similar pathway is exemplified in Scheme 5.

Scheme 5
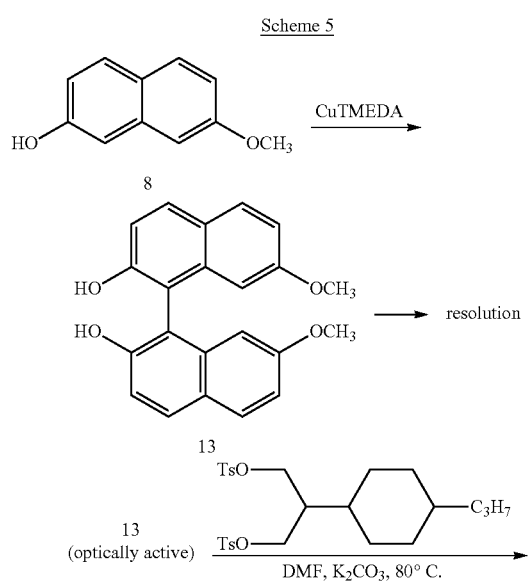
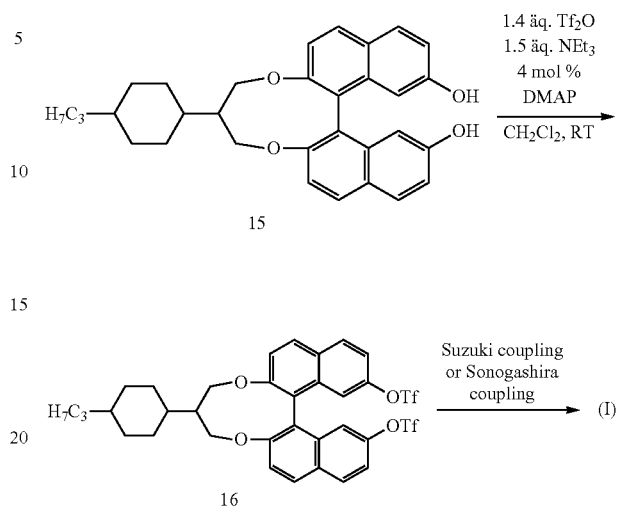
The synthetic pathway towards compound 15 is also generally applicable for the synthesis of ethers, esters and difluoromethyl ethers, using standard transformation described in the literature and as illustrated by the examples in scheme 6.
Scheme 6
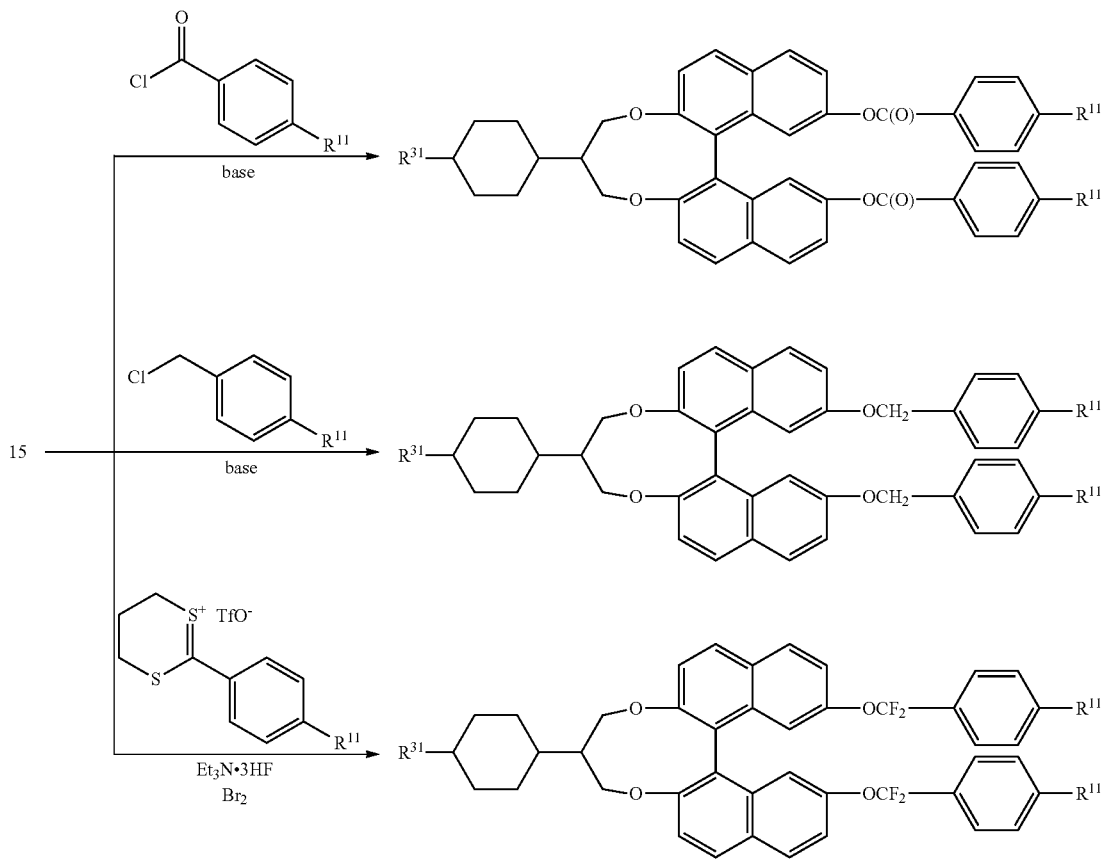

In another preferred embodiment, compounds of formula I are prepared by acetalisation of BINOL derivatives using a method described by M. Zhang and G. B. Schuster, J. Am. Chem. Soc. 1994, 116, 4852-4857. This transformation is exemplified in Scheme 7. Unsubstituted acetals are preferably synthesized using diiodomethane (scheme 8; see also for example A. Minatti, K. H. Dötz, Tetrahedron: Asymmetry 16 (2005) 3256-3267)

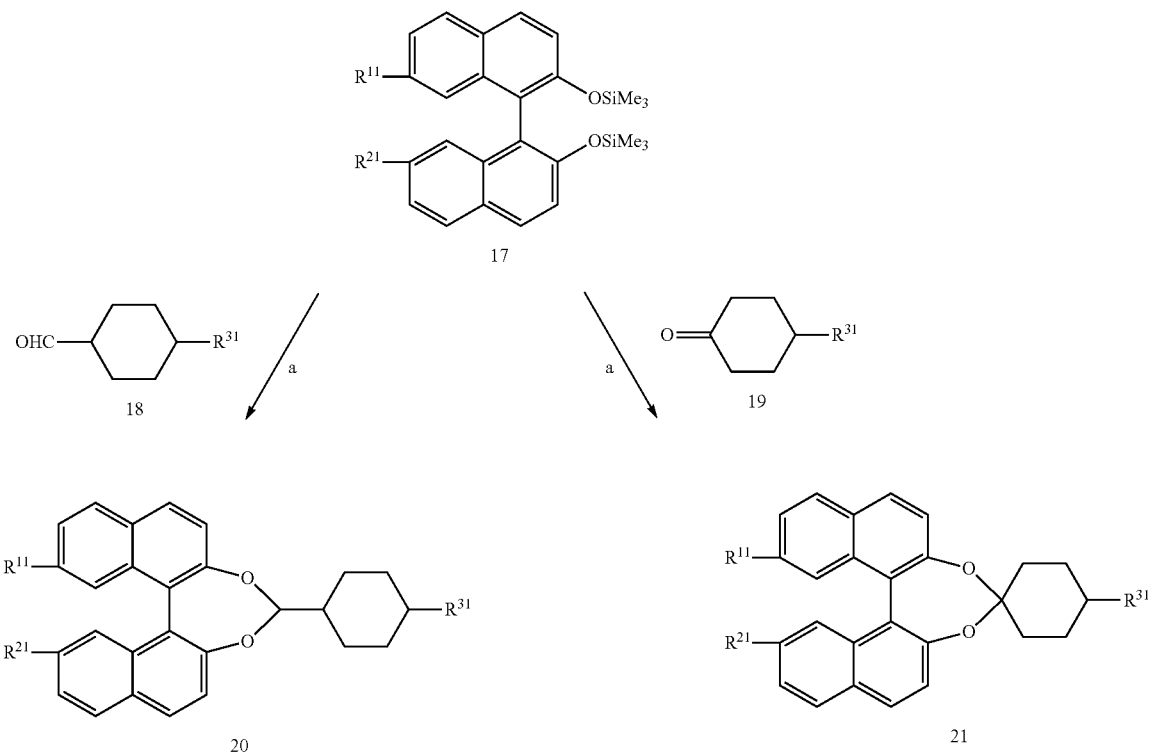

a) 1. $CH_2Cl_2$, cat $Me_3SiOTf$; −78° C.→RT; 2. pyridine

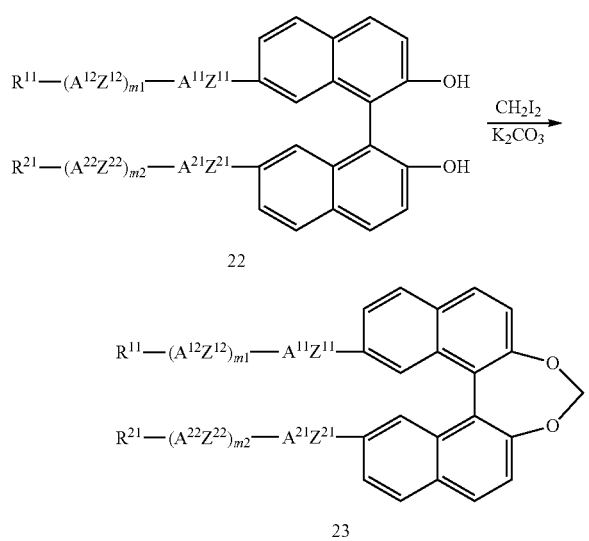

Another object of the present invention are intermediates for the synthesis of compounds of formula I.

Yet another object of the present invention is a process where a compound of formula 22 of scheme 8, where the occurring groups are defined as indicated above for formula I, is transformed into a compound of formula I by alkylation or acetalisation.

In a preferred embodiment, compounds of formula I are prepared from compounds 7 (scheme 3) by etherification according to the procedure described in scheme 1.

The chiral compounds of formula I can be used in a liquid crystal mixture for displays exhibiting a helically twisted molecular structure of the liquid crystal matrix like, for example, Blue Phase displays, preferably containing polymer stabilised blue phase liquid crystals; TN displays of the active or passive matrix type, STN, phase-change, guest-host, ferroelectric or cholesteric displays like SSCT (surface stabilized cholesteric texture) or PSCT (polymer stabilized cholesteric texture).

Thus, another object of the invention is a liquid crystal mixture, in particular a chiral smectic or cholesteric liquid crystal mixture, comprising at least one chiral compound of formula I. Particularly preferred cholesteric mixtures exhibit a Blue Phase at room temperature.

Yet another object of the invention is a liquid crystal display comprising a liquid crystal medium containing at least one chiral compound of formula I.

The chiral compounds of formula I are characterized by high values of the HTP. This enables the preparation of liquid crystal mixtures with a high helical twist, i.e. a low pitch, or the double twist structure characteristic for the Blue Phase, by using only low amounts of chiral compounds of formula I. This is a considerable advantage, as it is often observed that the addition of high amounts of chiral dopants to a liquid crystal mixture negatively affects its liquid crystal phase behaviour and electrooptical properties, such as the dielectric anisotropy, the viscosity or the clearing point. Thus, by using chiral compounds of formula I in a liquid crystal mixture or display its properties are altered only to a minor extent, compared to prior art dopants, resulting for example in a lower threshold voltage and faster switching times of the display.

The chiral compounds of formula I are further characterized by a high solubility in a liquid crystal host mixture. Undesired spontaneous crystallization at low temperatures is reduced, and the operating temperature range of the mixture can be broadened. The use of a second dopant, which is often added to avoid crystallization, can thus be avoided.

A particularly preferred embodiment of the present invention therefore relates to a liquid crystal mixture comprising only one chiral compound, which is a compound of formula I, and to a display comprising such a mixture.

The chiral compounds of formula I also show a low temperature dependence of the HTP when added to a liquid crystal host mixture. They are thus useful as chiral dopants for liquid crystal mixtures and displays with a low temperature dependence of the pitch.

A liquid crystal mixture according to the invention comprises preferably 0.1 to 20%, in particular 1 to 15% and very particularly preferably 2 to 10% by weight of chiral compounds of formula I. It preferably comprises 1, 2 or 3 chiral compounds of formula I.

The compounds of formula I are especially suitable for use in blue phase liquid crystal mixtures for displays disclosed in WO 2004/046805.

It was found that when using chiral compounds of formula I as dopants in polymer stabilised Blue Phase liquid crystal media, for Blue Phase displays, they exhibit good solubility in the nematic host mixture and induce a high helical twist with low temperature dependence of the helical pitch and the reflection wavelength. Blue Phase mixtures with low temperature dependence of the reflection wavelength can be achieved even by using only one chiral dopant according to formula I, preferably in low amounts. This is a considerable advantage over prior art, where high amounts of dopants are needed, and where it is often necessary to use two or more dopants with opposite temperature dependence of the helical twist (e.g. one with positive temperature dependence and one with negative temperature dependence) to achieve good temperature compensation of the reflection wavelength.

Thus, a particularly preferred embodiment of the present invention relates to a liquid crystal medium exhibiting a Blue Phase, in particular for use in Blue Phase displays, particularly preferably a polymer stabilised Blue Phase display, comprising one chiral dopant, which is a compound of formula I, preferably in an amount of 15% or less, in particular 10% or less, very preferably 5% or less.

For the applications described above the liquid crystal mixture preferably contains a chiral component which contains at least one chiral compound of formula I, and a nematic component comprising one or more nematic or nematogenic compounds.

Preferably the liquid crystal mixture consists of 2 to 25, preferably 3 to 15 compounds, at least one of which is a chiral compound of formula I. The other compounds, forming the nematic component, are preferably low molecular weight liquid crystal compounds selected from nematic or nematogenic substances, for example from the known classes of the azoxybenzenes, benzylidene-anilines, biphenyls, terphenyls, phenyl or cyclohexyl benzoates, phenyl or cyclohexyl esters of cyclohehexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclo-hexylpyrimidines, phenyl- or cyclohexylpyridines, phenyl- or cyclo-hexylpyridazines, phenyl- or cyclohexyldioxanes, phenyl- or cyclohexyl-1,3-dithianes, 1,2-diphenyl-ethanes, 1,2-dicyclohexylethanes, 1-phenyl-2-cyclohexylethanes, 1-cyclohexyl-2-(4-phenylcyclohexyl)-ethanes, 1-cyclohexyl-2-biphenyl-ethanes, 1-phenyl2-cyclohexyl-phenylethanes, optionally halogenated stilbenes, benzyl phenyl ether, tolanes, substituted cinnamic acids and further classes of nematic or nematogenic substances. The 1,4-phenylene groups in these compounds may also be laterally mono- or difluorinated.

The liquid crystal mixture of this preferred embodiment is based on the achiral compounds of this type.

The most important compounds that are possible as components of these liquid crystal mixtures can be characterized by the following formula $$R'-L'-G'-E-R'' \tag{IV}$$

wherein L' and E, which may be identical or different, are in each case, independently from one another, a bivalent radical from the group formed by -Phe-, -Cyc-, -Phe-Phe-, -Phe-Cyc-, -Cyc-Cyc-, -Pyr-, -Dio-, —B-Phe- and —B-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and B is 2-(trans-1,4-cyclohexyl)ethyl, pyrimidine-2,5-diyl, pyridine-2,5-diyl or 1,3-dioxane-2,5-diyl.

G' in these compounds is selected from the following bivalent groups —CH=CH—, —N(O)N—, —CH=CY—, —CH=N(O)—, —C≡C—, —CH$_2$—CH$_2$—, —CO—O—, —CH$_2$—O—, —CF$_2$—O—, —CO—S—, —CH$_2$—S—, —CH=N—, —COO-Phe-COO— or a single bond, with Y being halogen, preferably chlorine, or —CN.

R' and R" are, in each case, independently of one another, alkyl, alkenyl, alkoxy, alkenyloxy, alkanoyloxy, alkoxycarbonyl or alkoxycarbonyloxy with 1 to 18, preferably 3 to 12 C atoms, or alternatively one of R' and R" is F, CF$_3$, OCF$_3$, Cl, NCS or CN.

In most of these compounds R' and R" are, in each case, independently of each another, alkyl, alkenyl or alkoxy with different chain length, wherein the sum of C atoms in nematic media generally is between 2 and 9, preferably between 2 and 7.

Particularly preferred liquid crystal mixtures for Blue Phase displays are known from the state-of-the art and disclosed for example in WO 2015/101405 A1, WO 2014/053204 A1, WO 2014/169985 A1, EP 2 708 587 A1, WO 2013156113 A1, WO 2013034219 A1, EP 2568032 B1 and WO 2012 163470 A1. Preferred mesogenic compounds are exemplified in Table D below.

Furthermore, the compounds of formula I are also especially suitable for use in cholesteric liquid crystal mixtures for cholesteric displays, in particular SSCT or PSCT displays. Cholesteric displays are described for example in WO 92/19695, WO 93/23496, U.S. Pat. Nos. 5,453,863 and 5,493,430.

Many of these compounds or mixtures thereof are commercially available. All of these compounds are either known or can be prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not mentioned here.

Polymerizable compounds of formula I or polymerizable liquid crystal mixtures comprising one or more compounds of formula I are useful for the preparation of polymerizable mixtures, which can be used for example in polymer stabilized liquid crystal displays, such as PSCT (polymer stabilized cholesteric texture) and anisotropic polymer gels, which can be used for example in scattering type displays. Anisotropic polymer gels and displays comprising them are disclosed for example in DE 195 04 224 and GB 2 279 659.

The chiral compounds of formula I and polymerizable liquid crystal mixtures comprising them are particularly useful for the preparation of anisotropic polymer films with helically twisted molecular structure with uniform planar orientation, i.e. wherein the helical axis is oriented perpendicular to the plane of the film.

For example, oriented cholesteric polymer films can be used as broad waveband reflective polarizers like for example described in EP 0 606 940, as color filters, for security markings, or for the preparation of liquid crystal pigments for decorative or security uses.

For the preparation of anisotropic polymer gels or oriented polymer films, the liquid crystal mixture should comprise at least one polymerizable compound, which can be a compound of formula I or an additional polymerizable mesogenic or liquid crystalline compound.

Thus, another object of the invention are polymerizable liquid crystal mixtures comprising at least one chiral compound of formula I.

Examples of suitable polymerizable mesogenic compounds that can be used as components of the polymerizable liquid crystal mixture, are disclosed for example in WO 93/22397; EP 0 261 712; DE 195 04224; WO 95/22586 and WO 97/00600. The compounds disclosed in these documents, however, are to be regarded merely as examples that shall not limit the scope of this invention.

Preferably the polymerizable liquid crystal mixture comprises at least one polymerizable mesogenic compound having one polymerizable functional group and at least one polymerizable mesogenic compound having two or more polymerizable functional groups.

Examples of especially useful monoreactive chiral and achiral polymerizable mesogenic compounds are shown in the following list of compounds, which should, however, be taken only as illustrative and is in no way intended to restrict, but instead to explain the present invention:

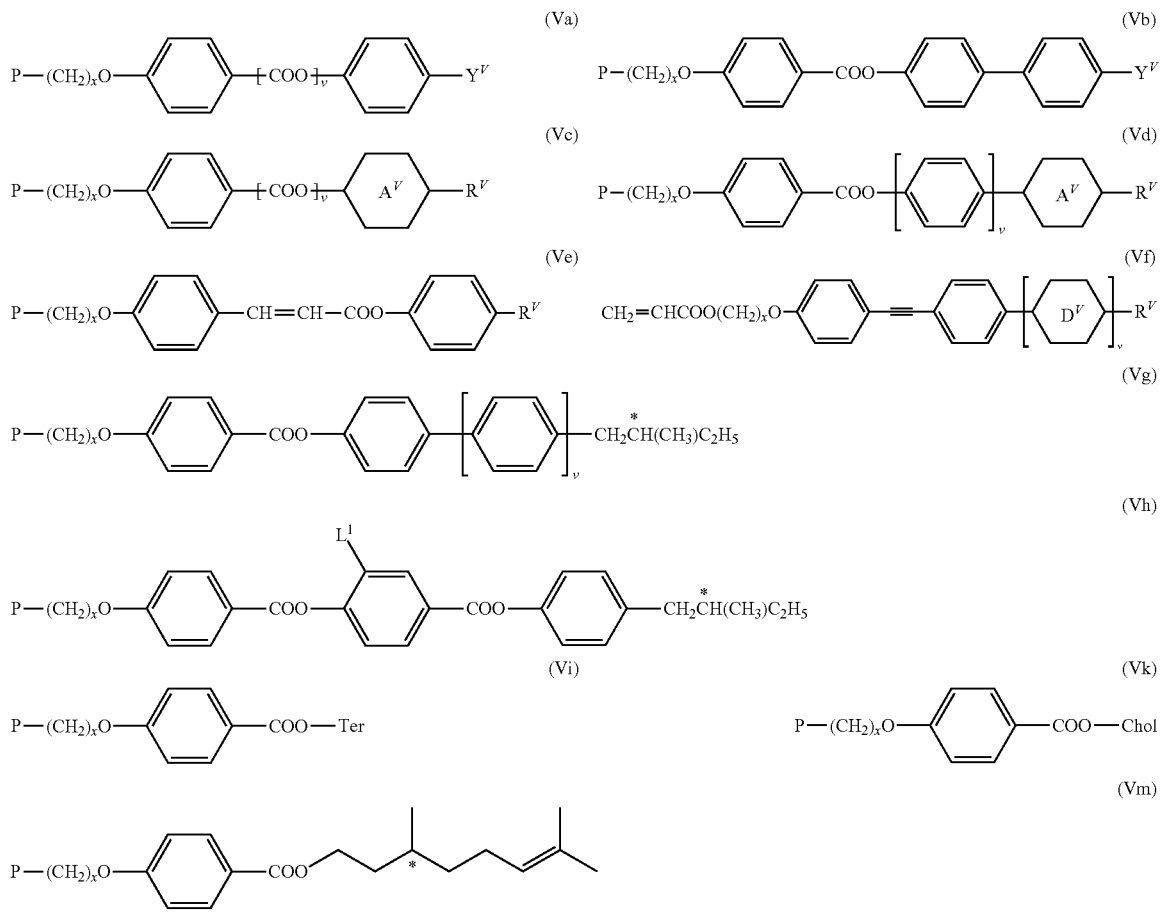

wherein, P has one of the meanings given above, x is an integer from 1 to 12, $A^V$ and $D^V$ are 1,4-phenylene or 1,4-cyclohexylene, v is 0 or 1, $Y^V$ is a polar group, $R^V$ is a non-polar alkyl or alkoxy group, Ter is a terpenoid radical like e.g. menthyl, Chol is a cholesteryl group, and $L^1$ and $L^2$ are each independently H, F, Cl, CN, OH, $NO_2$ or an optionally halogenated alkyl, alkoxy or carbonyl group with 1 to 7 C atoms.

The polar group $Y^V$ is preferably CN, $NO_2$, halogen, $OCH_3$, OCN, SCN, $COR^5$, $COOR^5$ or a mono-oligo- or polyfluorinated alkyl or alkoxy group with 1 to 4 C atoms. $R^5$ is optionally fluorinated alkyl with 1 to 4, preferably 1 to 3 C atoms. Especially preferably the polar group $Y^V$ is selected of F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular F, Cl, CN, $OCH_3$ and $OCF_3$.

The non-polar group $R^V$ is preferably an alkyl group with 1 or more, preferably 1 to 15 C atoms or an alkoxy group with 2 or more, preferably 2 to 15 C atoms.

Examples of useful direactive chiral and achiral polymerizable mesogenic compounds are shown in the following list of compounds, which should, however, be taken only as illustrative and is in no way intended to restrict, but instead to explain the present invention wherein P, x, v, $D^V$, $L^1$ and $L^2$ have one of the meanings given above and y is an integer from 1 to 12 the same as or different from x.

A polymerizable liquid crystal material according to the first preferred embodiment as described above comprises one or more chiral dopants which themselves do not necessarily have to show a liquid crystal phase and give good planar alignment themselves, in particular non-polymerizable chiral dopants.

The mono- and difunctional polymerizable mesogenic compounds of above formulae V and VI can be prepared by methods which are known per se and which are described in the documents cited above and, for example, in standard works of organic chemistry such as, for example, Houben-Weyl, Methoden der organischen Chemie, Thieme-Verlag, Stuttgart.

In a preferred embodiment of the invention the polymerizable liquid crystal mixtures comprise at least one inventive chiral compound, at least one monofunctional compound of formulae Va-Vm and at least one bifunctional polymerizable compound of formulae VIa-VIe.

In another preferred embodiment the polymerizable liquid crystal mixtures comprise at least one inventive chiral compound and at least two monofunctional compounds of formulae Va-Vm.

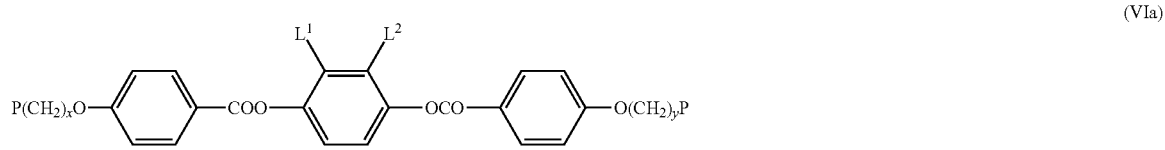
(VIa)

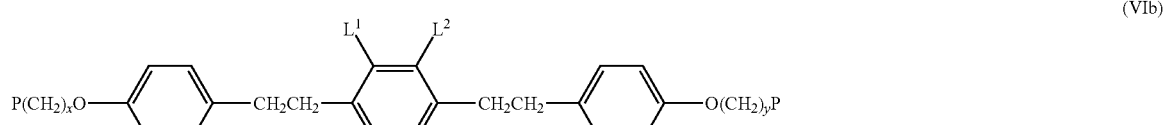
(VIb)

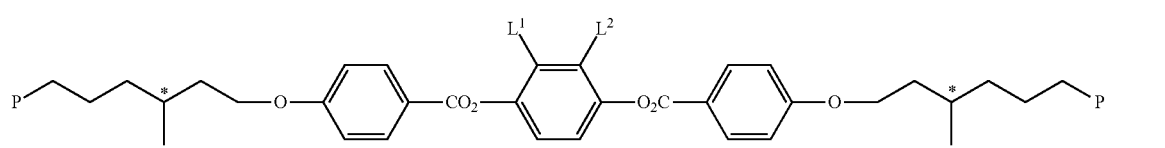
(VIc)

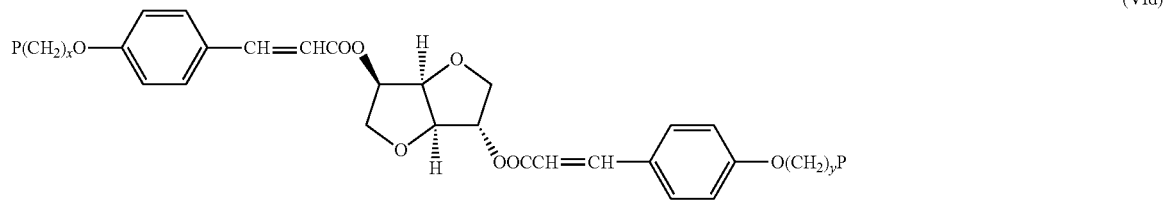
(VId)

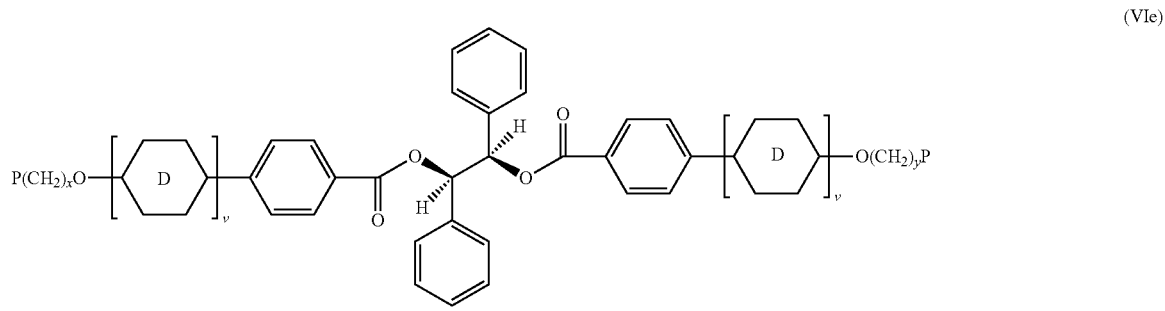
(VIe)

Another object of the invention is an anisotropic polymer film with an oriented chiral liquid crystalline phase obtainable by (co)polymerizing a liquid crystal mixture comprising at least one chiral compound of formula I and at least one polymerizable mesogenic compound preferably selected of formula Va-Vm and VIa-VIe and/or at least one polymerizable chiral compound of formula I.

To prepare anisotropic polymer film with a chiral liquid crystalline phase with uniform orientation the polymerizable liquid crystal can be coated onto a substrate, aligned and polymerized in situ, for example by exposure to heat or actinic radiation, to fix the uniform orientation of the liquid crystal molecules. Alignment and curing are carried out in the liquid crystalline phase of the mixture.

Actinic radiation means irradiation with light, like UV light, IR light or visible light, irradiation with X-rays or gamma rays or irradiation with high energy particles, such as ions or electrons. As a source for actinic radiation for example a single UV lamp or a set of UV lamps can be used. Another possible source for actinic radiation is a laser, like e.g. a UV laser, an IR laser or a visible laser.

For example, when polymerizing by means of UV light, a photoinitiator can be used that decomposes under UV irradiation to produce free radicals or ions that start the polymerization reaction.

It is also possible to use a cationic photoinitiator, when curing reactive mesogens with for example vinyl and epoxide reactive groups, that photocures with cations instead of free radicals.

As a photoinitiator for radical polymerization for example the commercially available Irgacure 651, Irgacure 184, Darocure 1173 or Darocure 4205 (all from Ciba Geigy AG) can be used, whereas in case of cationic photopolymerization the commercially available UVI 6974 (Union Carbide) can be used.

Preferably the polymerizable liquid crystal mixture comprising polymerizable chiral compounds of formula I and/or polymerizable mesogenic compounds of formulae V and VI additionally comprises 0.01 to 10%, in particular 0.05 to 8%, very preferably 0.1 to 5% by weight of a photoinitiator, especially preferably a UV-photoinitiator.

Polymerization is preferably carried out under an atmosphere of inert gas, preferably under a nitrogen atmosphere.

As a substrate for example a glass or quartz sheet as well as a plastic film or sheet can be used. It is also possible to put a second substrate on top of the coated mixture prior to, during and/or after polymerization. The substrates can be removed after polymerization or not. When using two substrates in case of curing by actinic radiation, at least one substrate has to be transmissive for the actinic radiation used for the polymerization.

Isotropic or birefringent substrates can be used. In case the substrate is not removed from the polymerized film after polymerization, preferably isotropic substrates are used.

Preferably at least one substrate is a plastic substrate such as for example a film of polyester such as polyethyleneterephthalate (PET), of polyvinylalcohol (PVA), polycarbonate (PC) or triacetylcellulose (TAC), especially preferably a PET film or a TAC film. As a birefringent substrate for example an uniaxially stretched plastic film can be used. For example PET films are commercially available from ICI Corp. under the trade name Melinex.

Preferably the polymerizable liquid crystal mixture I is coated as a thin layer on a substrate or between substrate, and aligned in its chiral mesophase into planar orientation, wherein the axis of the molecular helix extends transversely to the layer.

Planar orientation can be achieved for example by shearing the mixture, e.g. by means of a doctor blade. It is also possible to put a second substrate on top of the coated material. In this case, the shearing caused by putting together the two substrates is sufficient to give good alignment. Alternatively it is possible to apply an alignment layer, for example a layer of rubbed polyimide or sputtered $SiO_x$, on top of at least one of the substrates, or to apply an electric or magnetic field to the coated mixture, in order to induce or enhance planar alignment. In a preferred method planar alignment is induced or enhanced by addition of one or more surface-active compounds to the polymerizable mixture.

In some cases it is of advantage to apply a second substrate not only to aid alignment of the polymerizable mixture but also to exclude oxygen that may inhibit the polymerization. Alternatively the curing can be carried out under an atmosphere of inert gas. However, curing in air is also possible using suitable photoinitiators and high lamp power. When using a cationic photoinitiator oxygen exclusion most often is not needed, but water should be excluded.

A detailed description of the in situ polymerization of polymerizable mesogenic compounds can be found in D. J. Broer et al., Makromolekulare Chemie 190, 2255 (1989).

A polymerizable liquid crystal mixture for the preparation of anisotropic polymer films comprises preferably 0.1 to 35%, in particular 0.5 to 15% and very particularly preferably 0.5 to 5% by weight of one or more polymerizable chiral compounds of formula I.

Polymerizable liquid crystal mixtures are preferred that comprise 1 to 3 chiral compounds of formula I.

The inventive polymerizable liquid crystal mixtures can additionally comprise one or more other suitable components, such as, for example, catalysts, sensitizers, stabilizers, co-reacting monomers or surface-active compounds.

In a preferred embodiment of the invention, the inventive polymerizable liquid crystal mixture comprises a stabilizer that is used to prevent undesired spontaneous polymerization for example during storage of the composition. As stabilizers in principal all compounds can be used that are known to the skilled in the art for this purpose. These compounds are commercially available in a broad variety. Typical examples for stabilizers are 4-ethoxyphenol or butylated hydroxytoluene (BHT).

It is also possible, in order to increase crosslinking of the polymers, to add up to 20% of a non mesogenic compound with two or more polymerizable functional groups to the polymerizable composition alternatively or additionally to the multifunctional polymerizable mesogenic compounds.

Typical examples for difunctional non mesogenic monomers are alkyldiacrylates or alkyldimethacrylates with alkyl groups of 1 to 20 C atoms. Typical examples for non mesogenic monomers with more than two polymerizable groups are trimethylpropanetrimethacrylate or pentaerythritoltetraacrylate.

Polymerization of inventive compositions comprising compounds with only one polymerizable functional group leads to linear polymers, whereas in the presence of compounds with more than one polymerizable functional group crosslinked polymers are obtained.

For the preparation of anisotropic polymer gels, the liquid crystal mixtures can be polymerized in situ as described above, however, in this case alignment of the polymerizable mixture is not necessary.

The inventive chiral compounds of formula I and liquid crystal mixtures, liquid crystal polymers or liquid crystal pigments comprising them are also suitable for use in cosmetic and pharmaceutical compositions, for example for coloured make-up as described in EP 815 826 or as UV-filters for the protection of human skin or hair, in particular protection against UV-A and UV-B-radiation, as described for example in DE 196 29 761 or EP 1 038 941. The inventive dopants have a high HTP, therefore only small amounts are needed to yield a short pitch, resulting in a material that shows reflection in the UV range and is suitable as UV-filter.

A liquid crystal mixture, liquid crystal polymer or liquid crystal pigment comprising a chiral compound of formula I and reflecting UV light, in particular of a wavelength of 200 to 400 nm, is another object of the invention. Another object is a cosmetic composition, in particular a cosmetic or pharmaceutical composition for protection of human skin or hair, comprising as UV-filter a liquid crystal mixture, liquid crystal polymer or liquid crystal pigment comprising a chiral compound of formula I and reflecting UV light, in particular in a wavelength range of 200-440 nm, especially 280-400 nm, 200-230 nm (UV-C) and 280-330 nm (UV-B).

In the foregoing and in the following examples, unless otherwise indicated, all temperatures are set forth uncorrected in degrees Celsius and all parts and percentages are by weight.

In the chemicals structures above and below, all cyclohexane, oxane or dioxane rings preferably have 1,4-trans-configuration.

In the present invention and especially in the following examples, the structures of the mesogenic compounds are indicated by means of abbreviations, also called acronyms. In these acronyms, the chemical formulae are abbreviated as follows using Tables A to C below. All groups $C_nH_{2n+1}$, $C_mH_{2m+1}$ and $C_lH_{2l+1}$ or $C_nH_{2n-1}$, $C_mH_{2m-1}$ and $C_lH_{2l-1}$ denote straight-chain alkyl or alkenyl, preferably 1E-alkenyl, each having n, m and l C atoms respectively. Table A lists the codes used for the ring elements of the core structures of the compounds, while Table B shows the linking groups. Table C gives the meanings of the codes for the left-hand or right-hand end groups. The acronyms are composed of the codes for the ring elements with optional linking groups, followed by a first hyphen and the codes for the left-hand end group, and a second hyphen and the codes for the right-hand end group. Table D shows illustrative structures of compounds together with their respective abbreviations.

TABLE A

| Ring elements | | | |
|---|---|---|---|
| C |  | P | 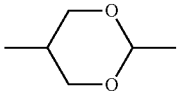 |
| D | 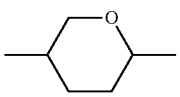 | DI | 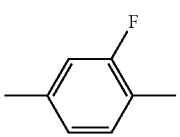 |
| A | 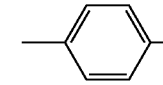 | AI | 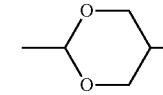 |
| G | 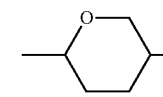 | GI | 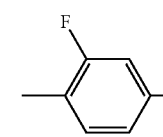 |

TABLE A-continued

| Ring elements | | | |
|---|---|---|---|
| U | 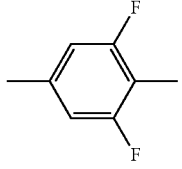 | UI | 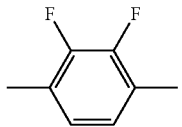 |
| Y | 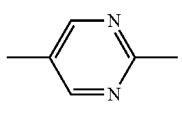 | | |
| M | 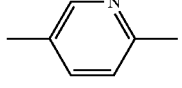 | MI | 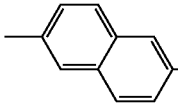 |
| N | 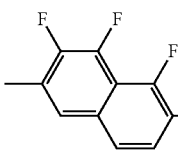 | NI | 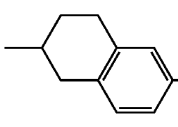 |
| Np | 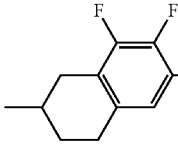 | dH | 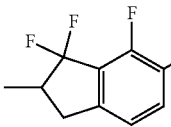 |
| N3f | 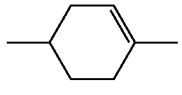 | N3fI | 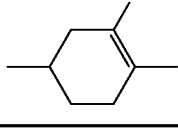 |
| tH | 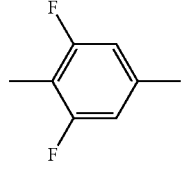 | tHI | 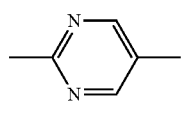 |
| tH2f | 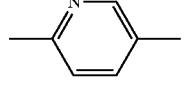 | tH2fI | 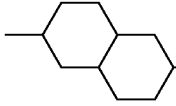 |
| K | 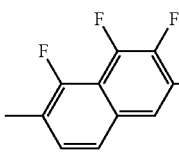 | KI | 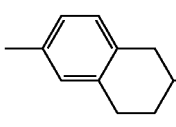 |
| L | 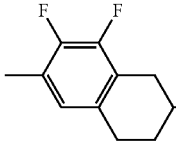 | LI |  |
| F | 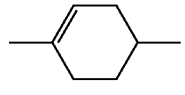 | FI | 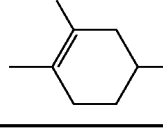 |

TABLE B

| | Linking groups | | |
|---|---|---|---|
| E | —$CH_2CH_2$— | Z | —CO—O— |
| V | —CH=CH— | ZI | —O—CO— |
| X | —CF=CH— | O | —$CH_2$—O— |
| XI | —CH=CF— | OI | —O—$CH_2$— |

TABLE B-continued

| | Linking groups | | |
|---|---|---|---|
| B | —CF=CF— | Q | —$CF_2$—O— |
| T | —C≡C— | QI | —O—$CF_2$— |
| W | —$CF_2CF_2$— | T | —C≡C— |

TABLE C

| End groups | | | |
|---|---|---|---|
| Left-hand side | | Right-hand side | |
| Use alone | | | |
| -n- | $C_nH_{2n+1}$— | -n | —$C_nH_{2n+1}$ |
| -nO- | $C_nH_{2n+1}$—O— | -On | —O—$C_nH_{2n+1}$ |
| -V- | $CH_2$=CH— | -V | —CH=$CH_2$ |
| -nV- | $C_nH_{2n+1}$—CH=CH— | -nV | —$C_nH_{2n}$—CH=$CH_2$ |
| -Vn- | $CH_2$=CH—$C_nH_{2n+1}$— | -Vn | —CH=CH—$C_nH_{2n+1}$ |
| -nVm- | $C_nH_{2n+1}$—CH=CH—$C_mH_{2m}$— | -nVm | —$C_nH_{2n}$—CH=CH—$C_mH_{2m+1}$ |
| -N- | N≡C— | -N | —C≡N |
| -S- | S=C=N— | -S | —N=C=S |
| -F- | F— | -F | —F |
| -CL- | Cl— | -CL | —Cl |
| -M- | $CFH_2$— | -M | —$CFH_2$ |
| -D- | $CF_2H$— | -D | —$CF_2H$ |
| -T- | $CF_3$— | -T | —$CF_3$ |
| -MO- | $CFH_2O$— | -OM | —$OCFH_2$ |
| -DO- | $CF_2HO$— | -OD | —$OCF_2H$ |
| -TO- | $CF_3O$— | -OT | —$OCF_3$ |
| -FXO- | $CF_2$=CH—O— | -OXF | —O—CH=$CF_2$ |
| -A- | H—C≡C— | -A | —C≡C—H |
| -nA- | $C_nH_{2n+1}$—CH=CH— | -An | —C≡C—$C_nH_{2n+1}$ |
| -NA- | N≡C—C≡C— | -AN | —C≡C—C≡N |
| Use together with one another and/or with others | | | |
| -...A...- | —C≡C— | -...A... | —C≡C— |
| -...V...- | CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —$CF_2CF_2$— | -...W... | —$CF_2CF_2$— | in which n and m each denote integers, and the three dots "..." are place-holders for other abbreviations from this table.

The following table shows illustrative structures together with their respective abbreviations. These are shown in order to illustrate the meaning of the rules for the abbreviations. They furthermore represent compounds which are preferably used.

TABLE D

Illustrative structures

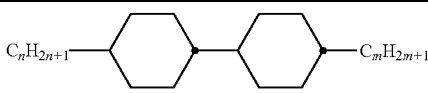

CC-n-m

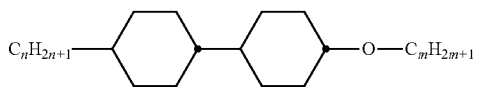

CC-n-Om

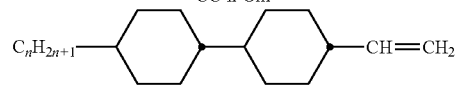

CC-n-V

TABLE D-continued

Illustrative structures $C_nH_{2n+1}$—⬡—⬡—CH=CH—$C_mH_{2m+1}$

CC-n-Vm $C_nH_{2n+1}$—⬡—⬡—$(CH_2)_m$—CH=$CH_2$

CC-n-mV $C_nH_{2n+1}$—⬡—⬡—$(CH_2)_m$—CH=CH—$C_lH_{2l+1}$

CC-n-mVl $H_2C$=CH—⬡—⬡—CH=$CH_2$

CC-V-V $CH_2$=CH—⬡—⬡—$(CH_2)_m$—CH=$CH_2$

CC-V-mV $CH_2$=CH—⬡—⬡—CH=CH—$C_mH_{2m+1}$

CC-V-Vm $CH_2$=CH—$(CH_2)_n$—⬡—⬡—$(CH_2)_m$—CH=$CH_2$

CC-Vn-mV $C_nH_{2n+1}$—CH=CH—⬡—⬡—$(CH_2)_m$—CH=$CH_2$

CC-nV-mV $C_nH_{2n+1}$—CH=CH—⬡—⬡—CH=CH—$C_mH_{2m+1}$

CC-nV-Vm $C_nH_{2n+1}$—⬡—⌬—$C_mH_{2m+1}$

CP-n-m $C_nH_{2n+1}O$—⬡—⌬—$C_mH_{2m+1}$

CP-nO-m

TABLE D-continued

Illustrative structures $C_nH_{2n+1}$—⬡—⌬—$OC_mH_{2m+1}$

CP-n-Om $CH_2$=CH—⬡—⌬—$C_mH_{2m+1}$

CP-V-m $CH_2$=CH—$(CH_2)_n$—⬡—⌬—$C_mH_{2m+1}$

CP-Vn-m $C_nH_{2n+1}$—CH=CH—⬡—⌬—$C_mH_{2m+1}$

CP-nV-m $H_2C$=CH—⬡—⌬—CH=$CH_2$

CP-V-V $CH_2$=CH—⬡—⌬—$(CH_2)_m$—CH=$CH_2$

CP-V-mV $CH_2$=CH—⬡—⌬—CH=CH—$C_mH_{2m+1}$

CP-V-Vm $CH_2$=CH—$(CH_2)_n$—⬡—⌬—$(CH_2)_m$—CH=$CH_2$

CP-Vn-mV $C_nH_{2n+1}$—CH=CH—⬡—⌬—$(CH_2)_m$—CH=$CH_2$

CP-nV-mV $C_nH_{2n+1}$—CH=CH—⬡—⌬—CH=CH—$C_mH_{2m+1}$

CP-nV-Vm $C_nH_{2n+1}$—⌬—⌬—$C_mH_{2m+1}$

PP-n-m

TABLE D-continued
Illustrative structures
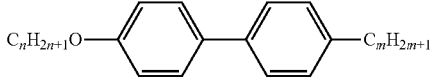
PP-nO-m
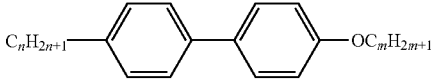
PP-n-Om
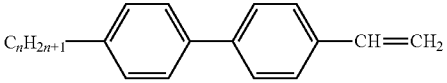
PP-n-V
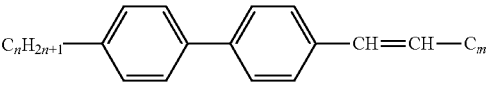
PP-n-Vm
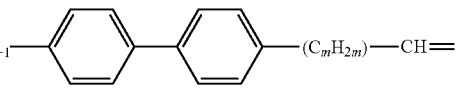
PP-n-mV
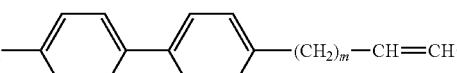
PP-n-mVl
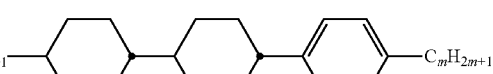
CCP-n-m
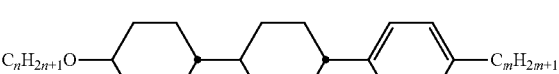
CCP-nO-m
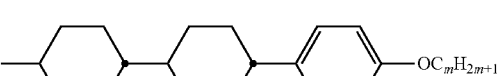
CCP-n-Om
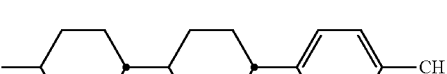
CCP-n-V
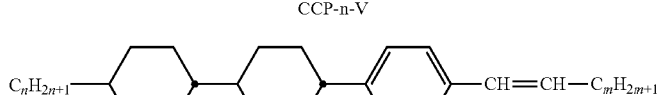
CCP-n-Vm TABLE D-continued
Illustrative structures
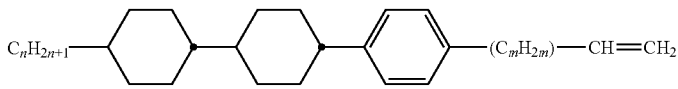
CCP-n-mV
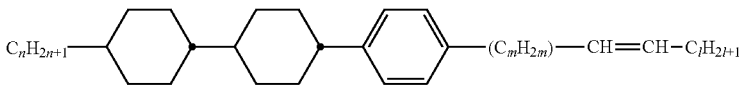
CCP-n-mVI
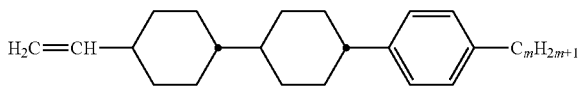
CCP-V-m
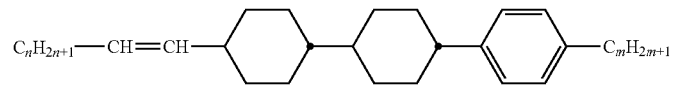
CCP-nV-m
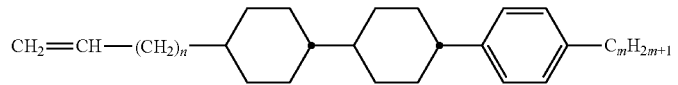
CCP-Vn-m
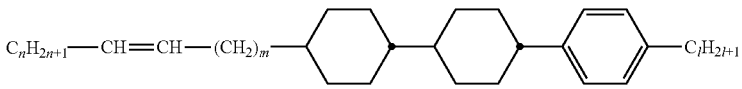
CCP-nVm-I
CCP-n-m
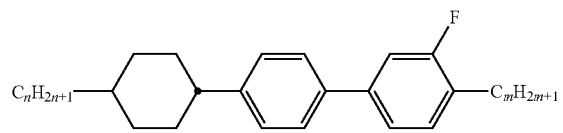
CPG-n-m
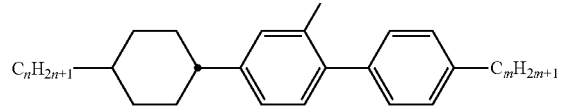
CGP-n-m
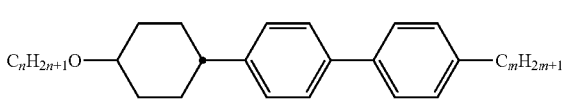
CPP-nO-m
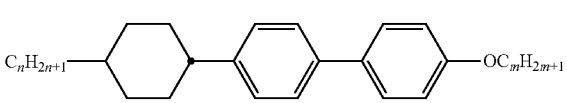
CPP-n-Om TABLE D-continued
Illustrative structures
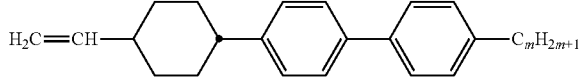
CPP-V-m
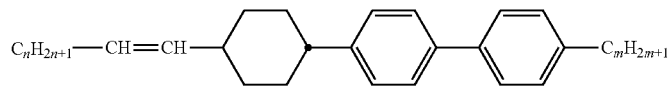
CPP-nV-m
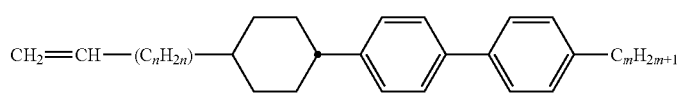
CPP-Vn-m
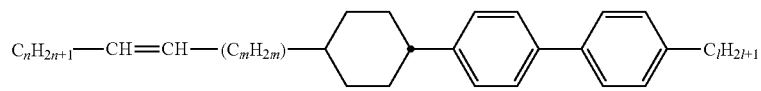
CPP-nVm-l
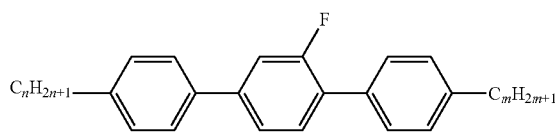
PGP-n-m
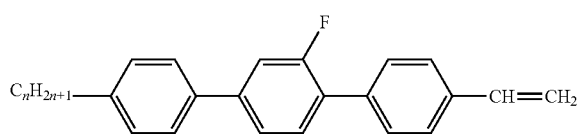
PGP-n-V
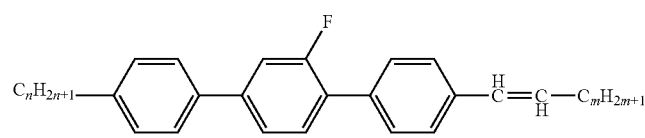
PGP-n-Vm
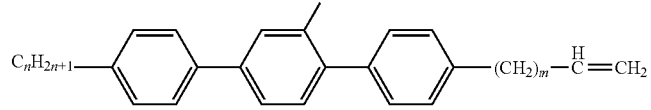
PGP-n-mV
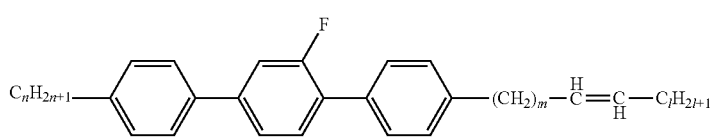
PGP-n-mVl
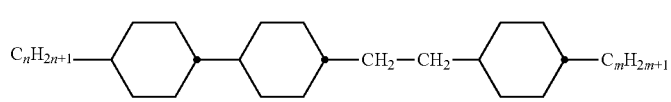
CCEC-n-m TABLE D-continued
Illustrative structures
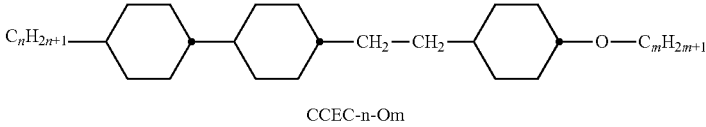
CCEC-n-Om
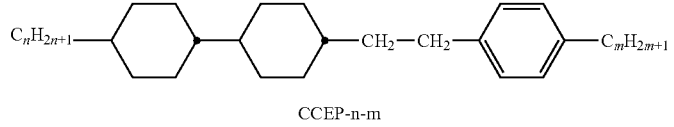
CCEP-n-m
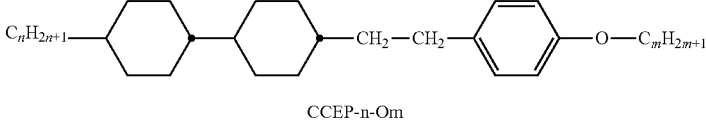
CCEP-n-Om
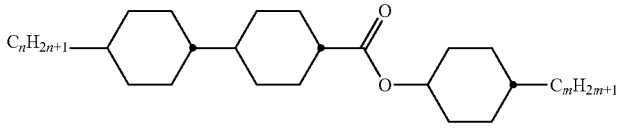
CCZC-n-m
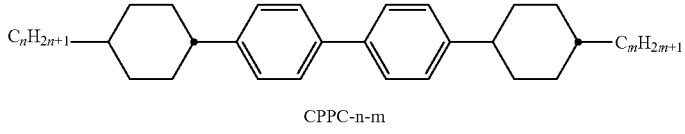
CPPC-n-m
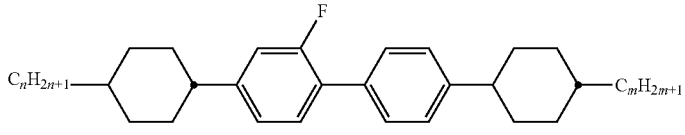
CGPC-n-m
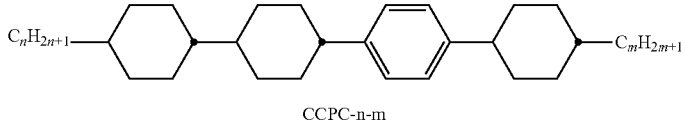
CCPC-n-m
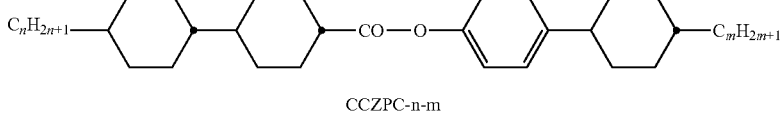
CCZPC-n-m
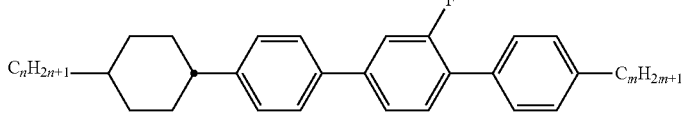
CPGP-n-m
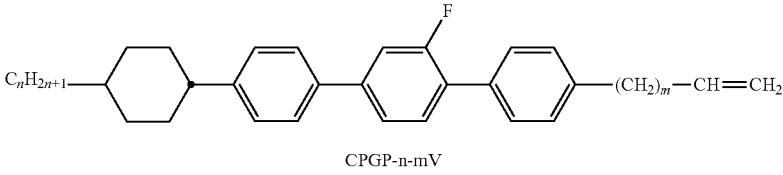
CPGP-n-mV TABLE D-continued

| Illustrative structures |
|---|

CPGP-n-mVI

PGIGP-n-m

CC-n-T

CP-n-F

CP-n-CL

GP-n-F

GP-n-CL

CCP-n-OT

CCG-n-OT

CCP-n-T

TABLE D-continued
Illustrative structures
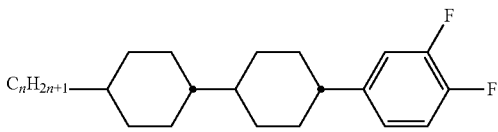
CCG-n-F
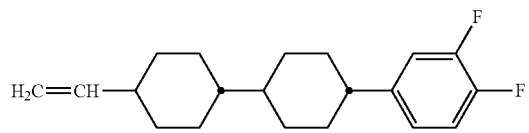
CCG-V-F
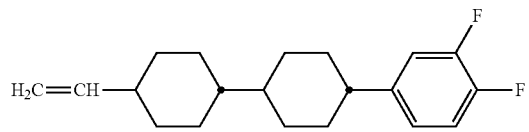
CCG-V-F
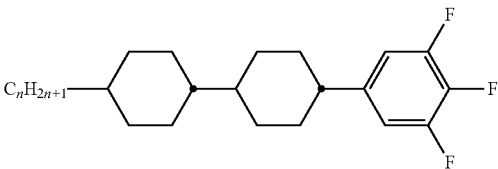
CCU-n-F
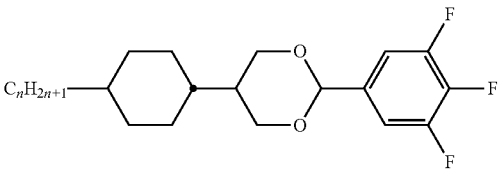
CDU-n-F
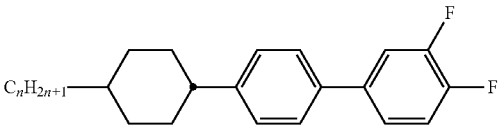
CPG-n-F
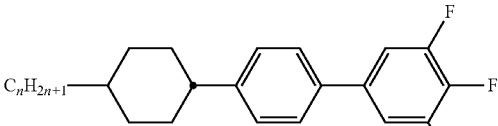
CPU-n-F
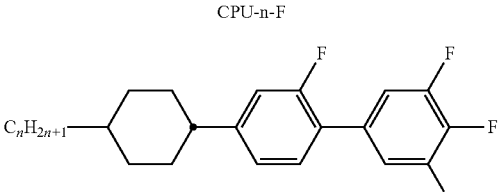
CGU-n-F TABLE D-continued
Illustrative structures
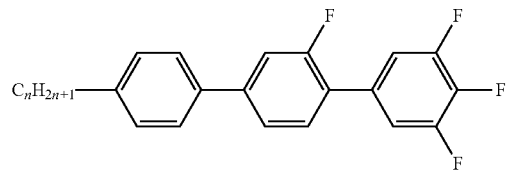
PGU-n-F
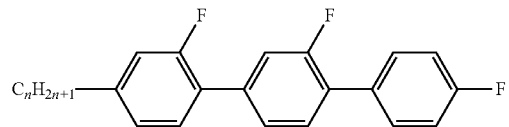
GGP-n-F
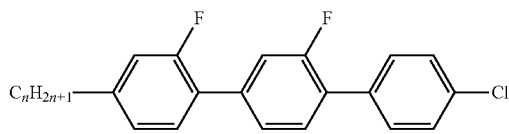
GGP-n-CL
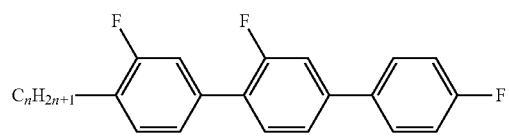
PGIGI-n-F
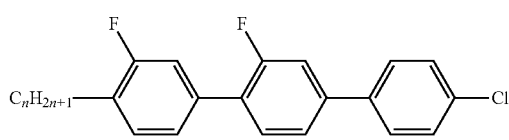
PGIGI-n-CL
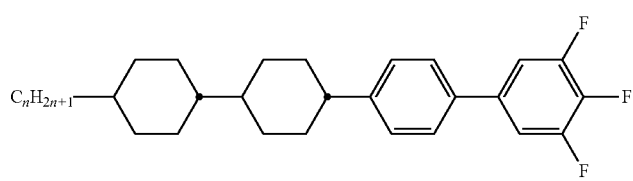
CCPU-n-F
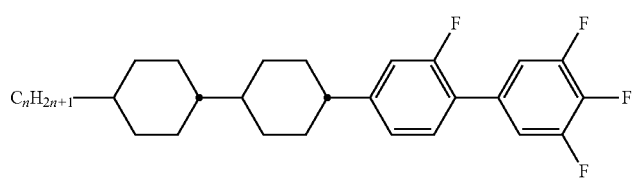
CCGU-n-F
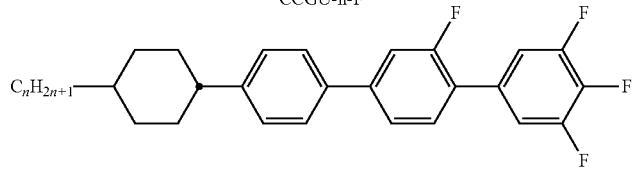
CPGU-n-F TABLE D-continued
Illustrative structures
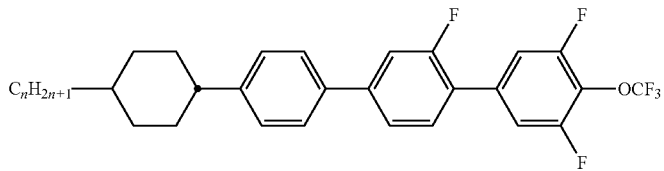
CPGU-n-OT
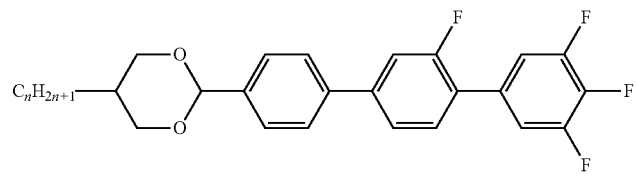
DPGU-n-F
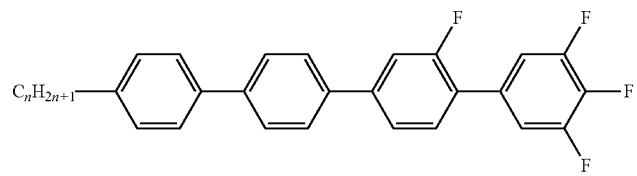
PPGU-n-F
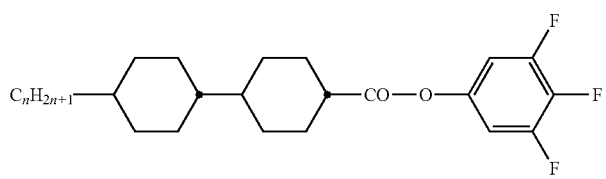
CCZU-n-F
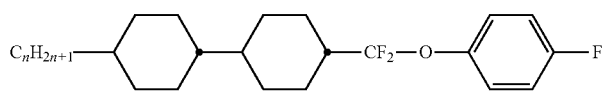
CCQP-n-F
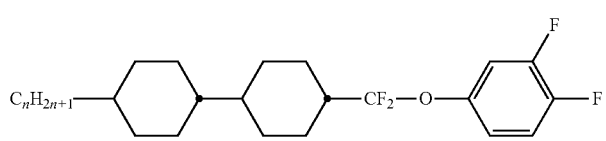
CCQG-n-F
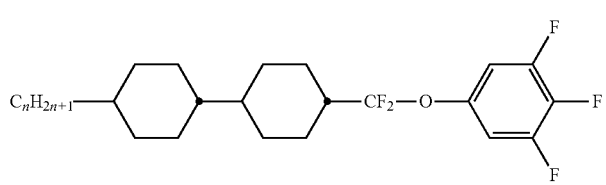
CCQU-n-F
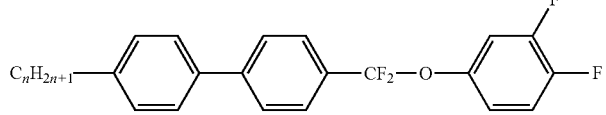
PPQG-n-F TABLE D-continued
Illustrative structures
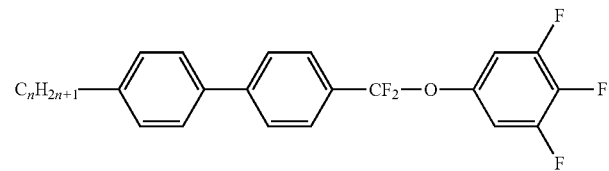
PPQU-n-F
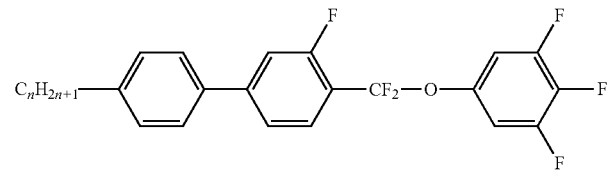
PGQU-n-F
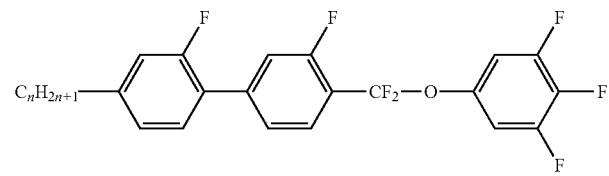
GGQU-n-F
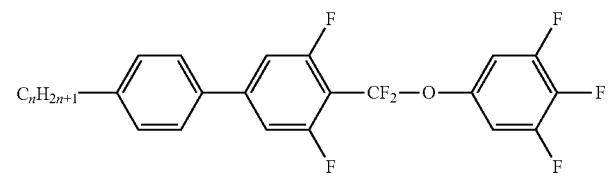
PUQU-n-F
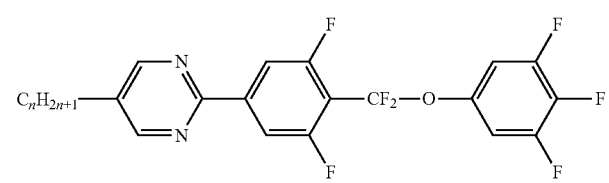
MUQU-n-F
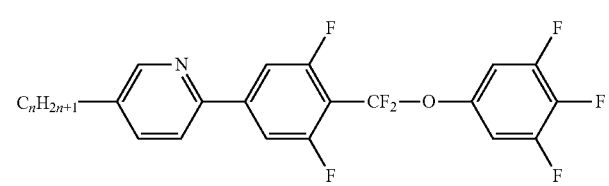
NUQU-n-F
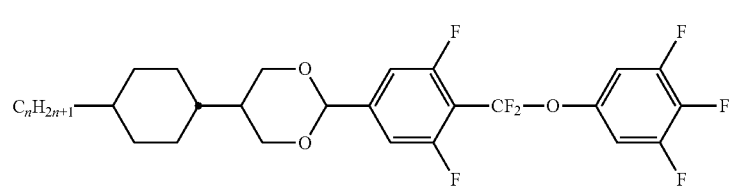
CDUQU-n-F TABLE D-continued
Illustrative structures
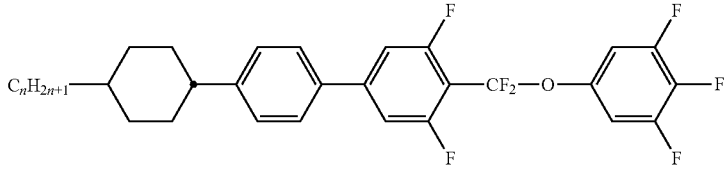
CPUQU-n-F
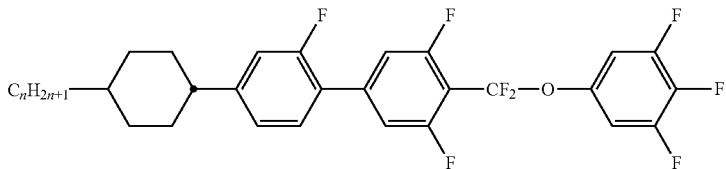
CGUQU-n-F
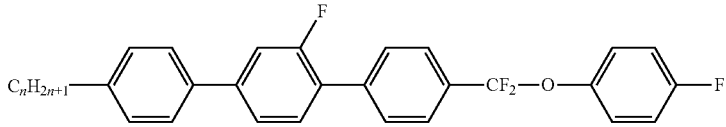
PGPQP-n-F
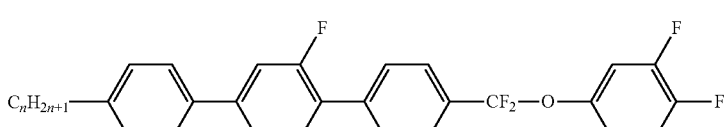
PGPQG-n-F
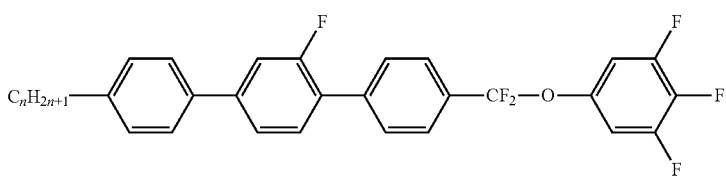
PGPQU-n-F
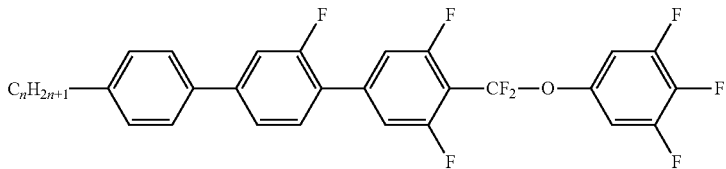
PGUQU-n-F
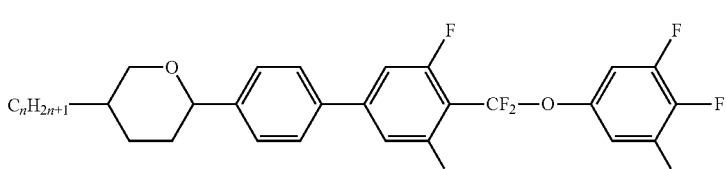
APUQU-n-F TABLE D-continued
Illustrative structures
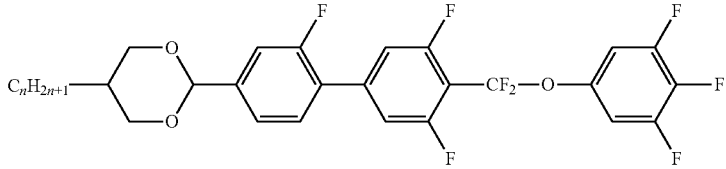
DGUQU-n-F
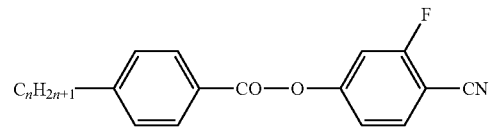
PZG-n-N
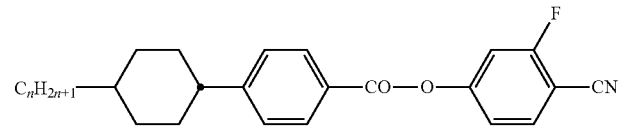
CPZG-n-N
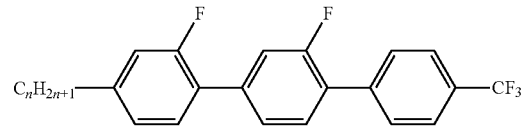
GGP-n-T
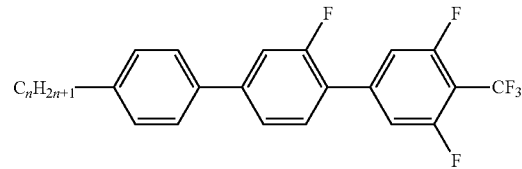
PGU-n-T
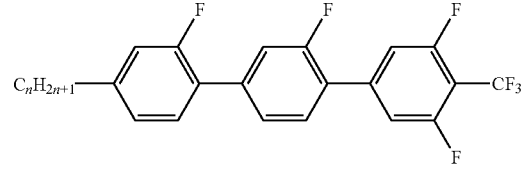
GGU-n-T
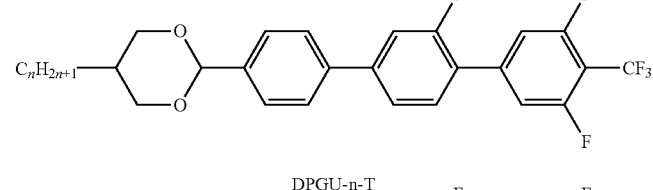
DPGU-n-T
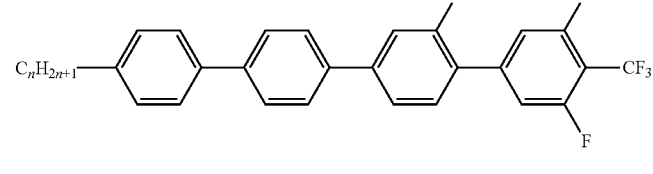
PPGU-n-T TABLE D-continued
Illustrative structures
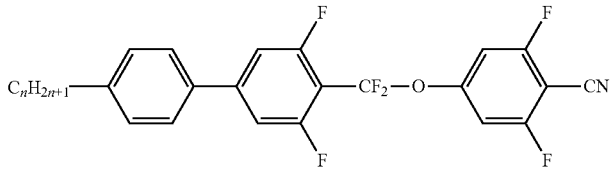
PUQU-n-N
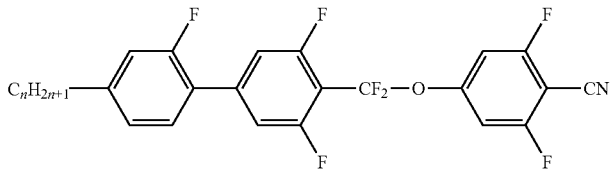
GUQU-n-N
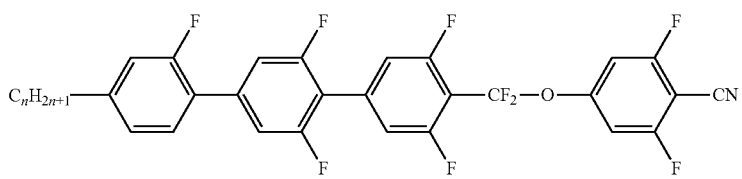
GUUQU-n-N
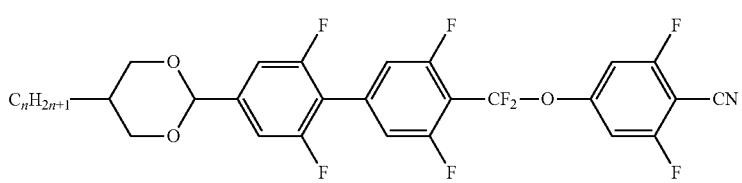
DUUQU-n-N
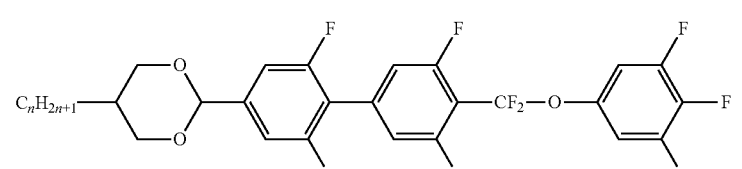
DUUQU-n-F
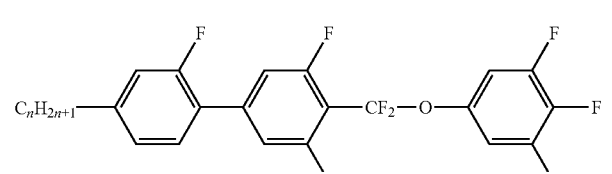
GUQU-n-F
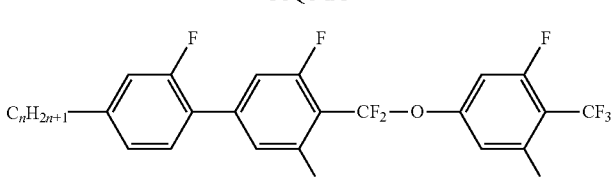
GUQU-n-T TABLE D-continued
Illustrative structures
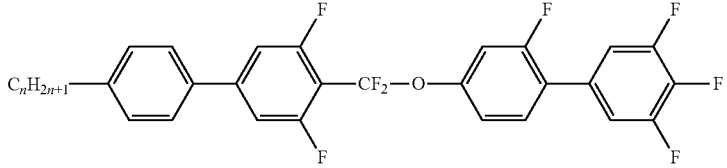
PUQGU-n-F
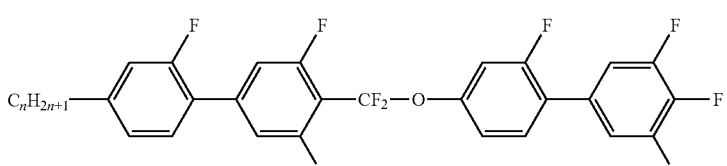
GUQGU-n-F
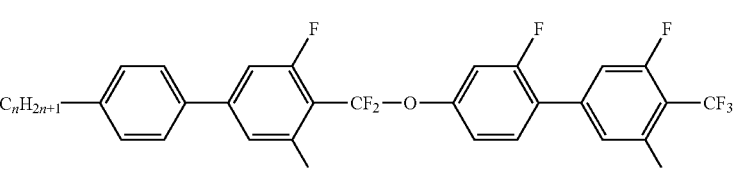
PUQGU-n-T
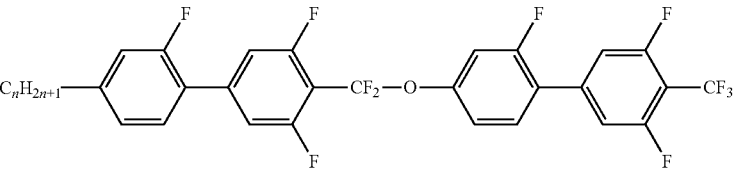
GUQGU-n-T
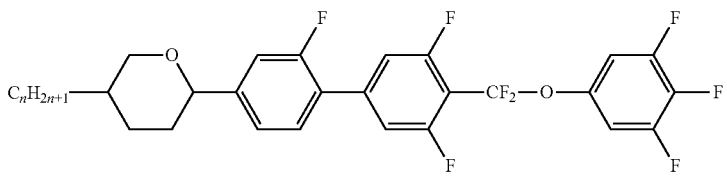
AGUQU-n-F
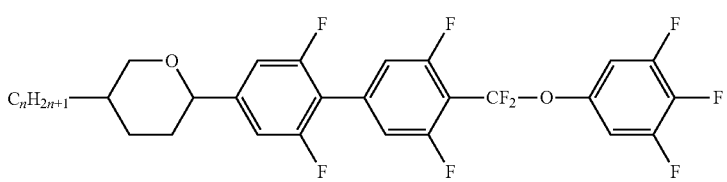
AUUQU-n-F
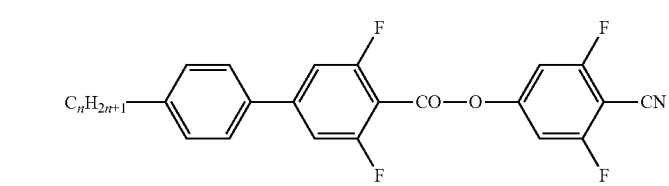
PUZU-n-N TABLE D-continued
Illustrative structures
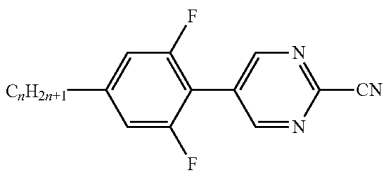
UM-n-N
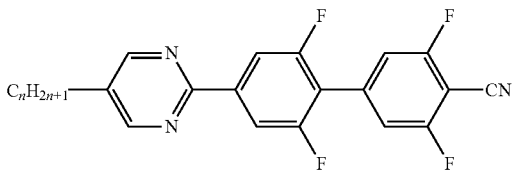
MUU-n-N
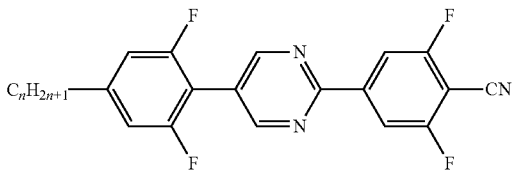
UMU-n-N
in which n, m and l preferably, independently of one another, denote an integer from 1 to 7, preferably from 2 to 6.
The following table, Table E, shows illustrative compounds which can be used as stabiliser in the mesogenic media according to the present invention.
TABLE E
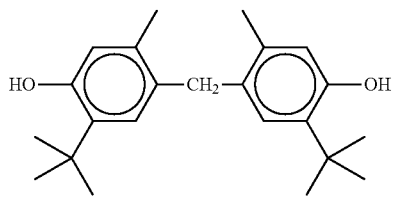
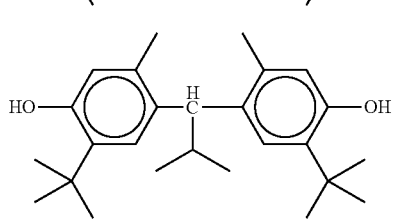
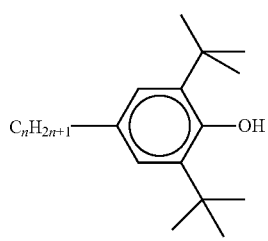
TABLE E-continued
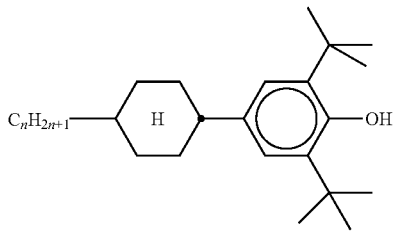
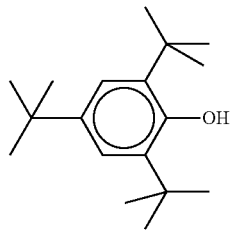
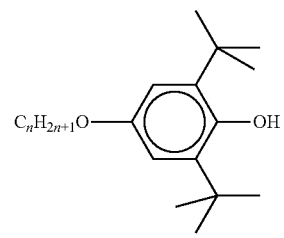

TABLE E-continued
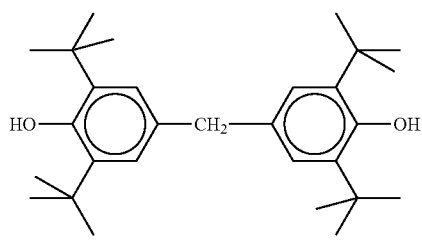
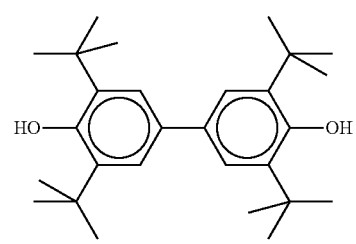
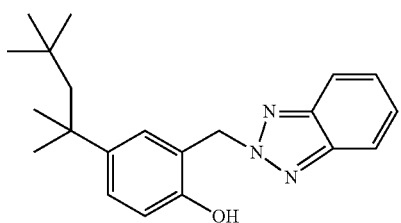 [SMILES: CC(C)(C)CC(C)(C)c1ccc(O)c(Cn2nc3ccccc3n2)c1]
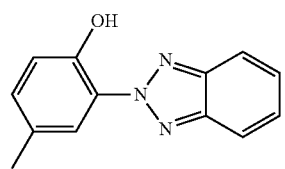 [SMILES: Cc1ccc(O)c(-n2nc3ccccc3n2)c1]
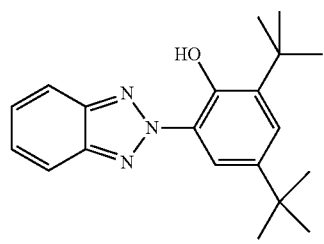 [SMILES: CC(C)(C)c1cc(-n2nc3ccccc3n2)c(O)c(C(C)(C)C)c1]
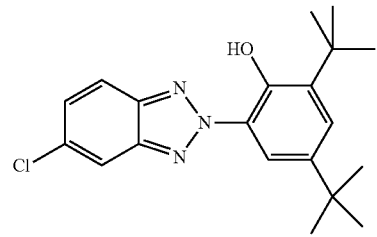 [SMILES: CC(C)(C)c1cc(-n2nc3ccc(Cl)cc3n2)c(O)c(C(C)(C)C)c1]
TABLE E-continued
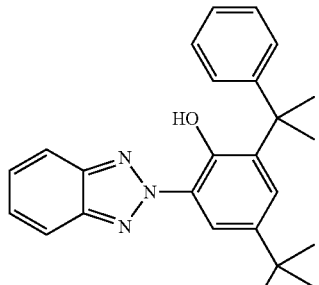
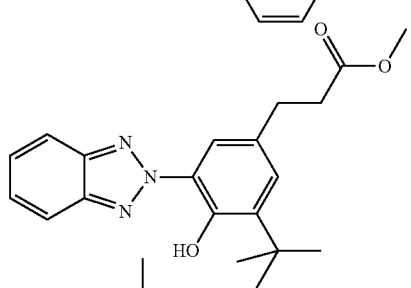
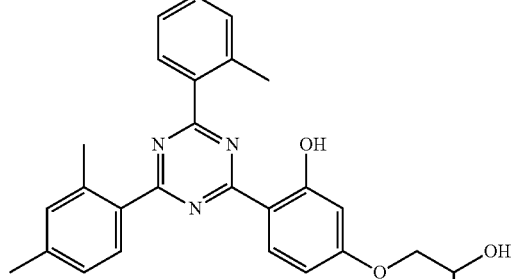
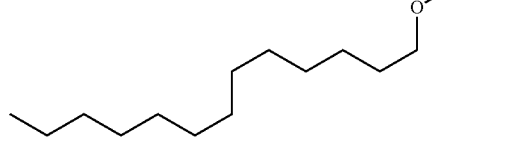
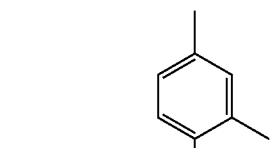
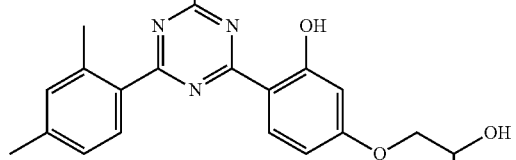
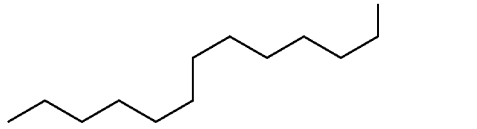

TABLE E-continued
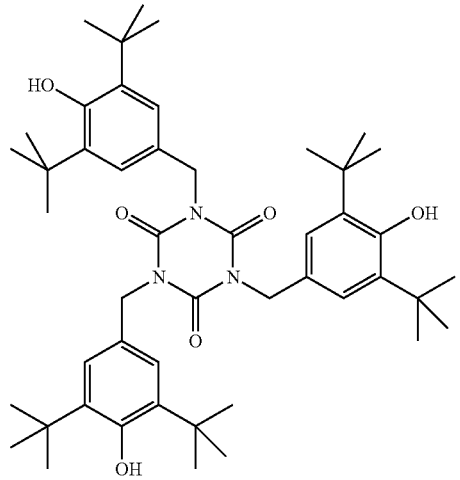 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
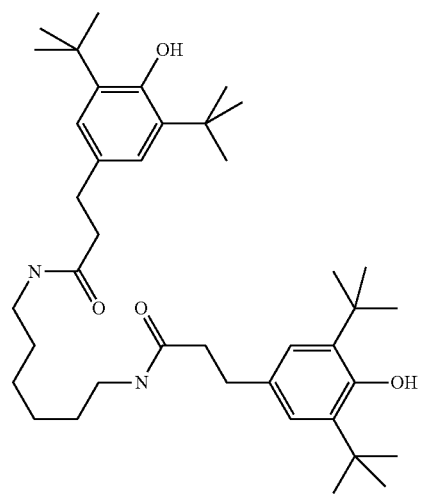 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
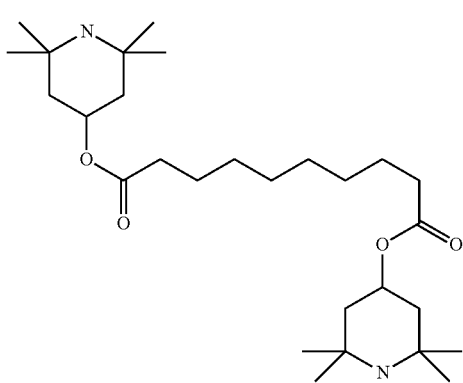
TABLE E-continued
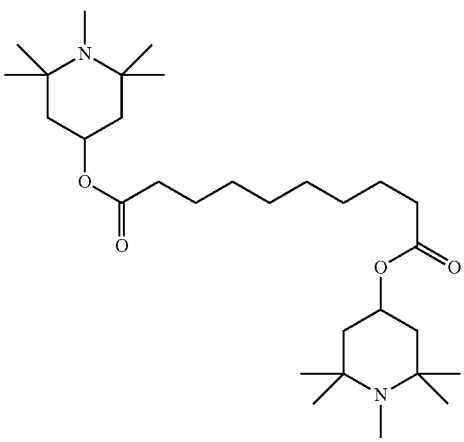
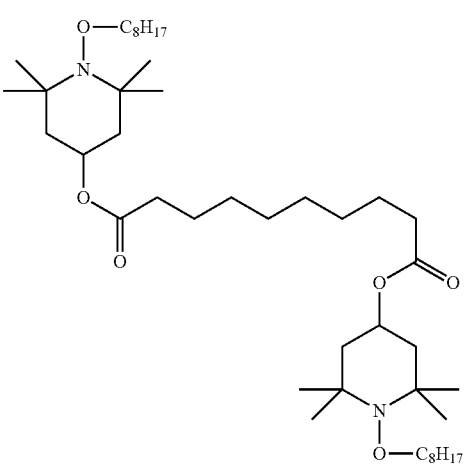
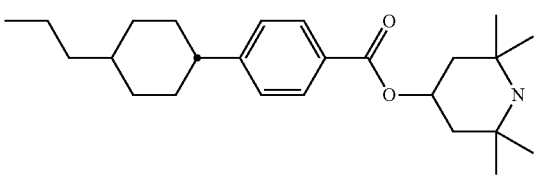
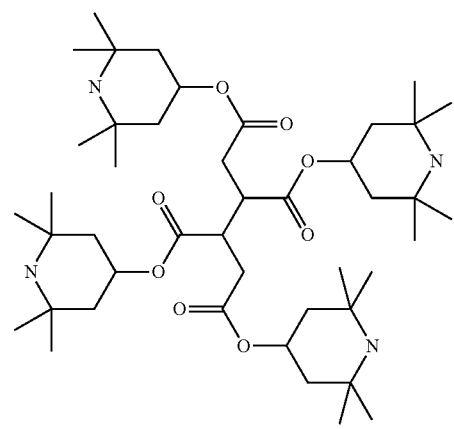

TABLE E-continued

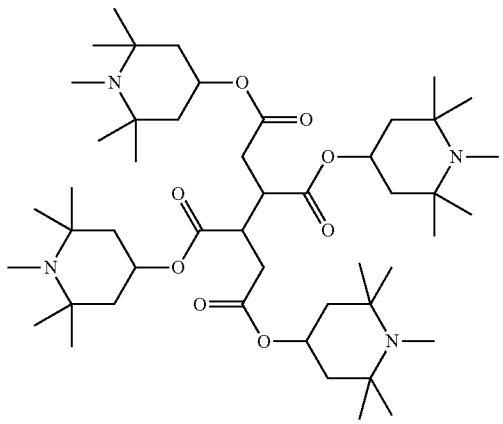

TABLE E-continued

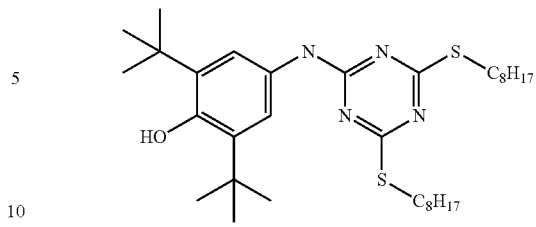

In a preferred embodiment of the present invention, the mesogenic media comprise one or more compounds selected from the group of the compounds from Table E.

The following table, Table F, shows illustrative compounds which can preferably be used as additional chiral dopants in the mesogenic media according to the present invention.

TABLE F

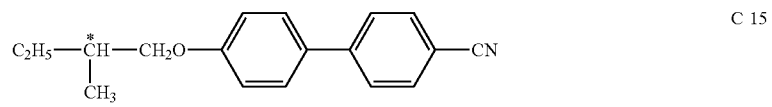

C 15

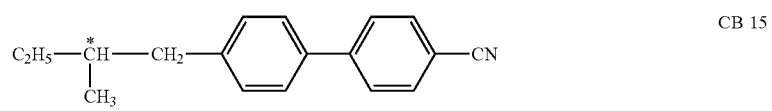

CB 15

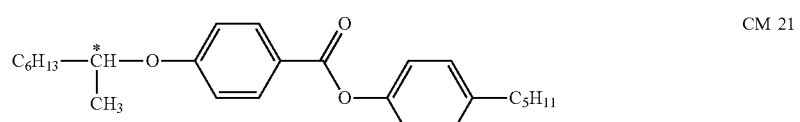

CM 21

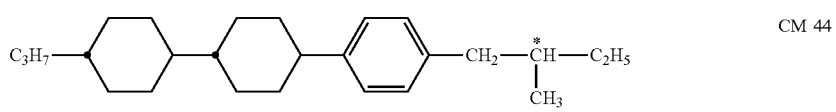

CM 44

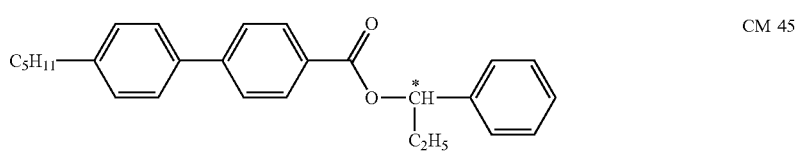

CM 45

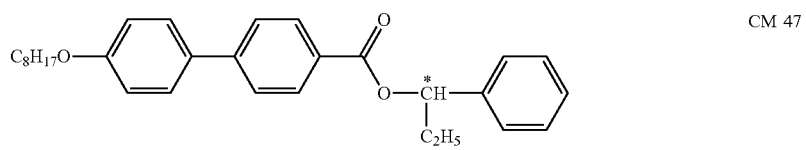

CM 47

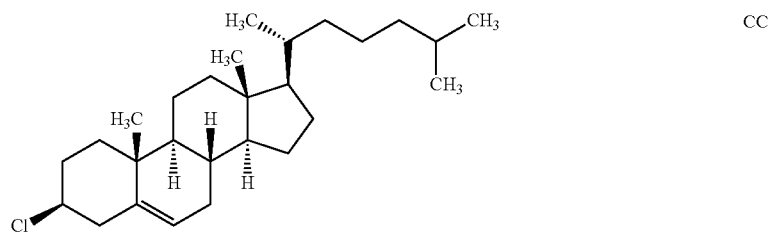

CC

TABLE F-continued

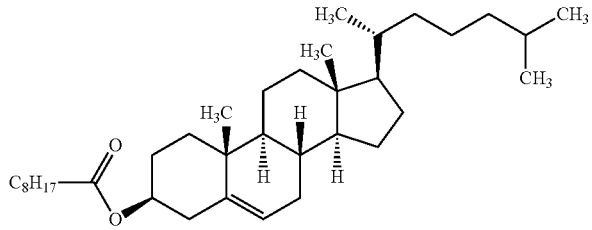 CN

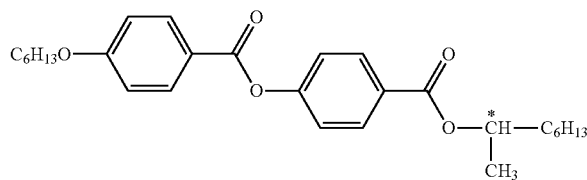 R/S-811

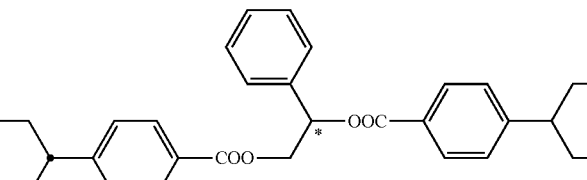 R/S-1011

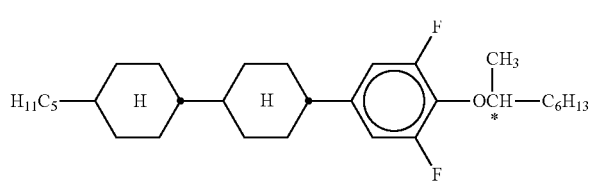 R/S-2011

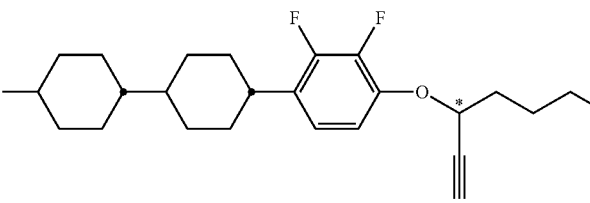 R/S-3011

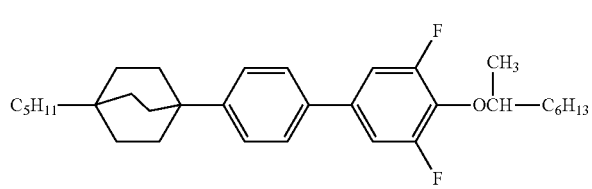 R/S-4011

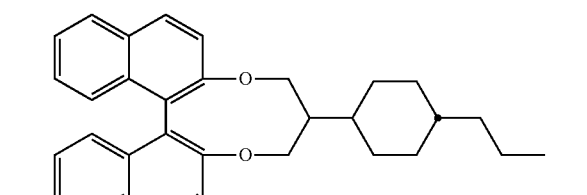 R/S-5011

In a preferred embodiment of the present invention, the mesogenic media comprise one or more compounds selected from the group of the compounds from Table F.

The mesogenic media according to the present application preferably comprise two or more, preferably four or more, compounds selected from the group consisting of the compounds from the above tables. The liquid-crystal media according to the present invention preferably comprise seven or more, preferably eight or more, compounds, preferably compounds having three or more, preferably four or more, different formulae, selected from the group of the compounds from Table D.

The following abbreviations are used m.p. denotes melting point clp. denotes clearing temperature Δn denotes the optical anisotropy measured at 20° C. and 589 nm $n_e$ denotes the extraordinary refractive index at 20° C. and 589 nm Δε denotes the dielectric anisotropy at 20° C.

$\varepsilon_\parallel$ denotes the dielectric constant in the parallel direction to the molecular axis $\varepsilon_\perp$ denotes the dielectric constant perpendicular to the molecular axis Kp denotes the clearing point [° C.]

$\gamma_1$ denotes the rotational viscosity [mPa s]

Δλ denotes the maximum variation of the reflection wavelength [nm] within a given temperature range, or between −20° C. and +70° C. unless stated otherwise BINOL 1,1'-Binaphthyl-2-2' diol DMAP 4-(N,N-Dimethylamino)pyridine Ms Methanesulfonyl MTB Methyl-tert.-butyl RT Room temperature THF Tetrahydrofuran TMEDA Tetramethylethylenediamine Tf Trifluoromethanesulfonyl Ts p-Toluenesulfonyl The values of the helical twisting power HTP of a chiral compound in a liquid crystalline host are given according to the equation HTP=$(p \ast c)^{-1}$ in $\mu m^{-1}$, wherein p is the pitch of the molecular helix, given in m, and c is the concentration by weight of the chiral compound in the host given in relative values (thus, e.g. a concentration of 1% by weight is corresponding to a value of c of 0.01). Unless stated otherwise, the HTP values were determined in the commercially available liquid crystal host mixture MLC-6260 (Merck KGaA, Darmstadt, Germany) using the Cano wedge cell method at a temperature of 20° C.

The following abbreviations are used to illustrate the liquid crystalline phase behaviour of the compounds: C=crystalline; N=nematic; S=smectic; N*, Ch=chiral nematic or cholesteric; I=isotropic. The numbers between these symbols indicate the phase transition temperatures in degree Celsius.

In the present invention the terms "cholesteric" and "chiral nematic" are used synonymously.

C* in a chemical formula denotes a chiral C atom. "Conventional workup" means: water is added if necessary, the mixture is extracted with methylene chloride, diethyl ether or toluene, the phases are separated, the organic phase is dried and concentrated by evaporation, and the product is purified by crystallization and/or chromatography.

EXAMPLES

In the following examples the invention is described in grater detail without delimiting it in any way.

Examples can be repeated with similar success by substituting the generically or specifically described reactants and/or operating conditions of this invention for those used in the preceding examples.

1. Synthesis

Example 1: 12,15-Di(naphthalen-2-yl)-5-(4-pentylcyclohexyl)-5,6-dihydro-4H-dinaphtho[2,1-f:1',2'-h][1,5]dioxonine 1.1 7-Methoxy-2-trifluoromethanesulfonyloxy naphthalene

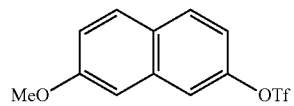 [SMILES: COc1ccc2ccc(OS(=O)(=O)C(F)(F)F)cc2c1]

To a mixture of 7-methoxy-2-naphthol (25.0 g, 144 mmol) and DMAP (0.70 g, 5.7 mmol) in $CH_2Cl_2$ (400 mL), triethylamine (30 mL) is added. The yellow reaction mixture is cooled to 0° C. At this temperature trifluoromethane sulfonic acid anhydride (33 mL, 200 mmol) is added dropwise. The solution is allowed to warm to room temperature and stirred for 20 h. The resulting mixture is poured into ice water and extracted with $CH_2Cl_2$. The combined organic layers are washed with water (1×200 mL), dried with $NaSO_4$ and concentrated under reduced pressure. The product is purified by column chromatography (heptane/toluene 1:1) and crystallized from heptane.

1.2 7-Methoxy-2,2'-binaphthyl

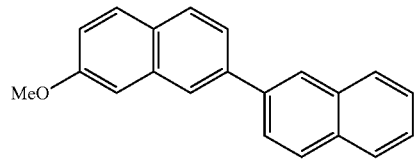 [SMILES: COc1ccc2ccc(-c3ccc4ccccc4c3)cc2c1]

A flask is flushed with nitrogen and charged with a mixture of 7-methoxy-2-trifluoromethanesulfonyloxy naphthalene (60.0 g, 195.9 mmol), 2-naphthylboronic acid (41.70 g, 235.1 mmol) and THF (700 mL). Then $NaBO_2 \cdot 4H_2O$ (41.34 g, 293.9 mmol), 180 mL water, $PdCl_2(PPh_3)_2$ (2.75 g, 3.9 mmol) and 2-3 drops of hydrazinium hydroxide are added. The mixture is stirred at 60° C. for 20 h, cooled to room temperature, diluted with water (300 mL) and extracted with MTB ether (600 mL). The organic phases are washed with water (1×400 mL), dried with $NaSO_4$ and concentrated under reduced pressure. The product is purified by column chromatography (heptane/toluene 1:1) and crystallized from heptane.

1.3 7-Hydroxy-2,2'-binaphthyl

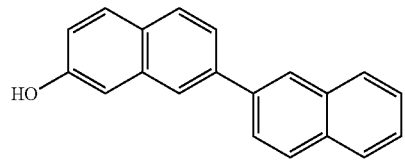 [SMILES: Oc1ccc2ccc(-c3ccc4ccccc4c3)cc2c1]

To a solution of 7-methoxy-2,2'-binaphthyl (1.50 g, 5.2 mmol) in CH$_2$Cl$_2$ (30 mL) at 5° C. BBr$_3$ (0.75 mL, 7.9 mmol) is added. The solution is allowed to warm to room temperature and stirred for 20 h. The excess of BBr$_3$ is decomposed by the dropwise addition of water. The resulting mixture is diluted with water and extracted with CH$_2$Cl$_2$ (100 mL). The organic phase is washed with saturated NaHCO$_3$ (2×50 mL), water (1×50 mL) and dried with NaSO$_4$. The solvent is removed under reduced pressure and the product is purified by crystallization from toluene.

1.4 2,2'-Dihydroxy-7,7'-dinaphthyl-1,1'-binaphthyl

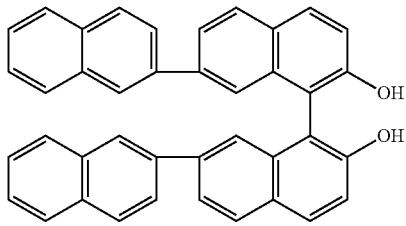 [SMILES: Oc1ccc2ccc(-c3ccc4ccccc4c3)cc2c1-c1c(O)ccc2ccc(-c3ccc4ccccc4c3)cc12]

7-Hydroxy-2,2'-binaphthyl (1.00 g, 3.7 mmol) is added to a mixture of CuCl(OH)-TMEDA (20 mg, 0.04 mmol) in CH$_2$Cl$_2$ (40 mL) and the whole is stirred at room temperature for 20 h exposed to air. The solvent is removed under reduced pressure and purified by column chromatography (toluene/ethylacetate 9:1). Crystallization from toluene gives 2,2'-dihydroxy-7,7'-dinaphthyl-1,1'-binaphthyl as a white solid.

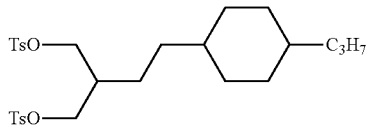

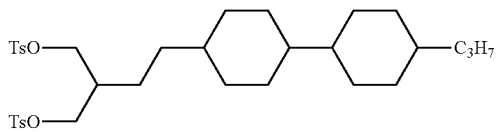

1.5 12,15-Di(naphthalen-2-yl)-5-(4-pentylcyclohexyl)-5,6-dihydro-4H-dinaphtho[2,1-f:1',2'-h][1,5]dioxonine

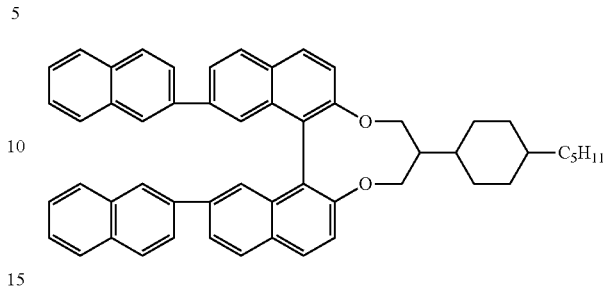

A mixture of 2,2'-dihydroxy-7,7'-dinaphthyl-1,1'-binaphthyl (1.50 g, 2.48 mmol) and K$_2$CO$_3$ (0.38 g, 2.73 mmol) in 30 mL DMF is stirred at 80° C. At this temperature a solution of 2-(4-n-pentylcyclohexyl)propane-1,3-diolditosylate (1.64 g, 2.97 mmol) in 20 mL DMF is added dropwise to the reaction mixture. The reaction is stirred for 20 h at 80° C. After cooling to room temperature, the reaction mixture is poured onto water and extracted with MTB ether (100 mL). The organic phase was washed with water (1×50 mL) and dried with NaSO$_4$. The solvent is removed under reduced pressure and the product is purified by column chromatography (heptane/toluene 1:1). The racemic product is separated into enantiomers by chiral HPLC on ChiralPak IA. 12,15-Di(naphthalen-2-yl)-5-(4-pentylcyclohexyl)-5,6-dihydro-4H-dinaphtho[2,1-f:1',2'-h][1,5]dioxonine is obtained as colorless solid, mp. 113° C.

This standard procedure (SP-1) is also used for the reaction between 2,2'-Dihydroxy-7,7'-dinaphthyl-1,1'-binaphthyl and the following ditosylates to give Examples 2 to 5.

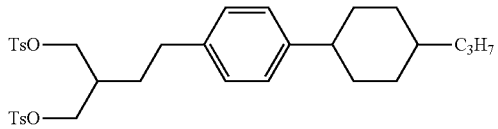

Example 2

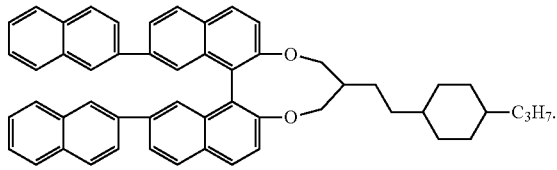

Amorphous Solid

Example 3

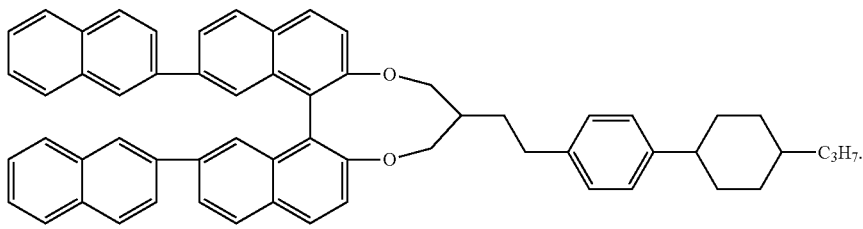

Amorphous Solid

Example 4

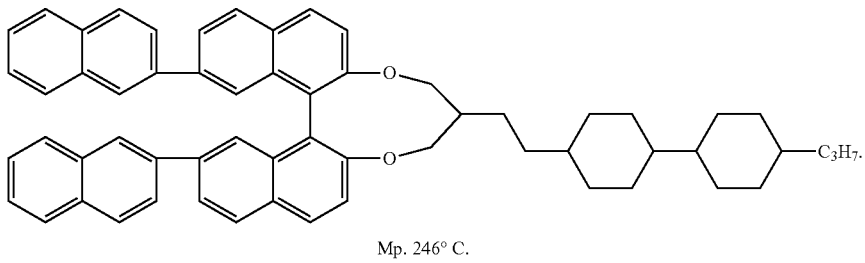

Mp. 246° C.

Example 5 (Not in Accordance with the Invention): 2,2'-Methylenedioxy-7,7'-bis-[4-(4-propyl-cyclohexyl)phenyl]-[1,1']binaphthalene 5.1
7-(4-(4-propylcyclohexyl)phenyl)naphthalen-2-ol

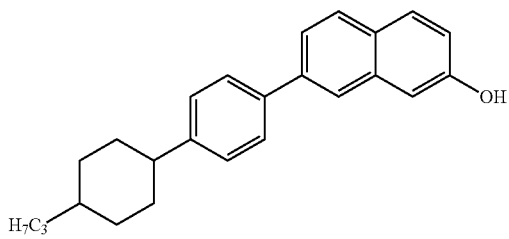

A flask is flushed with nitrogen and charged with a mixture of 7-bromo-2-naphthol (10.5 g, 46.6 mmol), (4-(4-propylcyclohexyl)benzene)boronic acid (13.77 g, 55.92 mmol) and THF (100 mL). Then $NaBO_2 \cdot 4H_2O$ (9.83 g, 69.9 mmol), 30 mL water, $PdCl_2(PPh_3)_2$ (1.64 g, 2.33 mmol) and 2-3 drops of hydrazinium hydroxide are added. The mixture is stirred at 60° C. for 5 h. The mixture is cooled to room temperature, diluted with water (250 mL), extracted with MTB ether (300 mL) and filtered through a pad of celite. The organic phases are is washed with water (1×100 mL), dried with $NaSO_4$ and concentrated under reduced pressure. The product is purified by crystallization from heptane/ethylacetate 10:1.

5.2 7,7'-bis(4-(4-propylcyclohexyl)phenyl)-[1,1'-binaphthalene]-2,2'-diol

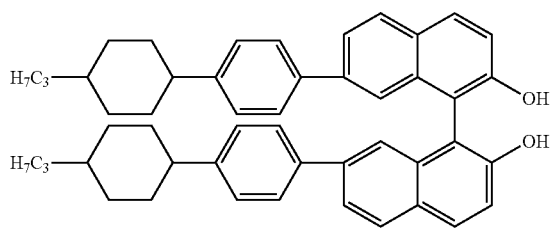

7-(4-(4-propylcyclohexyl)phenyl)naphthalen-2-ol (1.00 g, 2.9 mmol) is added to a mixture of CuCl(OH)-TMEDA (14 mg, 0.04 mmol) in $CH_2Cl_2$ (50 mL) and the reaction is stirred at room temperature for 4 h exposed to air. The solvent is removed under reduced pressure and purified by column chromatography (toluene/ethylacetate 95:5). Crystallization from a mixture of heptane/ethyl acetate/toluene 5:4:1 gives 7,7'-bis(4-(4-propyl-cyclohexyl)phenyl)-[1,1'-binaphthalene]-2,2'-diol as a white solid.

5.3 2,2'-Methylenedioxy-7,7'-bis-[4-(4-propyl-cyclohexyl)phenyl]-[1,1']binaphthalene

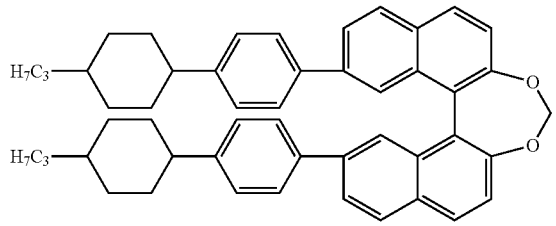

A mixture of 7,7'-bis(4-(4-propylcyclohexyl)phenyl)-[1,1'-binaphthalene]-2,2'-diol (2.00 g, 2.90 mmol), diiodomethane (2.33 g, 8.71 mmol) and $K_2CO_3$ (1.73 g, 17.42 mmol) in 50 mL DMF is stirred at 80° C. under nitrogen for 20 h. After cooling to room temperature, the reaction mixture is poured onto water (100 mL) and extracted with MTB ether (200 mL). The organic phase is washed with water (1×100 mL) and dried with $NaSO_4$. The solvent is removed under reduced pressure and the product is purified by column chromatography (toluene). The racemic product is separated into enantiomers by chiral HPLC on ChiralCel OD-H to give optically active 2,2'-Methylenedioxy-7,7'-bis-[4-(4-propyl-cyclohexyl)phenyl]-[1,1']binaphthalene as colorless crystals, m.p 125° C.

Example 6: 5-(4-pentylcyclohexyl)-12,15-bis(4-(4-propylcyclohexyl)-phenyl)-5,6-dihydro-4H-dinaphtho[2,1-f:1',2'-h][1,5]dioxonine

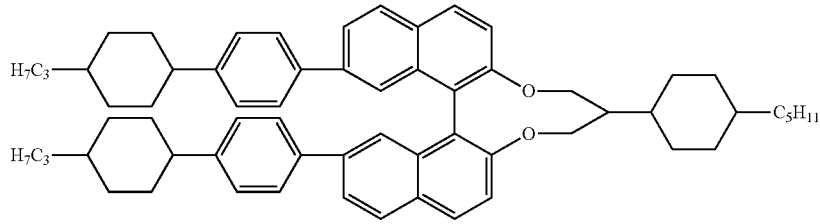

From 7,7'-bis(4-(4-propylcyclohexyl)phenyl)-[1,1'-binaphthalene]-2,2'-diol (step 5.2) example 6 is synthesized using the standard procedure SP-1 described above. The racemic product is separated into enantiomers by chiral HPLC on ChiralPak AD-H.

Example 7 (Not in Accordance with the Invention): 2,2'-Methylenedioxy-7,7'-bis-[4-(4-propyl-cyclohexyl)phenyl]-[1,1']binaphthalene 7.1
7-(4-(4-propylcyclohexyl)phenyl)naphthalen-2-ol

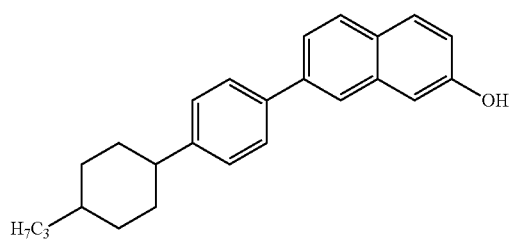

A flask is flushed with nitrogen and charged with a mixture of 7-bromo-2-naphthol (10.50 g, 46.6 mmol), (4-(4-propylcyclohexyl)phenyl)boronic acid (13.77 g, 55.92 mmol) and THF (100 mL). Then $NaBO_2 \cdot 4H_2O$ (9.83 g, 69.9 mmol), 30 mL water, $PdCl_2(PPh_3)_2$ (1.64 g, 2.33 mmol) and 2-3 drops of hydrazinium hydroxide are added. The mixture is stirred at 60° C. for 5 h. The mixture is cooled to room temperature, diluted with water (250 mL), extracted with MTB ether (300 mL) and filtered through a pad of celite. The organic phases are washed with water (1×100 mL), dried with $NaSO_4$ and concentrated under reduced pressure. The product is purified by crystallization from heptane/ethyl acetate (10:1).

7.2 7,7'-bis(4-(4-propylcyclohexyl)phenyl)-[1,1'-binaphthalene]-2,2'-diol

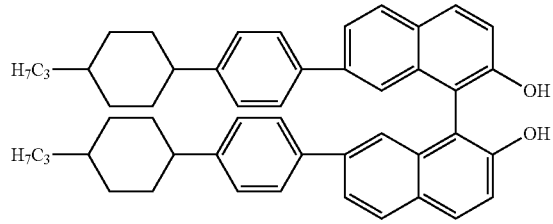

7-(4-(4-propylcyclohexyl)phenyl)naphthalen-2-ol (1.00 g, 2.9 mmol) is added to a mixture of CuCl(OH)-TMEDA (14 mg, 0.04 mmol) in $CH_2Cl_2$ (50 mL) and the whole is stirred at room temperature for 4 h in open air. The solvent is removed under reduced pressure and purified by column chromatography (toluene/ethyl acetate 95:5). Crystallization from a mixture of heptane/ethyl acetate/toluene 5:4:1 gives 7,7'-bis(4-(4-propyl-cyclohexyl)phenyl)-[1,1'-binaphthalene]-2,2'-diol as a white solid.

7.3 2,2'-Methylenedioxy-7,7'-bis-[4-(4-propyl-cyclohexyl)phenyl]-[1,1']binaphthalene

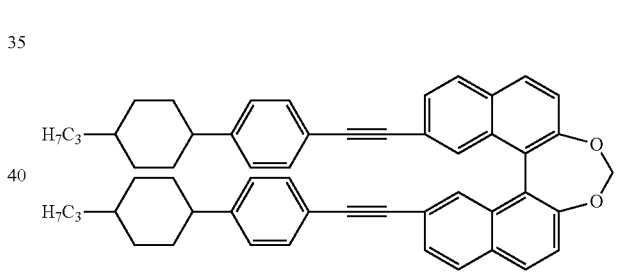

A mixture of 7,7'-bis(4-(4-propylcyclohexyl)phenyl)-[1,1'-binaphthalene]-2,2'-diol (2.00 g, 2.90 mmol), diiodomethane (2.33 g, 8.71 mmol), $K_2CO_3$ (1.73 g, 17.42 mmol) and 50 mL DMF is stirred at 80° C. under nitrogen for 20 h. After cooling to room temperature, the reaction mixture is poured into water (100 mL) and extracted with MTB ether (200 mL). The organic phase is washed with water (1×100 mL) and dried with $NaSO_4$. The solvent is removed under reduced pressure and the product is purified by column chromatography (toluene). Crystallization from heptane gives 2,2'-methylenedioxy-7,7'-bis-[4-(4-propyl-cyclohexyl)phenyl]-[1,1']binaphthalene as a colorless solid. The racemic product is separated into enantiomers by chiral HPLC on ChiralCel OD-H to give optically active 2,2'-Methylenedioxy-7,7'-bis-[4-(4-propyl-cyclohexyl)phenyl]-[1,1']binaphthalene as colorless solid, mp. 113° C.

From 7,7'-bis(4-(4-propylcyclohexyl)phenyl)-[1,1'-binaphthalene]-2,2'-diol (step 7.2) and according to general procedure SP-1 above, the following examples 8, 9 an 10 are obtained.

Example 8

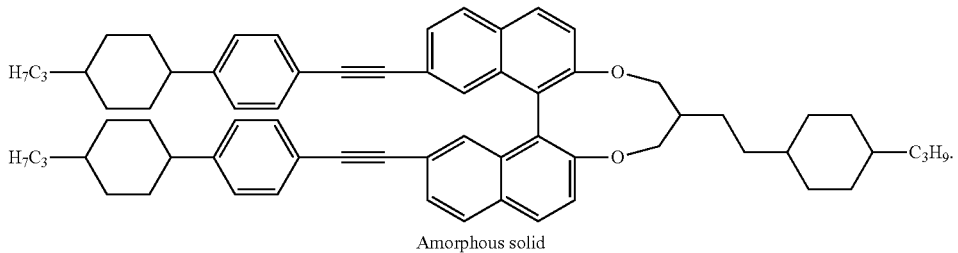

Amorphous solid

Example 9

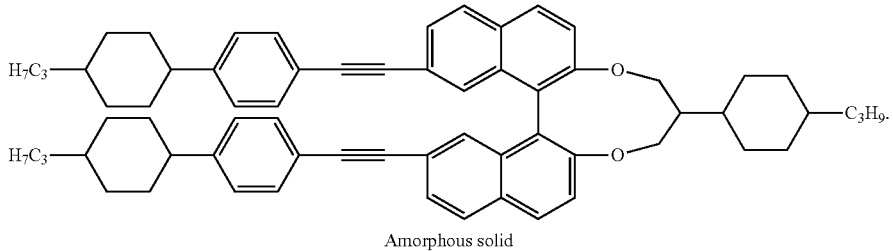

Amorphous solid

Example 10

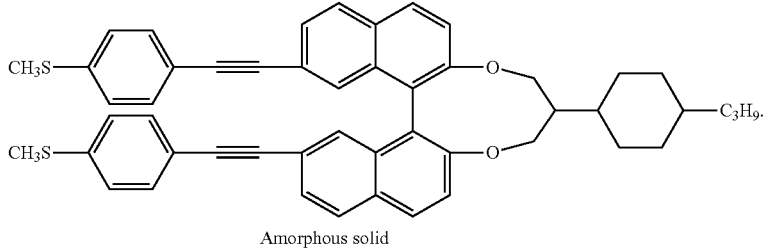

Amorphous solid

In analogy to example 1 the compounds of the formula

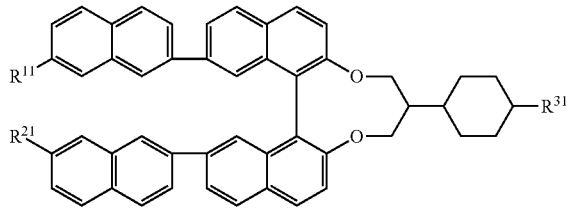

are obtained:

| Example | $R^{11}$ | $R^{21}$ | $R^{31}$ |
| --- | --- | --- | --- |
| 11 | H | H | —$CH_3$ |
| 12 | H | H | —$C_2H_5$ |
| 13 | H | H | n-$C_3H_7$ |
| 14 | H | H | n-$C_4H_9$ |
| 1 | H | H | n-$C_5H_{11}$ |
| 15 | —$CH_3$ | —$CH_3$ | —$CH_3$ |
| 16 | —$CH_3$ | —$CH_3$ | —$C_2H_5$ |
| 17 | —$CH_3$ | —$CH_3$ | n-$C_3H_7$ |
| 18 | —$CH_3$ | —$CH_3$ | n-$C_4H_9$ |
| 19 | —$CH_3$ | —$CH_3$ | n-$C_5H_{11}$ |
| 20 | —$C_2H_5$ | —$C_2H_5$ | —$CH_3$ |
| 21 | —$C_2H_5$ | —$C_2H_5$ | —$C_2H_5$ |
| 22 | —$C_2H_5$ | —$C_2H_5$ | n-$C_3H_7$ |
| 23 | —$C_2H_5$ | —$C_2H_5$ | n-$C_4H_9$ |
| 24 | —$C_2H_5$ | —$C_2H_5$ | n-$C_5H_{11}$ |
| 25 | n-$C_3H_7$ | n-$C_3H_7$ | —$CH_3$ |
| 26 | n-$C_3H_7$ | n-$C_3H_7$ | —$C_2H_5$ |
| 27 | n-$C_3H_7$ | n-$C_3H_7$ | n-$C_3H_7$ |
| 28 | n-$C_3H_7$ | n-$C_3H_7$ | n-$C_4H_9$ |
| 29 | n-$C_3H_7$ | n-$C_3H_7$ | n-$C_5H_{11}$ |
| 30 | n-$C_4H_9$ | n-$C_4H_9$ | —$CH_3$ |
| 31 | n-$C_4H_9$ | n-$C_4H_9$ | —$C_2H_5$ |
| 32 | n-$C_4H_9$ | n-$C_4H_9$ | n-$C_3H_7$ |
| 33 | n-$C_4H_9$ | n-$C_4H_9$ | n-$C_4H_9$ |
| 34 | n-$C_4H_9$ | n-$C_4H_9$ | n-$C_5H_{11}$ |
| 35 | n-$C_5H_{11}$ | n-$C_5H_{11}$ | —$CH_3$ |
| 36 | n-$C_5H_{11}$ | n-$C_5H_{11}$ | —$C_2H_5$ |
| 37 | n-$C_5H_{11}$ | n-$C_5H_{11}$ | n-$C_3H_7$ |
| 38 | n-$C_5H_{11}$ | n-$C_5H_{11}$ | n-$C_4H_9$ |
| 39 | n-$C_5H_{11}$ | n-$C_5H_{11}$ | n-$C_5H_{11}$ |

In analogy to example 2 the compounds of the formula

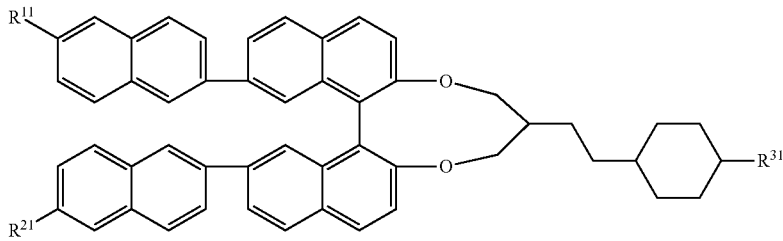

are obtained:

| Example | R$^{11}$ | R$^{21}$ | R$^{31}$ |
|---|---|---|---|
| 40 | H | H | —CH$_3$ |
| 41 | H | H | —C$_2$H$_5$ |
| 2 | H | H | n-C$_3$H$_7$ |
| 42 | H | H | n-C$_4$H$_9$ |
| 43 | H | H | n-C$_5$H$_{11}$ |
| 44 | —CH$_3$ | —CH$_3$ | —CH$_3$ |
| 45 | —CH$_3$ | —CH$_3$ | —C$_2$H$_5$ |
| 46 | —CH$_3$ | —CH$_3$ | n-C$_3$H$_7$ |
| 47 | —CH$_3$ | —CH$_3$ | n-C$_4$H$_9$ |
| 48 | —CH$_3$ | —CH$_3$ | n-C$_5$H$_{11}$ |
| 49 | —C$_2$H$_5$ | —C$_2$H$_5$ | —CH$_3$ |
| 50 | —C$_2$H$_5$ | —C$_2$H$_5$ | —C$_2$H$_5$ |
| 51 | —C$_2$H$_5$ | —C$_2$H$_5$ | n-C$_3$H$_7$ |
| 52 | —C$_2$H$_5$ | —C$_2$H$_5$ | n-C$_4$H$_9$ |
| 53 | —C$_2$H$_5$ | —C$_2$H$_5$ | n-C$_5$H$_{11}$ |
| 54 | n-C$_3$H$_7$ | n-C$_3$H$_7$ | —CH$_3$ |
| 55 | n-C$_3$H$_7$ | n-C$_3$H$_7$ | —C$_2$H$_5$ |
| 56 | n-C$_3$H$_7$ | n-C$_3$H$_7$ | n-C$_3$H$_7$ |
| 57 | n-C$_3$H$_7$ | n-C$_3$H$_7$ | n-C$_4$H$_9$ |
| 58 | n-C$_3$H$_7$ | n-C$_3$H$_7$ | n-C$_5$H$_{11}$ |
| 59 | n-C$_4$H$_9$ | n-C$_4$H$_9$ | —CH$_3$ |
| 60 | n-C$_4$H$_9$ | n-C$_4$H$_9$ | —C$_2$H$_5$ |
| 61 | n-C$_4$H$_9$ | n-C$_4$H$_9$ | n-C$_3$H$_7$ |
| 62 | n-C$_4$H$_9$ | n-C$_4$H$_9$ | n-C$_4$H$_9$ |
| 63 | n-C$_4$H$_9$ | n-C$_4$H$_9$ | n-C$_5$H$_{11}$ |
| 64 | n-C$_5$H$_{11}$ | n-C$_5$H$_{11}$ | —CH$_3$ |
| 65 | n-C$_5$H$_{11}$ | n-C$_5$H$_{11}$ | —C$_2$H$_5$ |
| 66 | n-C$_5$H$_{11}$ | n-C$_5$H$_{11}$ | n-C$_3$H$_7$ |
| 67 | n-C$_5$H$_{11}$ | n-C$_5$H$_{11}$ | n-C$_4$H$_9$ |
| 68 | n-C$_5$H$_{11}$ | n-C$_5$H$_{11}$ | n-C$_5$H$_{11}$ |

In analogy to example 3 the compounds of the formula

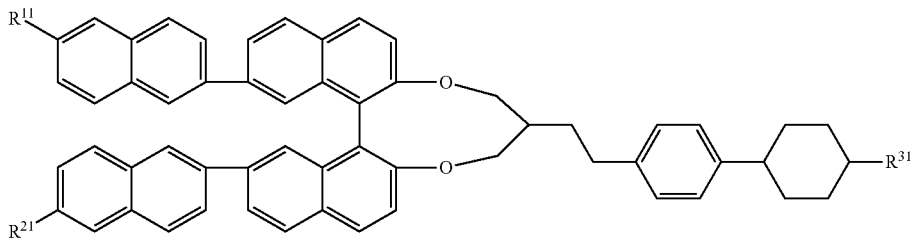

are obtained:

| Example | R$^{11}$ | R$^{21}$ | R$^{31}$ |
|---|---|---|---|
| 69 | H | H | —CH$_3$ |
| 70 | H | H | —C$_2$H$_5$ |
| 3 | H | H | n-C$_3$H$_7$ |
| 71 | H | H | n-C$_4$H$_9$ |
| 72 | H | H | n-C$_5$H$_{11}$ |
| 73 | —CH$_3$ | —CH$_3$ | —CH$_3$ |
| 74 | —CH$_3$ | —CH$_3$ | —C$_2$H$_5$ |
| 75 | —CH$_3$ | —CH$_3$ | n-C$_3$H$_7$ |
| 76 | —CH$_3$ | —CH$_3$ | n-C$_4$H$_9$ |

-continued

| Example | $R^{11}$ | $R^{21}$ | $R^{31}$ |
|---|---|---|---|
| 77 | —CH$_3$ | —CH$_3$ | n-C$_5$H$_{11}$ |
| 78 | —C$_2$H$_5$ | —C$_2$H$_5$ | —CH$_3$ |
| 79 | —C$_2$H$_5$ | —C$_2$H$_5$ | —C$_2$H$_5$ |
| 80 | —C$_2$H$_5$ | —C$_2$H$_5$ | n-C$_3$H$_7$ |
| 81 | —C$_2$H$_5$ | —C$_2$H$_5$ | n-C$_4$H$_9$ |
| 82 | —C$_2$H$_5$ | —C$_2$H$_5$ | n-C$_5$H$_{11}$ |
| 83 | n-C$_3$H$_7$ | n-C$_3$H$_7$ | —CH$_3$ |
| 84 | n-C$_3$H$_7$ | n-C$_3$H$_7$ | —C$_2$H$_5$ |
| 85 | n-C$_3$H$_7$ | n-C$_3$H$_7$ | n-C$_3$H$_7$ |
| 86 | n-C$_3$H$_7$ | n-C$_3$H$_7$ | n-C$_4$H$_9$ |
| 87 | n-C$_3$H$_7$ | n-C$_3$H$_7$ | n-C$_5$H$_{11}$ |
| 88 | n-C$_4$H$_9$ | n-C$_4$H$_9$ | —CH$_3$ |
| 89 | n-C$_4$H$_9$ | n-C$_4$H$_9$ | —C$_2$H$_5$ |
| 90 | n-C$_4$H$_9$ | n-C$_4$H$_9$ | n-C$_3$H$_7$ |
| 91 | n-C$_4$H$_9$ | n-C$_4$H$_9$ | n-C$_4$H$_9$ |
| 92 | n-C$_4$H$_9$ | n-C$_4$H$_9$ | n-C$_5$H$_{11}$ |
| 93 | n-C$_5$H$_{11}$ | n-C$_5$H$_{11}$ | —CH$_3$ |
| 94 | n-C$_5$H$_{11}$ | n-C$_5$H$_{11}$ | —C$_2$H$_5$ |
| 95 | n-C$_5$H$_{11}$ | n-C$_5$H$_{11}$ | n-C$_3$H$_7$ |
| 96 | n-C$_5$H$_{11}$ | n-C$_5$H$_{11}$ | n-C$_4$H$_9$ |
| 97 | n-C$_5$H$_{11}$ | n-C$_5$H$_{11}$ | n-C$_5$H$_{11}$ |

In analogy to example 4 the compounds of the formula

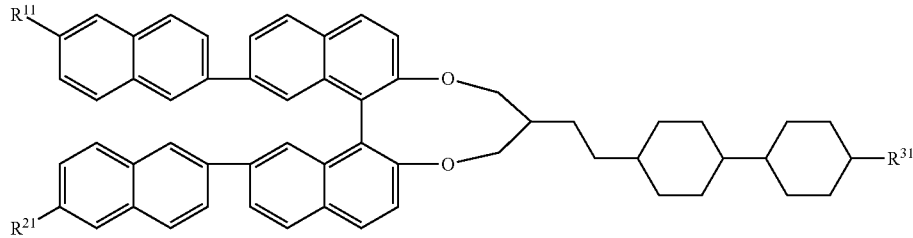

are obtained:

| Example | $R^{11}$ | $R^{21}$ | $R^{31}$ |
|---|---|---|---|
| 98 | H | H | —CH$_3$ |
| 99 | H | H | —C$_2$H$_5$ |
| 4 | H | H | n-C$_3$H$_7$ |
| 100 | H | H | n-C$_4$H$_9$ |
| 101 | H | H | n-C$_5$H$_{11}$ |
| 102 | —CH$_3$ | —CH$_3$ | —CH$_3$ |
| 103 | —CH$_3$ | —CH$_3$ | —C$_2$H$_5$ |
| 104 | —CH$_3$ | —CH$_3$ | n-C$_3$H$_7$ |
| 105 | —CH$_3$ | —CH$_3$ | n-C$_4$H$_9$ |
| 106 | —CH$_3$ | —CH$_3$ | n-C$_5$H$_{11}$ |
| 107 | —C$_2$H$_5$ | —C$_2$H$_5$ | —CH$_3$ |
| 108 | —C$_2$H$_5$ | —C$_2$H$_5$ | —C$_2$H$_5$ |
| 109 | —C$_2$H$_5$ | —C$_2$H$_5$ | n-C$_3$H$_7$ |
| 110 | —C$_2$H$_5$ | —C$_2$H$_5$ | n-C$_4$H$_9$ |
| 111 | —C$_2$H$_5$ | —C$_2$H$_5$ | n-C$_5$H$_{11}$ |
| 112 | n-C$_3$H$_7$ | n-C$_3$H$_7$ | —CH$_3$ |
| 113 | n-C$_3$H$_7$ | n-C$_3$H$_7$ | —C$_2$H$_5$ |
| 114 | n-C$_3$H$_7$ | n-C$_3$H$_7$ | n-C$_3$H$_7$ |
| 115 | n-C$_3$H$_7$ | n-C$_3$H$_7$ | n-C$_4$H$_9$ |
| 116 | n-C$_3$H$_7$ | n-C$_3$H$_7$ | n-C$_5$H$_{11}$ |
| 117 | n-C$_4$H$_9$ | n-C$_4$H$_9$ | —CH$_3$ |
| 118 | n-C$_4$H$_9$ | n-C$_4$H$_9$ | —C$_2$H$_5$ |
| 119 | n-C$_4$H$_9$ | n-C$_4$H$_9$ | n-C$_3$H$_7$ |
| 120 | n-C$_4$H$_9$ | n-C$_4$H$_9$ | n-C$_4$H$_9$ |
| 121 | n-C$_4$H$_9$ | n-C$_4$H$_9$ | n-C$_5$H$_{11}$ |
| 122 | n-C$_5$H$_{11}$ | n-C$_5$H$_{11}$ | —CH$_3$ |
| 123 | n-C$_5$H$_{11}$ | n-C$_5$H$_{11}$ | —C$_2$H$_5$ |
| 124 | n-C$_5$H$_{11}$ | n-C$_5$H$_{11}$ | n-C$_3$H$_7$ |
| 125 | n-C$_5$H$_{11}$ | n-C$_5$H$_{11}$ | n-C$_4$H$_9$ |
| 126 | n-C$_5$H$_{11}$ | n-C$_5$H$_{11}$ | n-C$_5$H$_{11}$ |

In analogy to example 5 the compounds of the formula

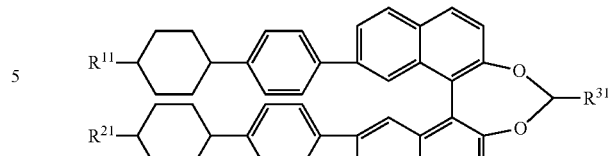

are obtained:

| Example | $R^{11}$ | $R^{21}$ | $R^{31}$ |
|---|---|---|---|
| 127 (Not in Accordance with the Invetion) | H | H | H |
| 128 (Not in Accordance with the Invetion) | H | H | —CH$_3$ |
| 129 (Not in Accordance with the Invetion) | H | H | —C$_2$H$_5$ |
| 130 (Not in Accordance with the Invetion) | H | H | n-C$_3$H$_7$ |
| 131 (Not in Accordance with the Invetion) | H | H | n-C$_4$H$_9$ |
| 132 (Not in Accordance with the Invetion) | H | H | n-C$_5$H$_{11}$ |
| 133 (Not in Accordance with the Invetion) | —CH$_3$ | —CH$_3$ | H |
| 134 (Not in Accordance with the Invetion) | —CH$_3$ | —CH$_3$ | —CH$_3$ |
| 135 (Not in Accordance with the Invetion) | —CH$_3$ | —CH$_3$ | —C$_2$H$_5$ |

-continued

| Example | $R^{11}$ | $R^{21}$ | $R^{31}$ |
|---|---|---|---|
| 136 (Not in Accordance with the Invetion) | —CH$_3$ | —CH$_3$ | n-C$_3$H$_7$ |
| 137 (Not in Accordance with the Invetion) | —CH$_3$ | —CH$_3$ | n-C$_4$H$_9$ |
| 138 (Not in Accordance with the Invetion) | —CH$_3$ | —CH$_3$ | n-C$_5$H$_{11}$ |
| 139 (Not in Accordance with the Invetion) | —C$_2$H$_5$ | —C$_2$H$_5$ | H |
| 140 (Not in Accordance with the Invetion) | —C$_2$H$_5$ | —C$_2$H$_5$ | —CH$_3$ |
| 141 (Not in Accordance with the Invetion) | —C$_2$H$_5$ | —C$_2$H$_5$ | —C$_2$H$_5$ |
| 142 (Not in Accordance with the Invetion) | —C$_2$H$_5$ | —C$_2$H$_5$ | n-C$_3$H$_7$ |
| 143 (Not in Accordance with the Invetion) | —C$_2$H$_5$ | —C$_2$H$_5$ | n-C$_4$H$_9$ |
| 144 (Not in Accordance with the Invetion) | —C$_2$H$_5$ | —C$_2$H$_5$ | n-C$_5$H$_{11}$ |
| 5 (Not in Accordance with the Invetion) | n-C$_3$H$_7$ | n-C$_3$H$_7$ | H |
| 145 (Not in Accordance with the Invetion) | n-C$_3$H$_7$ | n-C$_3$H$_7$ | —CH$_3$ |
| 146 (Not in Accordance with the Invetion) | n-C$_3$H$_7$ | n-C$_3$H$_7$ | —C$_2$H$_5$ |
| 147 (Not in Accordance with the Invetion) | n-C$_3$H$_7$ | n-C$_3$H$_7$ | n-C$_3$H$_7$ |
| 148 (Not in Accordance with the Invetion) | n-C$_3$H$_7$ | n-C$_3$H$_7$ | n-C$_4$H$_9$ |
| 149 (Not in Accordance with the Invetion) | n-C$_3$H$_7$ | n-C$_3$H$_7$ | n-C$_5$H$_{11}$ |
| 150 (Not in Accordance with the Invetion) | n-C$_4$H$_9$ | n-C$_4$H$_9$ | H |
| 151 (Not in Accordance with the Invetion) | n-C$_4$H$_9$ | n-C$_4$H$_9$ | —CH$_3$ |
| 152 (Not in Accordance with the Invetion) | n-C$_4$H$_9$ | n-C$_4$H$_9$ | —C$_2$H$_5$ |
| 153 (Not in Accordance with the Invetion) | n-C$_4$H$_9$ | n-C$_4$H$_9$ | n-C$_3$H$_7$ |
| 154 (Not in Accordance with the Invetion) | n-C$_4$H$_9$ | n-C$_4$H$_9$ | n-C$_4$H$_9$ |
| 155 (Not in Accordance with the Invetion) | n-C$_4$H$_9$ | n-C$_4$H$_9$ | n-C$_5$H$_{11}$ |
| 156 (Not in Accordance with the Invetion) | n-C$_5$H$_{11}$ | n-C$_5$H$_{11}$ | H |
| 157 (Not in Accordance with the Invetion) | n-C$_5$H$_{11}$ | n-C$_5$H$_{11}$ | —CH$_3$ |
| 158 (Not in Accordance with the Invetion) | n-C$_5$H$_{11}$ | n-C$_5$H$_{11}$ | —C$_2$H$_5$ |
| 159 (Not in Accordance with the Invetion) | n-C$_5$H$_{11}$ | n-C$_5$H$_{11}$ | n-C$_3$H$_7$ |
| 160 (Not in Accordance with the Invetion) | n-C$_5$H$_{11}$ | n-C$_5$H$_{11}$ | n-C$_4$H$_9$ |
| 161 (Not in Accordance with the Invetion) | n-C$_5$H$_{11}$ | n-C$_5$H$_{11}$ | n-C$_5$H$_{11}$ |

In analogy to example 6 the compounds of the formula

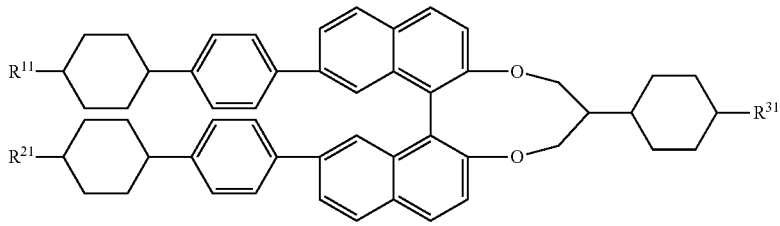

are obtained:

| Example | $R^{11}$ | $R^{21}$ | $R^{31}$ |
|---|---|---|---|
| 162 | H | H | —CH$_3$ |
| 163 | H | H | —C$_2$H$_5$ |
| 164 | H | H | n-C$_3$H$_7$ |
| 165 | H | H | n-C$_4$H$_9$ |
| 166 | H | H | n-C$_5$H$_{11}$ |
| 167 | —CH$_3$ | —CH$_3$ | —CH$_3$ |
| 168 | —CH$_3$ | —CH$_3$ | —C$_2$H$_5$ |
| 169 | —CH$_3$ | —CH$_3$ | n-C$_3$H$_7$ |
| 170 | —CH$_3$ | —CH$_3$ | n-C$_4$H$_9$ |
| 171 | —CH$_3$ | —CH$_3$ | n-C$_5$H$_{11}$ |
| 172 | —C$_2$H$_5$ | —C$_2$H$_5$ | —CH$_3$ |
| 173 | —C$_2$H$_5$ | —C$_2$H$_5$ | —C$_2$H$_5$ |
| 174 | —C$_2$H$_5$ | —C$_2$H$_5$ | n-C$_3$H$_7$ |
| 175 | —C$_2$H$_5$ | —C$_2$H$_5$ | n-C$_4$H$_9$ |
| 176 | —C$_2$H$_5$ | —C$_2$H$_5$ | n-C$_5$H$_{11}$ |
| 177 | n-C$_3$H$_7$ | n-C$_3$H$_7$ | —CH$_3$ |
| 178 | n-C$_3$H$_7$ | n-C$_3$H$_7$ | —C$_2$H$_5$ |
| 179 | n-C$_3$H$_7$ | n-C$_3$H$_7$ | n-C$_3$H$_7$ |
| 180 | n-C$_3$H$_7$ | n-C$_3$H$_7$ | n-C$_4$H$_9$ |
| 6 | n-C$_3$H$_7$ | n-C$_3$H$_7$ | n-C$_5$H$_{11}$ |
| 181 | n-C$_4$H$_9$ | n-C$_4$H$_9$ | —CH$_3$ |
| 182 | n-C$_4$H$_9$ | n-C$_4$H$_9$ | —C$_2$H$_5$ |
| 183 | n-C$_4$H$_9$ | n-C$_4$H$_9$ | n-C$_3$H$_7$ |
| 184 | n-C$_4$H$_9$ | n-C$_4$H$_9$ | n-C$_4$H$_9$ |
| 185 | n-C$_4$H$_9$ | n-C$_4$H$_9$ | n-C$_5$H$_{11}$ |
| 186 | n-C$_5$H$_{11}$ | n-C$_5$H$_{11}$ | —CH$_3$ |
| 187 | n-C$_5$H$_{11}$ | n-C$_5$H$_{11}$ | —C$_2$H$_5$ |
| 188 | n-C$_5$H$_{11}$ | n-C$_5$H$_{11}$ | n-C$_3$H$_7$ |
| 189 | n-C$_5$H$_{11}$ | n-C$_5$H$_{11}$ | n-C$_4$H$_9$ |
| 190 | n-C$_5$H$_{11}$ | n-C$_5$H$_{11}$ | n-C$_5$H$_{11}$ |

In analogy to example 7 the compounds of the formula

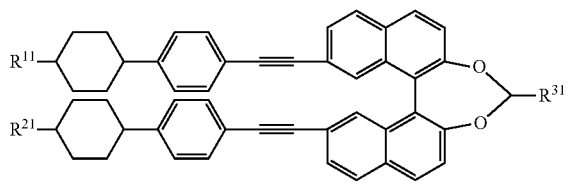

are obtained:

| Example | $R^{11}$ | $R^{21}$ | $R^{31}$ |
|---|---|---|---|
| 191 (Not in Accordance with the Invetion) | H | H | H |
| 192 (Not in Accordance with the Invetion) | H | H | —CH$_3$ |
| 193 (Not in Accordance with the Invetion) | H | H | —C$_2$H$_5$ |
| 194 (Not in Accordance with the Invetion) | H | H | n-C$_3$H$_7$ |
| 195 (Not in Accordance with the Invetion) | H | H | n-C$_4$H$_9$ |
| 196 (Not in Accordance with the Invetion) | H | H | n-C$_5$H$_{11}$ |
| 197 (Not in Accordance with the Invetion) | —CH$_3$ | —CH$_3$ | H |
| 198 (Not in Accordance with the Invetion) | —CH$_3$ | —CH$_3$ | —CH$_3$ |
| 199 (Not in Accordance with the Invetion) | —CH$_3$ | —CH$_3$ | —C$_2$H$_5$ |
| 200 (Not in Accordance with the Invetion) | —CH$_3$ | —CH$_3$ | n-C$_3$H$_7$ |
| 201 (Not in Accordance with the Invetion) | —CH$_3$ | —CH$_3$ | n-C$_4$H$_9$ |
| 202 (Not in Accordance with the Invetion) | —CH$_3$ | —CH$_3$ | n-C$_5$H$_{11}$ |
| 203 (Not in Accordance with the Invetion) | —C$_2$H$_5$ | —C$_2$H$_5$ | H |
| 204 (Not in Accordance with the Invetion) | —C$_2$H$_5$ | —C$_2$H$_5$ | —CH$_3$ |
| 205 (Not in Accordance with the Invetion) | —C$_2$H$_5$ | —C$_2$H$_5$ | —C$_2$H$_5$ |
| 206 (Not in Accordance with the Invetion) | —C$_2$H$_5$ | —C$_2$H$_5$ | n-C$_3$H$_7$ |
| 207 (Not in Accordance with the Invetion) | —C$_2$H$_5$ | —C$_2$H$_5$ | n-C$_4$H$_9$ |
| 208 (Not in Accordance with the Invetion) | —C$_2$H$_5$ | —C$_2$H$_5$ | n-C$_5$H$_{11}$ |
| 7 (Not in Accordance with the Invetion) | n-C$_3$H$_7$ | n-C$_3$H$_7$ | H |
| 209 (Not in Accordance with the Invetion) | n-C$_3$H$_7$ | n-C$_3$H$_7$ | —CH$_3$ |
| 210 (Not in Accordance with the Invetion) | n-C$_3$H$_7$ | n-C$_3$H$_7$ | —C$_2$H$_5$ |
| 211 (Not in Accordance with the Invetion) | n-C$_3$H$_7$ | n-C$_3$H$_7$ | n-C$_3$H$_7$ |
| 212 (Not in Accordance with the Invetion) | n-C$_3$H$_7$ | n-C$_3$H$_7$ | n-C$_4$H$_9$ |
| 213 (Not in Accordance with the Invetion) | n-C$_3$H$_7$ | n-C$_3$H$_7$ | n-C$_5$H$_{11}$ |
| 214 (Not in Accordance with the Invetion) | n-C$_4$H$_9$ | n-C$_4$H$_9$ | H |
| 215 (Not in Accordance with the Invetion) | n-C$_4$H$_9$ | n-C$_4$H$_9$ | —CH$_3$ |
| 216 (Not in Accordance with the Invetion) | n-C$_4$H$_9$ | n-C$_4$H$_9$ | —C$_2$H$_5$ |
| 217 (Not in Accordance with the Invetion) | n-C$_4$H$_9$ | n-C$_4$H$_9$ | n-C$_3$H$_7$ |
| 218 (Not in Accordance with the Invetion) | n-C$_4$H$_9$ | n-C$_4$H$_9$ | n-C$_4$H$_9$ |
| 219 (Not in Accordance with the Invetion) | n-C$_4$H$_9$ | n-C$_4$H$_9$ | n-C$_5$H$_{11}$ |
| 220 (Not in Accordance with the Invetion) | n-C$_5$H$_{11}$ | n-C$_5$H$_{11}$ | H |
| 221 (Not in Accordance with the Invetion) | n-C$_5$H$_{11}$ | n-C$_5$H$_{11}$ | —CH$_3$ |
| 222 (Not in Accordance with the Invetion) | n-C$_5$H$_{11}$ | n-C$_5$H$_{11}$ | —C$_2$H$_5$ |
| 223 (Not in Accordance with the Invetion) | n-C$_5$H$_{11}$ | n-C$_5$H$_{11}$ | n-C$_3$H$_7$ |
| 224 (Not in Accordance with the Invetion) | n-C$_5$H$_{11}$ | n-C$_5$H$_{11}$ | n-C$_4$H$_9$ |
| 225 (Not in Accordance with the Invetion) | n-C$_5$H$_{11}$ | n-C$_5$H$_{11}$ | n-C$_5$H$_{11}$ |

In analogy to example 8 the compounds of the formula

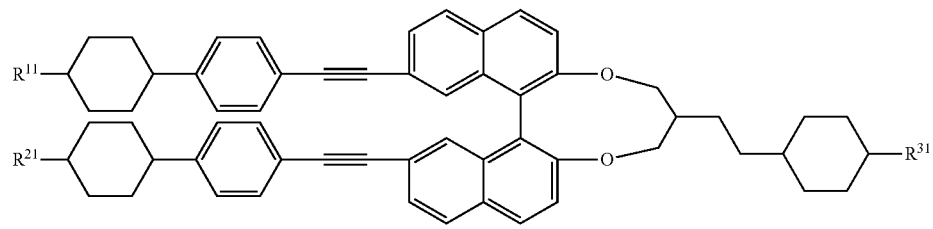

are obtained

| Example | $R^{11}$ | $R^{21}$ | $R^{31}$ |
|---|---|---|---|
| 226 | H | H | —CH$_3$ |
| 227 | H | H | —C$_2$H$_5$ |
| 228 | H | H | n-C$_3$H$_7$ |
| 229 | H | H | n-C$_4$H$_9$ |
| 230 | H | H | n-C$_5$H$_{11}$ |
| 231 | —CH$_3$ | —CH$_3$ | H |
| 232 | —CH$_3$ | —CH$_3$ | —CH$_3$ |
| 233 | —CH$_3$ | —CH$_3$ | —C$_2$H$_5$ |
| 234 | —CH$_3$ | —CH$_3$ | n-C$_3$H$_7$ |
| 235 | —CH$_3$ | —CH$_3$ | n-C$_4$H$_9$ |
| 236 | —CH$_3$ | —CH$_3$ | n-C$_5$H$_{11}$ |
| 237 | —C$_2$H$_5$ | —C$_2$H$_5$ | H |
| 238 | —C$_2$H$_5$ | —C$_2$H$_5$ | —CH$_3$ |
| 239 | —C$_2$H$_5$ | —C$_2$H$_5$ | —C$_2$H$_5$ |
| 240 | —C$_2$H$_5$ | —C$_2$H$_5$ | n-C$_3$H$_7$ |
| 241 | —C$_2$H$_5$ | —C$_2$H$_5$ | n-C$_4$H$_9$ |
| 242 | —C$_2$H$_5$ | —C$_2$H$_5$ | n-C$_5$H$_{11}$ |
| 243 | n-C$_3$H$_7$ | n-C$_3$H$_7$ | H |
| 244 | n-C$_3$H$_7$ | n-C$_3$H$_7$ | —CH$_3$ |
| 245 | n-C$_3$H$_7$ | n-C$_3$H$_7$ | —C$_2$H$_5$ |
| 8 | n-C$_3$H$_7$ | n-C$_3$H$_7$ | n-C$_3$H$_7$ |
| 246 | n-C$_3$H$_7$ | n-C$_3$H$_7$ | n-C$_4$H$_9$ |
| 247 | n-C$_3$H$_7$ | n-C$_3$H$_7$ | n-C$_5$H$_{11}$ |
| 248 | n-C$_4$H$_9$ | n-C$_4$H$_9$ | H |
| 249 | n-C$_4$H$_9$ | n-C$_4$H$_9$ | —CH$_3$ |
| 250 | n-C$_4$H$_9$ | n-C$_4$H$_9$ | —C$_2$H$_5$ |
| 251 | n-C$_4$H$_9$ | n-C$_4$H$_9$ | n-C$_3$H$_7$ |
| 252 | n-C$_4$H$_9$ | n-C$_4$H$_9$ | n-C$_4$H$_9$ |
| 253 | n-C$_4$H$_9$ | n-C$_4$H$_9$ | n-C$_5$H$_{11}$ |
| 254 | n-C$_5$H$_{11}$ | n-C$_5$H$_{11}$ | H |
| 255 | n-C$_5$H$_{11}$ | n-C$_5$H$_{11}$ | —CH$_3$ |
| 256 | n-C$_5$H$_{11}$ | n-C$_5$H$_{11}$ | —C$_2$H$_5$ |
| 257 | n-C$_5$H$_{11}$ | n-C$_5$H$_{11}$ | n-C$_3$H$_7$ |
| 258 | n-C$_5$H$_{11}$ | n-C$_5$H$_{11}$ | n-C$_4$H$_9$ |
| 259 | n-C$_5$H$_{11}$ | n-C$_5$H$_{11}$ | n-C$_5$H$_{11}$ |

In analogy to example 9 the compounds of the formula

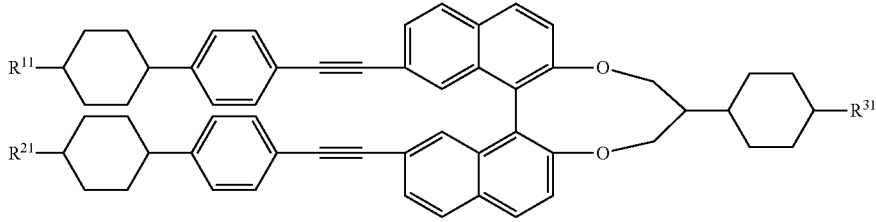

are obtained.

| Example | $R^{11}$ | $R^{21}$ | $R^{31}$ |
|---|---|---|---|
| 260 | H | H | —CH$_3$ |
| 261 | H | H | —C$_2$H$_5$ |
| 262 | H | H | n-C$_3$H$_7$ |
| 263 | H | H | n-C$_4$H$_9$ |
| 264 | H | H | n-C$_5$H$_{11}$ |
| 265 | —CH$_3$ | —CH$_3$ | H |
| 266 | —CH$_3$ | —CH$_3$ | —CH$_3$ |
| 267 | —CH$_3$ | —CH$_3$ | —C$_2$H$_5$ |
| 268 | —CH$_3$ | —CH$_3$ | n-C$_3$H$_7$ |
| 269 | —CH$_3$ | —CH$_3$ | n-C$_4$H$_9$ |
| 270 | —CH$_3$ | —CH$_3$ | n-C$_5$H$_{11}$ |
| 271 | —C$_2$H$_5$ | —C$_2$H$_5$ | H |
| 272 | —C$_2$H$_5$ | —C$_2$H$_5$ | —CH$_3$ |
| 273 | —C$_2$H$_5$ | —C$_2$H$_5$ | —C$_2$H$_5$ |
| 274 | —C$_2$H$_5$ | —C$_2$H$_5$ | n-C$_3$H$_7$ |
| 275 | —C$_2$H$_5$ | —C$_2$H$_5$ | n-C$_4$H$_9$ |
| 276 | —C$_2$H$_5$ | —C$_2$H$_5$ | n-C$_5$H$_{11}$ |
| 277 | n-C$_3$H$_7$ | n-C$_3$H$_7$ | H |
| 278 | n-C$_3$H$_7$ | n-C$_3$H$_7$ | —CH$_3$ |
| 279 | n-C$_3$H$_7$ | n-C$_3$H$_7$ | —C$_2$H$_5$ |
| 9 | n-C$_3$H$_7$ | n-C$_3$H$_7$ | n-C$_3$H$_7$ |
| 280 | n-C$_3$H$_7$ | n-C$_3$H$_7$ | n-C$_4$H$_9$ |
| 281 | n-C$_3$H$_7$ | n-C$_3$H$_7$ | n-C$_5$H$_{11}$ |
| 282 | n-C$_4$H$_9$ | n-C$_4$H$_9$ | H |
| 283 | n-C$_4$H$_9$ | n-C$_4$H$_9$ | —CH$_3$ |
| 284 | n-C$_4$H$_9$ | n-C$_4$H$_9$ | —C$_2$H$_5$ |
| 285 | n-C$_4$H$_9$ | n-C$_4$H$_9$ | n-C$_3$H$_7$ |
| 286 | n-C$_4$H$_9$ | n-C$_4$H$_9$ | n-C$_4$H$_9$ |
| 287 | n-C$_4$H$_9$ | n-C$_4$H$_9$ | n-C$_5$H$_{11}$ |
| 288 | n-C$_5$H$_{11}$ | n-C$_5$H$_{11}$ | H |
| 289 | n-C$_5$H$_{11}$ | n-C$_5$H$_{11}$ | —CH$_3$ |
| 290 | n-C$_5$H$_{11}$ | n-C$_5$H$_{11}$ | —C$_2$H$_5$ |
| 291 | n-C$_5$H$_{11}$ | n-C$_5$H$_{11}$ | n-C$_3$H$_7$ |
| 292 | n-C$_5$H$_{11}$ | n-C$_5$H$_{11}$ | n-C$_4$H$_9$ |
| 293 | n-C$_5$H$_{11}$ | n-C$_5$H$_{11}$ | n-C$_5$H$_{11}$ |

In analogy to example 10 the compounds of the formula

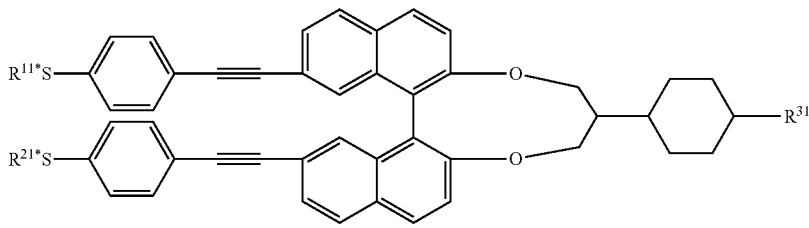

are obtained:

| Example | $R^{11*}$ | $R^{21*}$ | $R^{31}$ |
|---|---|---|---|
| 294 | H | H | —CH$_3$ |
| 295 | H | H | —C$_2$H$_5$ |
| 296 | H | H | n-C$_3$H$_7$ |
| 297 | H | H | n-C$_4$H$_9$ |
| 298 | H | H | n-C$_5$H$_{11}$ |
| 299 | —CH$_3$ | —CH$_3$ | H |
| 300 | —CH$_3$ | —CH$_3$ | —CH$_3$ |
| 301 | —CH$_3$ | —CH$_3$ | —C$_2$H$_5$ |
| 10 | —CH$_3$ | —CH$_3$ | n-C$_3$H$_7$ |
| 302 | —CH$_3$ | —CH$_3$ | n-C$_4$H$_9$ |
| 303 | —CH$_3$ | —CH$_3$ | n-C$_5$H$_{11}$ |
| 304 | —C$_2$H$_5$ | —C$_2$H$_5$ | H |
| 305 | —C$_2$H$_5$ | —C$_2$H$_5$ | —CH$_3$ |
| 306 | —C$_2$H$_5$ | —C$_2$H$_5$ | —C$_2$H$_5$ |
| 307 | —C$_2$H$_5$ | —C$_2$H$_5$ | n-C$_3$H$_7$ |
| 308 | —C$_2$H$_5$ | —C$_2$H$_5$ | n-C$_4$H$_9$ |
| 309 | —C$_2$H$_5$ | —C$_2$H$_5$ | n-C$_5$H$_{11}$ |
| 310 | n-C$_3$H$_7$ | n-C$_3$H$_7$ | H |
| 311 | n-C$_3$H$_7$ | n-C$_3$H$_7$ | —CH$_3$ |
| 312 | n-C$_3$H$_7$ | n-C$_3$H$_7$ | —C$_2$H$_5$ |
| 313 | n-C$_3$H$_7$ | n-C$_3$H$_7$ | n-C$_3$H$_7$ |
| 314 | n-C$_3$H$_7$ | n-C$_3$H$_7$ | n-C$_4$H$_9$ |
| 315 | n-C$_3$H$_7$ | n-C$_3$H$_7$ | n-C$_5$H$_{11}$ |
| 316 | n-C$_4$H$_9$ | n-C$_4$H$_9$ | H |
| 317 | n-C$_4$H$_9$ | n-C$_4$H$_9$ | —CH$_3$ |
| 318 | n-C$_4$H$_9$ | n-C$_4$H$_9$ | —C$_2$H$_5$ |
| 319 | n-C$_4$H$_9$ | n-C$_4$H$_9$ | n-C$_3$H$_7$ |
| 320 | n-C$_4$H$_9$ | n-C$_4$H$_9$ | n-C$_4$H$_9$ |
| 321 | n-C$_4$H$_9$ | n-C$_4$H$_9$ | n-C$_5$H$_{11}$ |
| 322 | n-C$_5$H$_{11}$ | n-C$_5$H$_{11}$ | H |
| 323 | n-C$_5$H$_{11}$ | n-C$_5$H$_{11}$ | —CH$_3$ |
| 324 | n-C$_5$H$_{11}$ | n-C$_5$H$_{11}$ | —C$_2$H$_5$ |
| 325 | n-C$_5$H$_{11}$ | n-C$_5$H$_{11}$ | n-C$_3$H$_7$ |
| 326 | n-C$_5$H$_{11}$ | n-C$_5$H$_{11}$ | n-C$_4$H$_9$ |
| 327 | n-C$_5$H$_{11}$ | n-C$_5$H$_{11}$ | n-C$_5$H$_{11}$ |

Example 328 (Not in Accordance with the Invention): 2,2'-Methylenedioxy-7-[4-(4-propyl-cyclohexyl)phenyl]-[1,1']binaphthalene The starting material, 2,2'-Methylenedioxy-7,7'-dibromo [1,1']binaphthalene is described in the literature [CAS-No. 263339-97-5].

328.1 2,2'-Methylenedioxy-7-bromo-7'-[4-(4-propyl-cyclohexyl)phenyl]-[1,1']binaphthalene 7.00 g (15.3 mmol) 2,2'-methylenedioxy-7,7'-dibromo[1, 1']binaphthalene and 4-(4-propyl-cyclohexyl)benzene boronic acid are dissolved in 150 ml of THF and after addition of 3.24 g (23.0 mmol) sodium metaborate-tetrahydrate, 1.08 g (1.54 mmol) bis(triphenylphosphine) palladium (II)chloride and 7 µl of hydrazinium hydrate, the reaction is heated at reflux overnight. The reaction is poured onto water, the aqueous layer is extracted with ether and the combined org. layers are washed with brine and dried over sodium sulfate. The solvent is evaporated and the residue is purified by chromatography to give 2,2'-methylenedioxy-7-bromo-7'-[4-(4-propyl-cyclohexyl)phenyl]-[1,1']binaphthalene as a colourless solid.

328.2 2,2'-Methylenedioxy-7-[4-(4-propyl-cyclohexyl)phenyl]-[1,1']binaphthalene

-continued

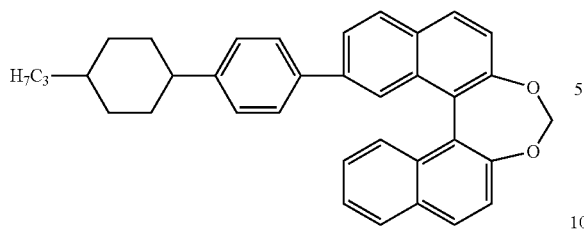

2,2'-Methylenedioxy-7-bromo-7'-[4-(4-propyl-cyclohexyl)phenyl]-[1,1']binaphthalene is hydrogenated in THF on palladium-C (5%) catalyst until one equivalent of hydrogen is consumed. The catalyst is filtered off, the filtrate is evaporated and the residue is purified by chromatography to give 2,2'-Methylenedioxy-7-[4-(4-propyl-cyclohexyl)phenyl]-[1,1']binaphthalene as colourless crystals, m.p. 152° C.

2. HTP Measurements

A nematic Host N1 for HTP measurements is prepared as follows

| Compound | % | | |
|---|---|---|---|
| CPG-3-F | 7.50% | Clp. | 60° C. |
| CPG-5-F | 7.50% | | |
| PZG-2-F | 9.50% | | |
| PZG-2-F | 10.00% | | |
| PGP-2-3 | 8.00% | | |
| PGU-2-F | 9.00% | | |
| PGU-3-F | 9.00% | | |
| PGUQU-3-F | 9.50% | | |
| PGUQU-4-F | 9.50% | | |
| PGUQU-5-F | 9.50% | | |
| PUQU-2-F | 5.50% | | |
| PUQU-3-F | 5.50% | | |

The HTP values are measured as described above and are listed in table 1.

TABLE 1

| Compound | Example | HTP [μm$^{-1}$] [1] | HTP [μm$^{-1}$] [2] |
|---|---|---|---|
| R-5011 | c.s. | 95 | 145 |
| 1 | 1 | 119 | N/A |
| 2 | 2 | 103 | N/A |
| 3 | 3 | 100 | N/A |
| 4 | 4 | 120 | N/A |
| 5 | 5 | 128 | 200 |
| 6 | 6 | 146 | 271 |
| 7 | 7 | 141 | 201 |
| 8 | 8 | 124 | 204 |
| 9 | 9 | 137 | 220 |
| 10 | 10 | 129 | 208 | c.s.: comparative substance 1
[1] measured in MLC-6260
[2] measured in N1

As shown in table 1, compounds of examples 1 to 10 exhibit significantly higher HTP values than R-5011 from the state of the art.

3. Mixture Examples

Comparative Example 1

A cholesteric mixture C1 contains 96.98% of a nematic component N2:

TABLE 1

| Nematic Host N2 | | | |
|---|---|---|---|
| CC-5-O1 | 7.0% | Kp. | 86 |
| CCZC-3-3 | 3.0% | | |
| CCZC-3-5 | 3.0% | Δn | 0.0645 |
| CCZC-4-3 | 3.0% | n$_e$ | 1.5325 |
| CCU-2-F | 7.0% | | |
| CCU-3-F | 5.0% | Δε | +10.2 |
| CCZU-2-F | 6.0% | | |
| CCZU-3-F | 15.0% | | |
| CCZU-5-F | 6.0% | | |
| CDU-2-F | 9.0% | | |
| CDU-3-F | 9.0% | | |
| CDU-5-F | 16.0% | | |
| CC-3-T | 7.0% | | |
| CC-5-T | 8.0% | | |
| CCZPC-3-4 | 3.0% | | |
| CCZPC-3-3 | 3.0% | | | and 3.02% of chiral dopant R-5011 of formula

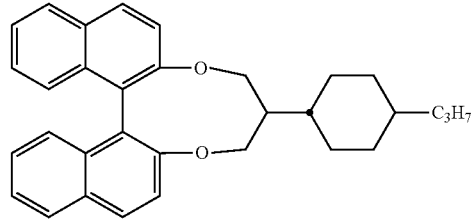

The mixture C1 shows a reflection wavelength of λ=400 nm.

Mixture Example M1

A cholesteric mixture M1 is prepared from nematic host N2 above and the compound of synthesis example 1.

TABLE 2

| Cholesteric mixture M1 | |
|---|---|
| | Mass % |
| N2 | 97.59 |
| Example 1 | 2.41 |

Mixture Example M2

A cholesteric mixture M2 is prepared from nematic host N2 above and the compound of synthesis example 6.

TABLE 3

| Cholesteric mixture M2 | |
|---|---|
| | Mass % |
| N2 | 98.19 |
| Example 6 | 1.81 |

Mixture Example M3

A nematic Host N3 is prepared as follows:

TABLE 4

Nematic Host N3

| | | | |
|---|---|---|---|
| GUQGU-3-F | 8.00% | Kp. | 72.5 |
| GUQGU-4-F | 6.00% | | |
| GUQGU-5-F | 4.00% | $\Delta n$ | 0.1929 |
| GUUQU-3-N | 6.00% | $n_e$ | 1.6811 |
| GUQU-3-F | 7.00% | $n_o$ | 1.4882 |
| GUQU-4-F | 6.00% | | |
| GUQGU-2-T | 12.00% | $\Delta\varepsilon$ | 202.1 |
| GUQGU-3-T | 12.00% | $\varepsilon_\parallel$ | 213.6 |
| GUQGU-4-T | 12.00% | $\varepsilon_\perp$ | 11.5 |
| GUQGU-5-T | 12.00% | | |
| DPGU-4-F | 8.00% | | |
| PGU-5-T | 3.00% | | |
| PGU-4-T | 4.00% | | |

A Blue Phase mixture M3 is prepared from the nematic host mixture N3 above and the compound of synthesis example 6:

TABLE 5

Blue Phase mixture M3

| | Mass % |
|---|---|
| N3 | 97.2 |
| Example 6 | 2.8 |

The invention claimed is:

1. A process comprising alkylating or acetalizing a compound of the formula

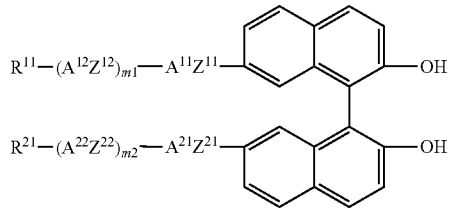

to produce a compound of the formula

I-2

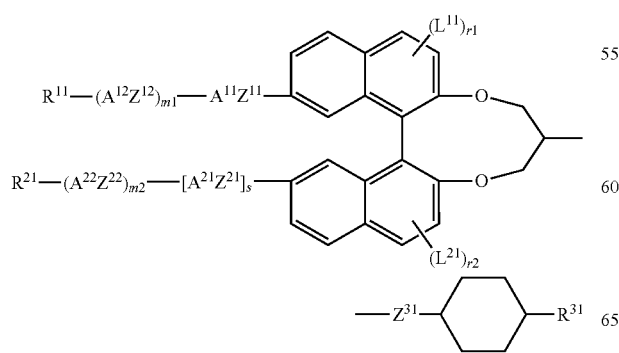

I-3

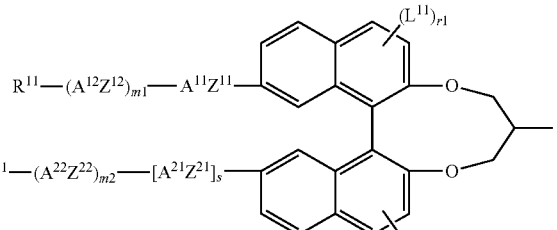

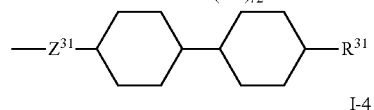

I-4

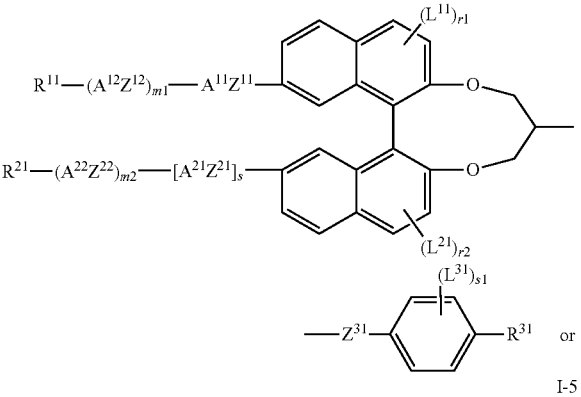

or

I-5

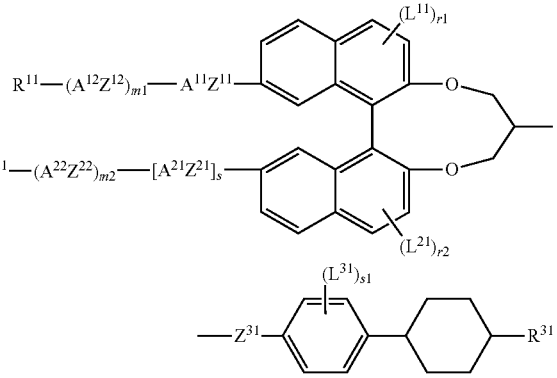

wherein $A^{11}$, $A^{12}$, $A^{21}$, $A^{22}$ each, identically or differently, denote 1,4-phenylene, 1,4-cyclohexylene, naphthalene-2,6-diyl, it being possible for all these groups to be unsubstituted, mono- or polysubstituted with $L^{31}$, $R^{11}$, $R^{21}$, $R^{31}$ each, identically or differently, denote H, F, Cl, CN, straight chain or branched alkyl with up to 7 C atoms which may be unsubstituted, mono- or polysubstituted by F, Cl, or CN, it being also possible for one or more non-adjacent $CH_2$ groups to be replaced, in each case independently from one another, by —O—, —CO—, —C(O)O—, —OC(O)—, —OCO—O—, —SC(O)—, —C(O)S—, —CH=CH— or —C≡C— in such a manner that —O— and/or —S— atoms are not linked directly to one another, or a polymerizable group, $Z^{11}$, $Z^{12}$, $Z^{21}$ and $Z^{22}$ each, identically or differently, denote —O—, —CO—, —C(O)O—, —OC(O)—, —O—C(O)O—, —OCH₂—, —CH₂O—, —CF₂O—, —OCF₂—, —CH₂CH₂—, —CF₂CH₂—, —CH₂CF₂—, —CF₂CF₂—, —CH=CH—, —CF=CH—, —CH=CF—, —CF=CF—, —C≡C—, or a single bond, $Z^{31}$ denotes —O—, —OC(O)—, —OCH₂—, —CH₂CH₂—, —CF₂CH₂—, —CH₂CF₂—, —CF₂CF₂— or a single bond, $L^{11}, L^{21}, L^{31}$ each, identically or differently, denote F, Cl, or alkyl or alkoxy with 1 to 7 C atoms, wherein one or more H atoms may be substituted by F or Cl, m1, m2 each, identically or differently, is 0, 1, 2 or 3, r1, r2, s1 each, identically or differently, are 0, 1 or 2, and s denotes 0 or 1.

\* \* \* \* \*